United States Patent
Anagnostopoulos

(10) Patent No.: US 11,602,628 B2
(45) Date of Patent: Mar. 14, 2023

(54) INTRA-AORTIC BALLOON APPARATUS, ASSIST DEVICES AND METHODS FOR IMPROVING FLOW, COUNTERPULSATION AND HAEMODYNAMICS

(71) Applicant: Constantinos Anagnostopoulos, Manchester (GB)

(72) Inventor: Constantinos Anagnostopoulos, Manchester (GB)

(*) Notice: Subject to any disclaimer, the term of this patent is extended or adjusted under 35 U.S.C. 154(b) by 293 days.

(21) Appl. No.: 16/006,111

(22) Filed: Jun. 12, 2018

(65) Prior Publication Data
US 2019/0083689 A1 Mar. 21, 2019

Related U.S. Application Data

(63) Continuation of application No. 14/899,804, filed as application No. PCT/IB2014/001672 on Jun. 20, 2014, now Pat. No. 10,137,231.
(Continued)

(51) Int. Cl.
*A61M 60/896* (2021.01)
*A61M 60/497* (2021.01)
(Continued)

(52) U.S. Cl.
CPC .......... *A61M 60/896* (2021.01); *A61M 60/13* (2021.01); *A61M 60/139* (2021.01);
(Continued)

(58) Field of Classification Search
None
See application file for complete search history.

(56) References Cited

U.S. PATENT DOCUMENTS

| 4,077,394 A | 3/1978 | McCurdy |
| 4,407,271 A | 10/1983 | Schiff |

(Continued)

FOREIGN PATENT DOCUMENTS

| JP | H06-296703 A | 10/1994 |
| JP | H07-265410 A | 10/1995 |

(Continued)

OTHER PUBLICATIONS

PCT, International Search Report and Written Opinion, International Application No. PCT/IB2014/001672, dated Feb. 13, 2015.
(Continued)

*Primary Examiner* — Ankit D Tejani
(74) *Attorney, Agent, or Firm* — FisherBroyles, LLP; Clifton E. McCann

(57) ABSTRACT

A circulatory assist apparatus comprising: an inflatable pumping balloon having a proximal end joined to an elongated balloon catheter, the balloon catheter having a distal end joined to the pumping balloon and a proximal end, separated from the distal end by a length sufficient to extend from within a circulatory lumen to the outside of a patient's body, for receiving positive and negative pressure pulses from a pump to inflate and deflate the pumping balloon; and a radially expandable frame, mounted on one of a segment extending distally from the pumping balloon, the balloon catheter, and a sleeve tube surrounding the balloon catheter. The expandable frame is manipulate to expand within the circulatory lumen, and functions to space apart the inflatable balloon from the circulatory lumen, having a first diameter in a collapsed configuration for intraluminal delivery and a second, larger diameter in an expanded configuration achieved by said manipulation.

20 Claims, 34 Drawing Sheets

Related U.S. Application Data

(60) Provisional application No. 61/837,173, filed on Jun. 20, 2013.

(51) Int. Cl.

| | | |
|---|---|---|
| *A61M 60/865* | (2021.01) | |
| *A61M 60/295* | (2021.01) | |
| *A61M 60/139* | (2021.01) | |
| *A61M 60/13* | (2021.01) | |
| *A61M 60/843* | (2021.01) | |
| A61M 60/148 | (2021.01) | |
| A61M 60/274 | (2021.01) | |

(52) U.S. Cl.
CPC ........ *A61M 60/295* (2021.01); *A61M 60/497* (2021.01); *A61M 60/843* (2021.01); *A61M 60/865* (2021.01); *A61M 60/148* (2021.01); *A61M 60/274* (2021.01)

(56) References Cited

U.S. PATENT DOCUMENTS

| | | |
|---|---|---|
| 4,444,186 A | 4/1984 | Wolvek |
| 4,515,587 A | 5/1985 | Schiff |
| 4,522,195 A | 6/1985 | Schiff |
| 4,785,795 A | 11/1988 | Singh |
| 5,122,113 A | 6/1992 | Hattier |
| 5,169,378 A | 12/1992 | Figuera |
| 5,176,619 A | 1/1993 | Segalowitz |
| 5,318,501 A | 6/1994 | Lee et al. |
| 5,336,178 A | 8/1994 | Kaplan et al. |
| 5,503,636 A | 4/1996 | Schmitt et al. |
| 5,810,871 A | 9/1998 | Tuckey et al. |
| 5,820,542 A | 10/1998 | Dobak, III et al. |
| 5,868,783 A | 2/1999 | Tower |
| 5,913,871 A | 6/1999 | Werneth et al. |
| 5,957,949 A | 9/1999 | Leonhardt et al. |
| 5,976,181 A | 11/1999 | Whelan et al. |
| 6,019,785 A | 2/2000 | Strecker |
| 6,143,016 A | 11/2000 | Bleam et al. |
| 6,149,578 A | 11/2000 | Downey et al. |
| 6,210,318 B1 | 4/2001 | Lederman |
| 6,238,412 B1 | 5/2001 | Dubrul et al. |
| 6,506,202 B1 | 1/2003 | Dutta et al. |
| 7,144,364 B2 | 12/2006 | Barbut et al. |
| 7,374,531 B1 | 5/2008 | Kantrowitz |
| 7,955,350 B2 | 6/2011 | Konstantino et al. |
| 8,287,563 B2 | 10/2012 | Khairkhahan |
| 8,480,555 B2 | 7/2013 | Kung |
| 8,574,258 B2 | 11/2013 | Braun et al. |
| 8,585,572 B2 | 11/2013 | Mehmanesh |
| 8,740,961 B2 | 6/2014 | Fulton, III |
| 8,784,480 B2 | 7/2014 | Taylor et al. |
| 2004/0059179 A1 | 3/2004 | Maguire |
| 2004/0097784 A1 | 5/2004 | Suttle et al. |
| 2008/0033476 A1 | 2/2008 | Greene |
| 2008/0183136 A1 | 7/2008 | Lenker |
| 2010/0049292 A1 | 2/2010 | Fiorella |
| 2010/0228077 A1 | 9/2010 | Lenker |
| 2010/0298922 A1 | 11/2010 | Thornton |
| 2011/0040319 A1 | 2/2011 | Fulton, III |
| 2011/0087322 A1 | 4/2011 | Letac |
| 2011/0106115 A1 | 5/2011 | Haselby et al. |
| 2011/0270174 A1 | 11/2011 | Ehrenreich |
| 2011/0270175 A1 | 11/2011 | Ehrenreich |
| 2011/0270176 A1 | 11/2011 | Ehrenreich |
| 2011/0270224 A1 | 11/2011 | Ehrenreich |
| 2012/0172844 A1* | 7/2012 | Mullen ............ A61M 25/09 604/528 |
| 2012/0226340 A1 | 9/2012 | Leschinsky |
| 2012/0308406 A1 | 12/2012 | Schumacher |
| 2012/0330092 A1 | 12/2012 | Shiose et al. |
| 2013/0035628 A1 | 2/2013 | Garrison |
| 2014/0243873 A1 | 8/2014 | Franklin et al. |

FOREIGN PATENT DOCUMENTS

| | | |
|---|---|---|
| JP | 2008/534032 A | 8/2008 |
| WO | 02/102436 A2 | 12/2002 |
| WO | 2005/082440 A1 | 9/2005 |
| WO | 2013/074185 A1 | 5/2013 |

OTHER PUBLICATIONS

AU, Examination Report No. 1 for Standard Patent Application, Australian Patent Application No. 2014282204, 6 pages, dated Mar. 5, 2018.

U.S., Non-Final Office Action, U.S. Appl. No. 14/899,804, 22 pages, dated Feb. 14, 2017.

U.S., Final Office Action, U.S. Appl. No. 14/899,804, 18 pages, dated Jul. 25, 2017.

U.S., Notice of Allowance, U.S. Appl. No. 14/899,804, 11 pages, dated Feb. 21, 2018.

European Patent Office, Communication Under Rule 71 (3) EPC (Intent to Grant), European Patent Application No. 14793282.6, 7 pages, dated Jun. 8, 2018.

EP, Extended Search Report, European Application No. 18204523.7 (dated Mar. 14, 2019).

JP, Japan Patent Office, Notice of Reasons for Rejection (with English translation), Japanese Patent Application No. 2016-520757, 8 pages, dated Jun. 18, 2019.

* cited by examiner

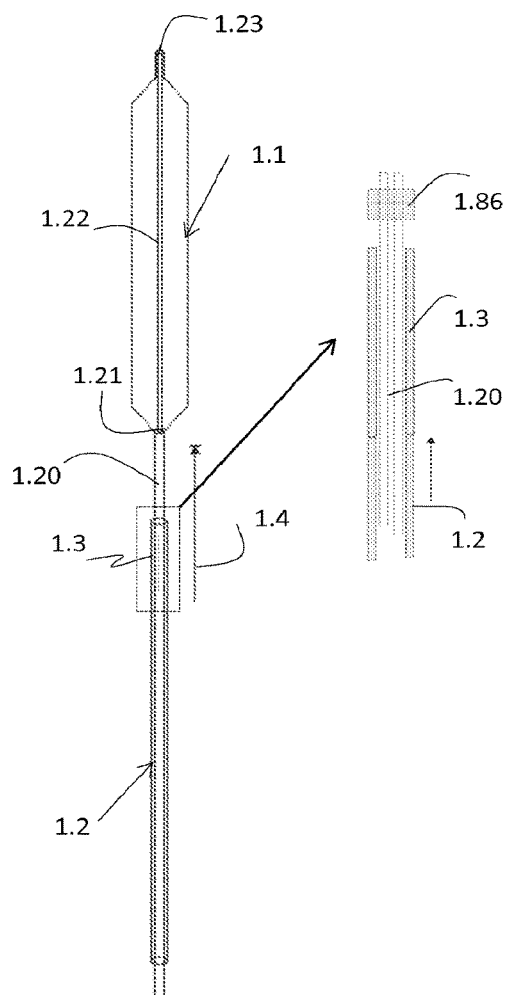
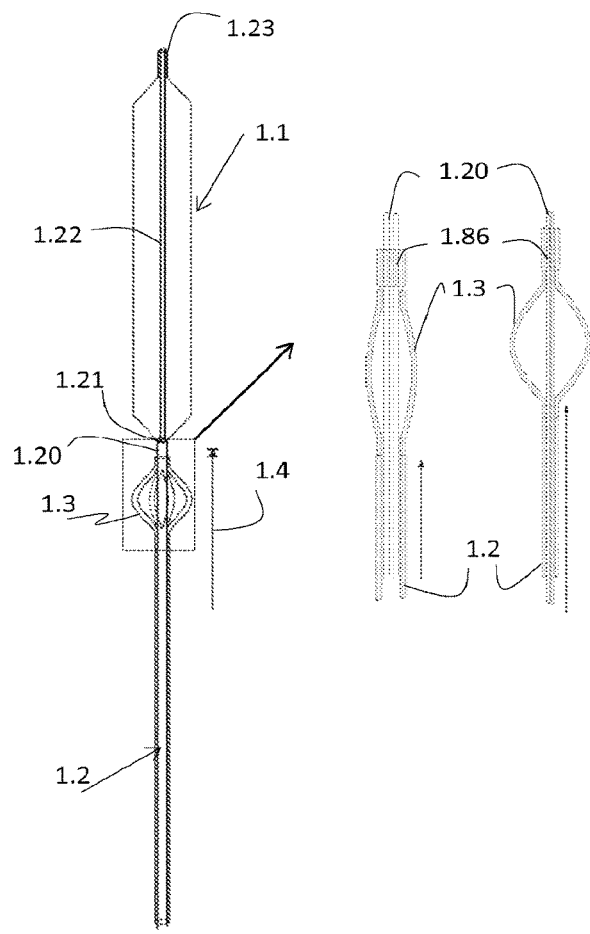
Fig. 1a
Fig. 1b
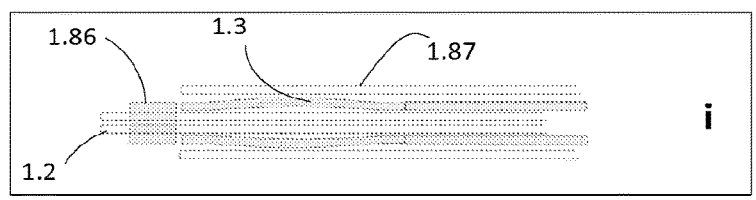
Fig. 1 sub

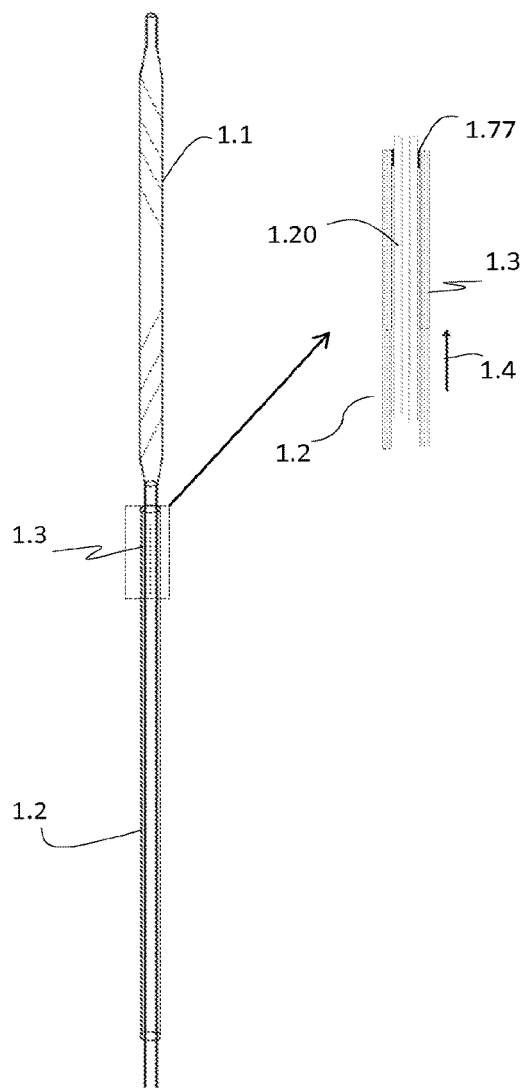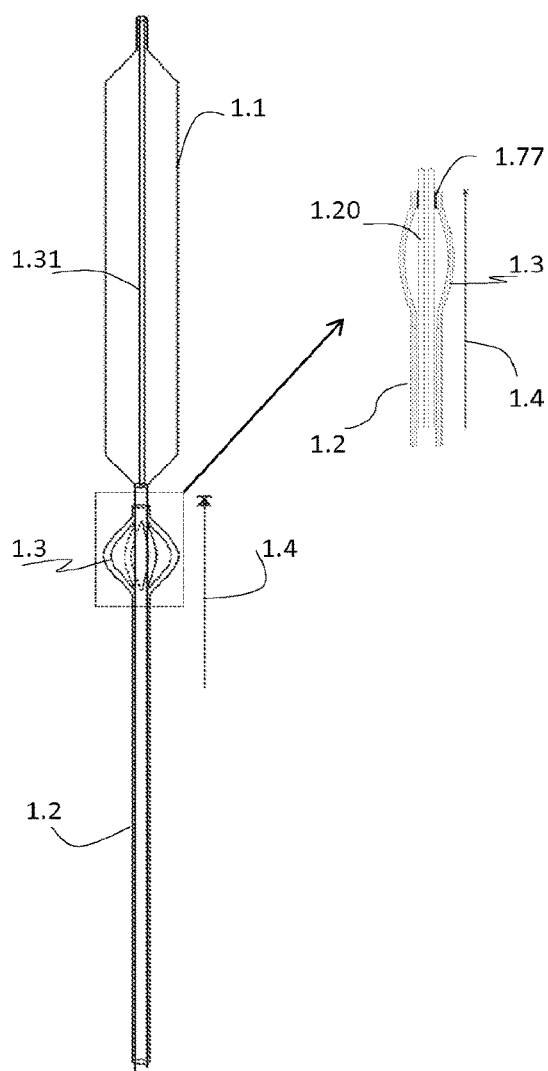
Fig. 1c    Fig. 1d
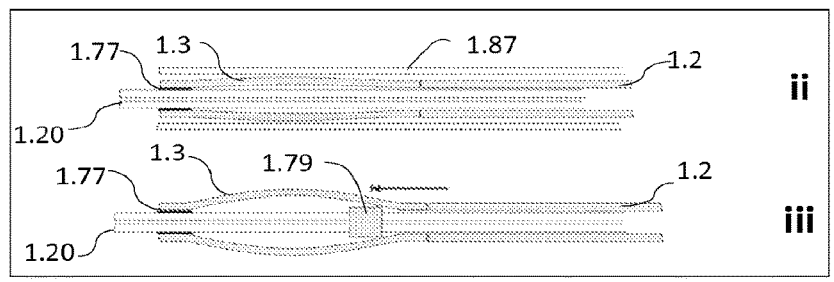
Fig. 1 sub

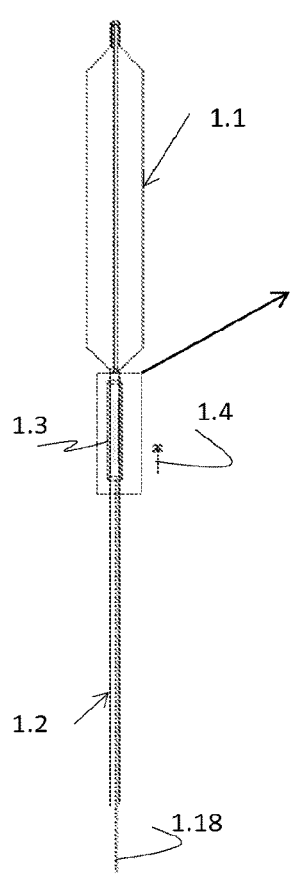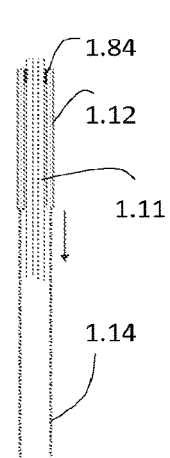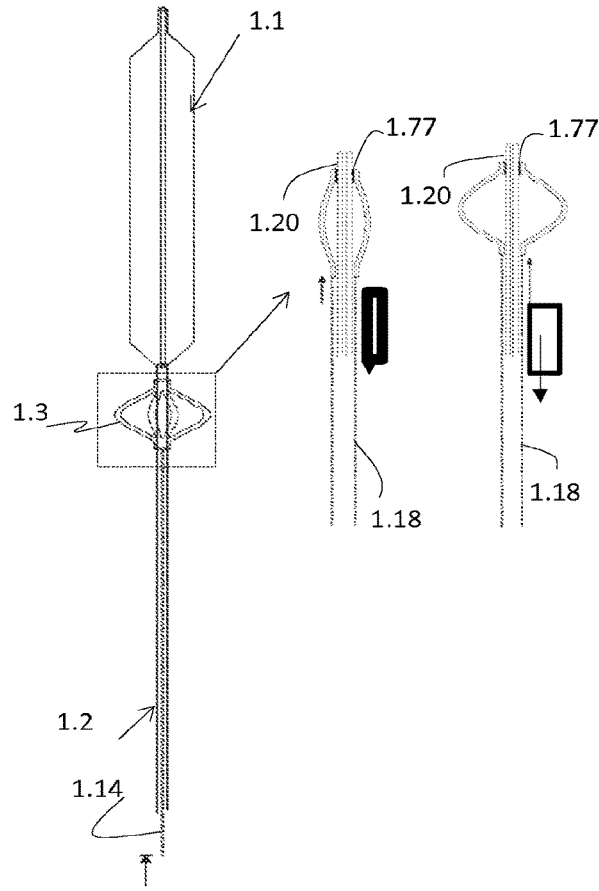
Fig. 1e
Fig. 1f
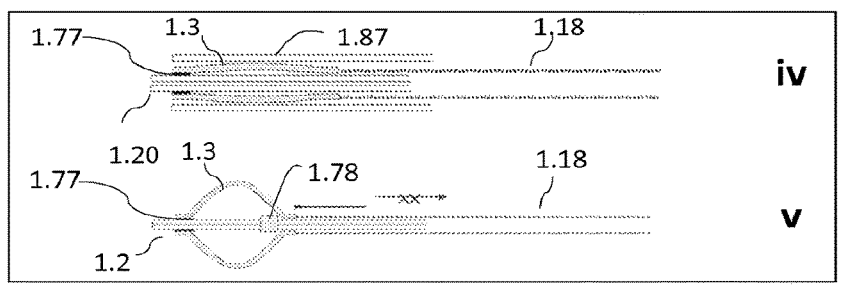
Fig. 1 sub

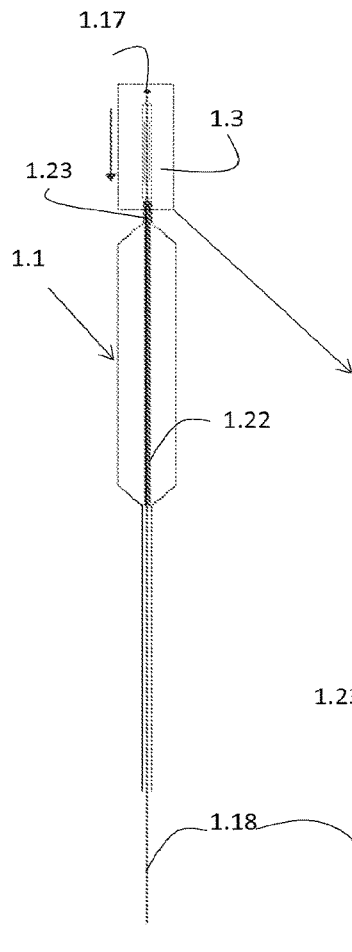
Fig. 1g
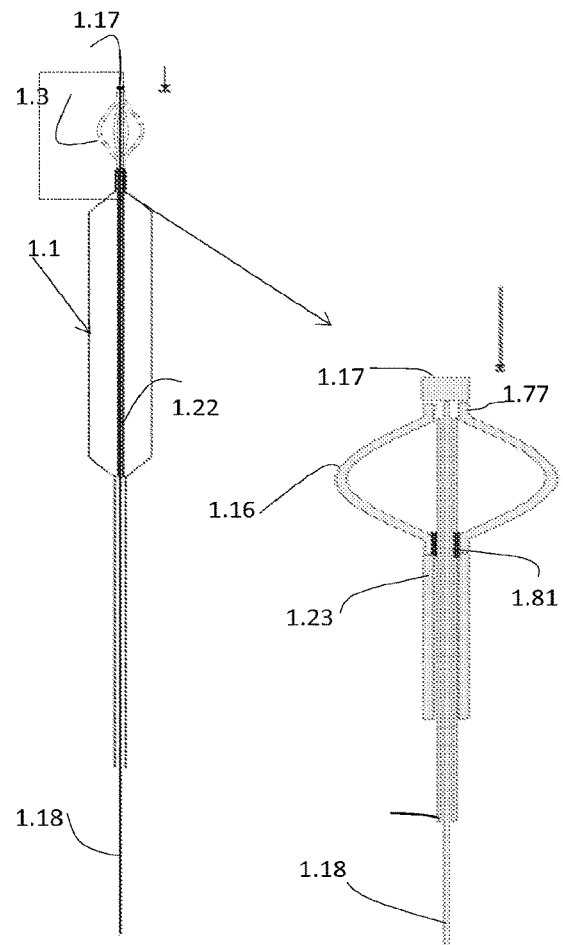
Fig. 1h
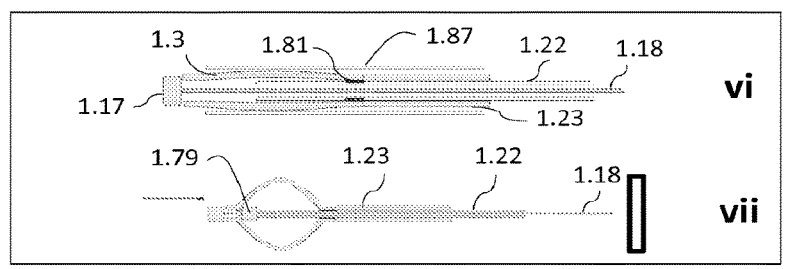
Fig. 1 sub

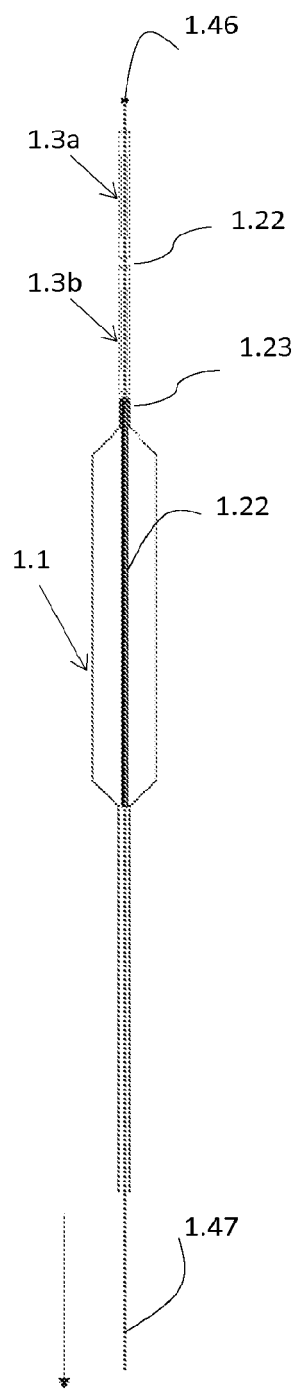
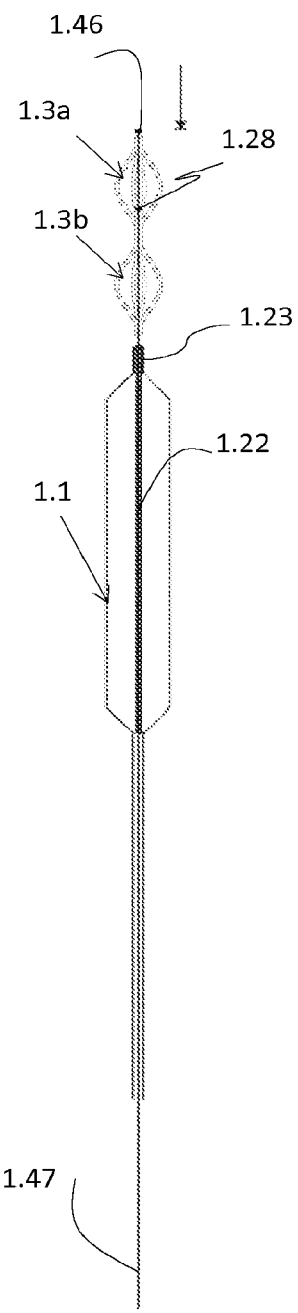
Fig. 1i          Fig. 1j

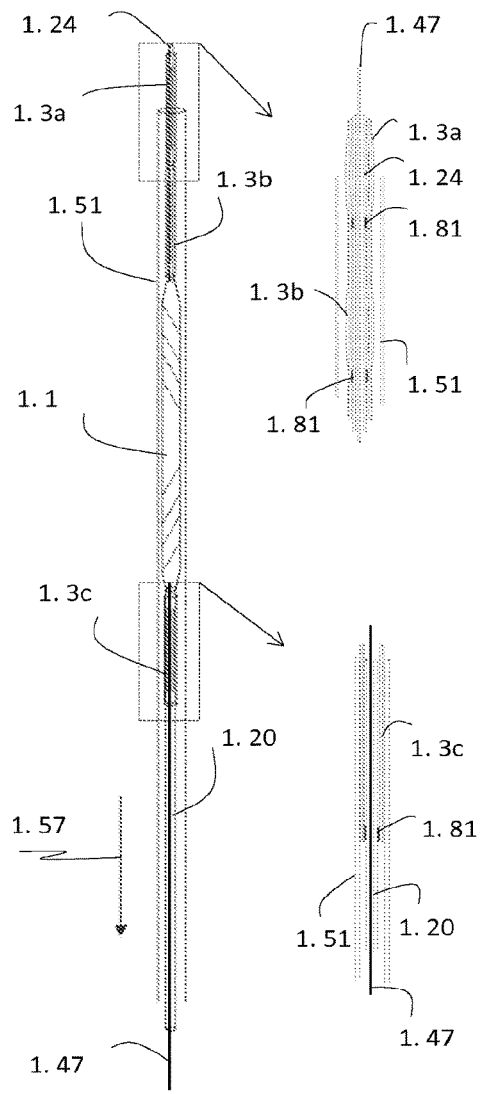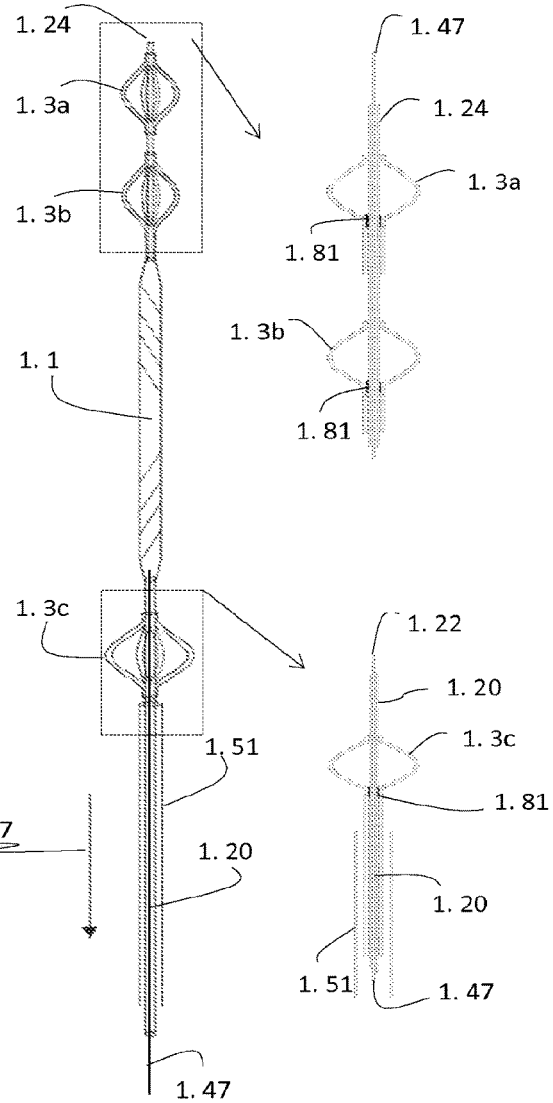
Fig. 1n
Fig. 1o
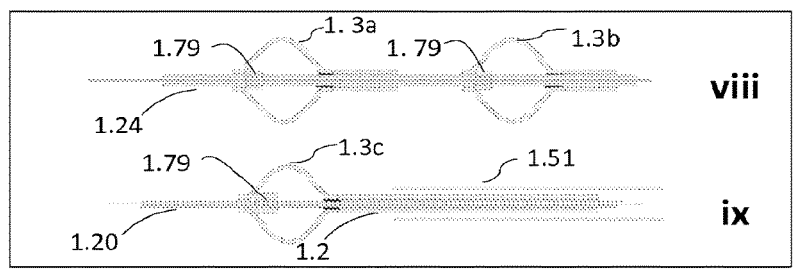
Fig. 1 sub

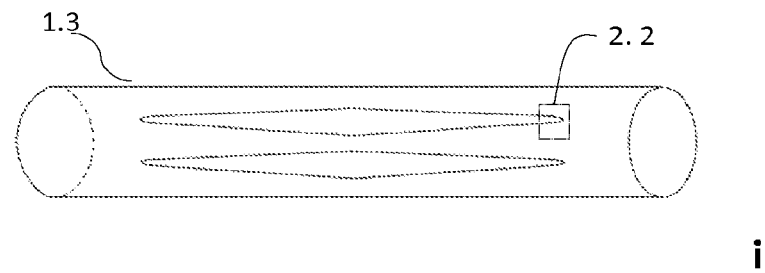
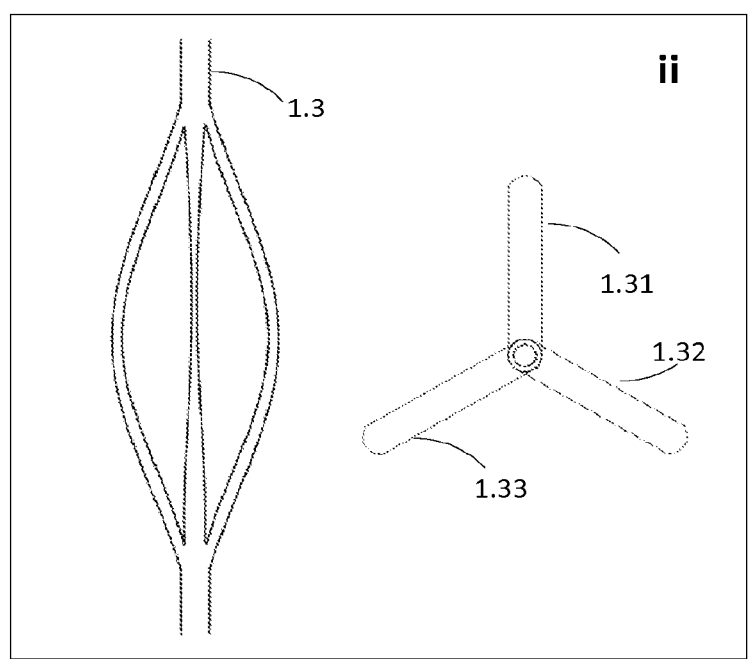
Fig. 2b

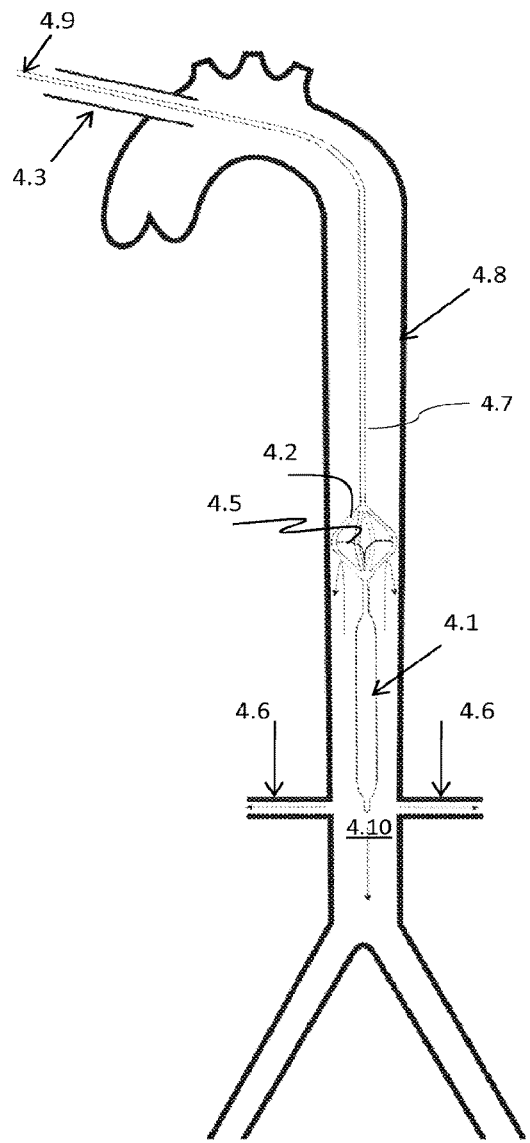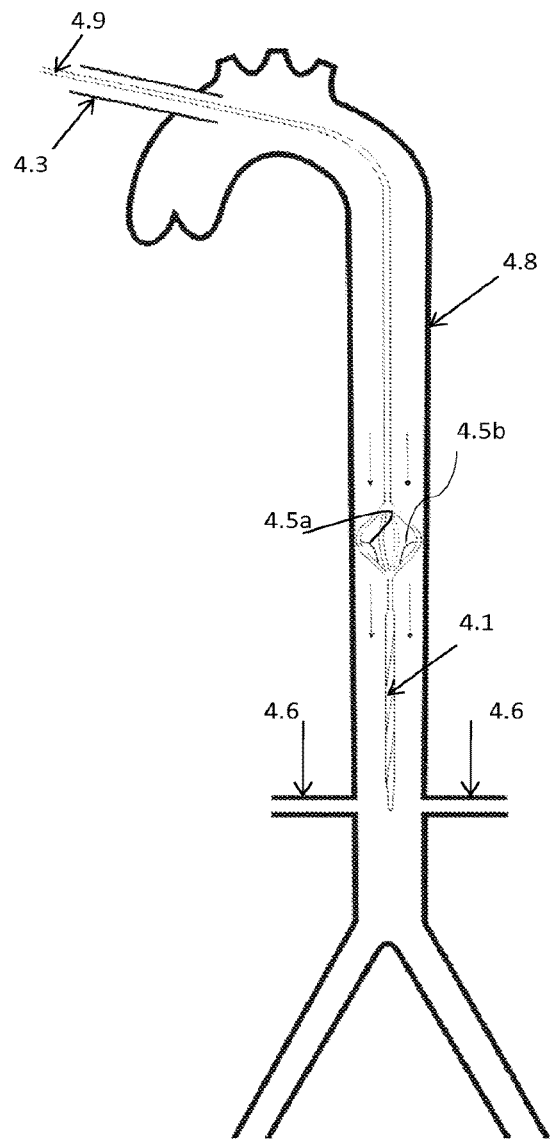
Fig. 4a                                    Fig. 4b

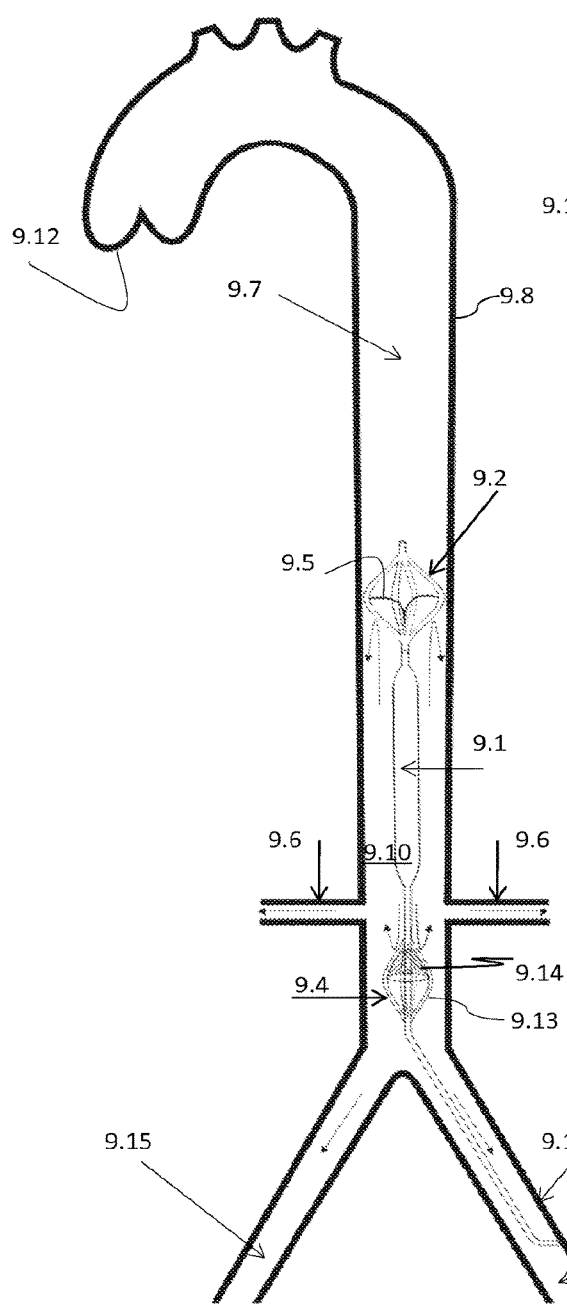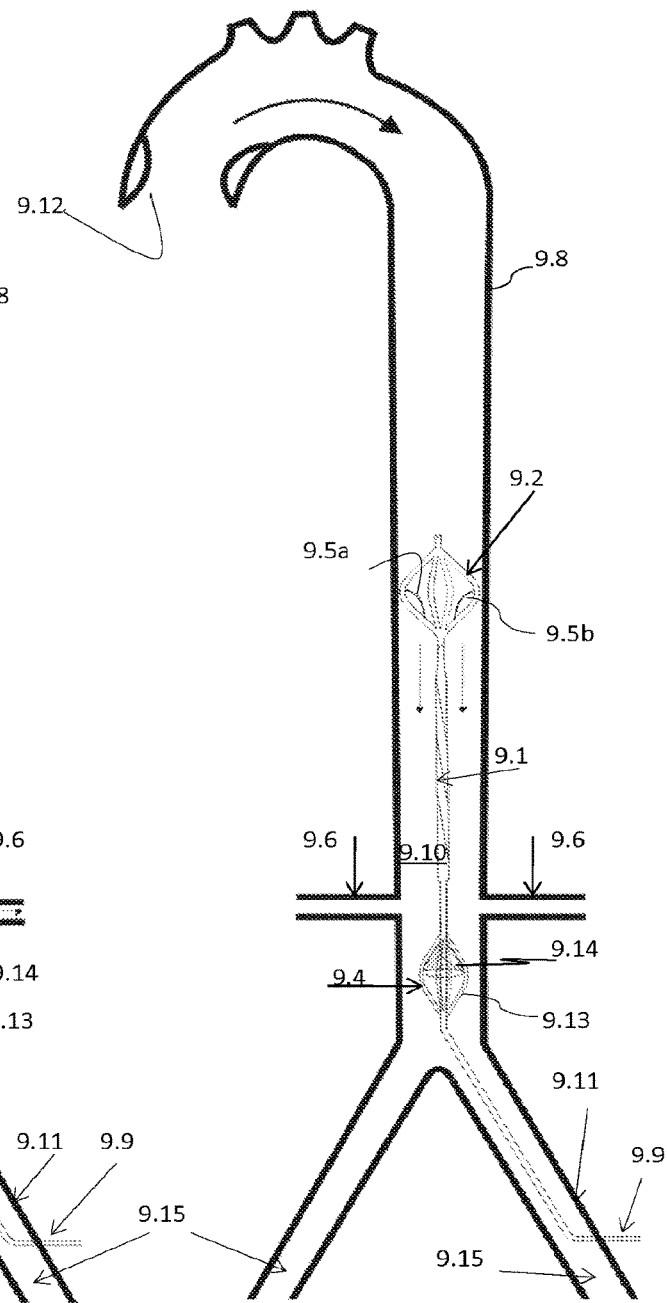
Fig. 9a                    Fig. 9b

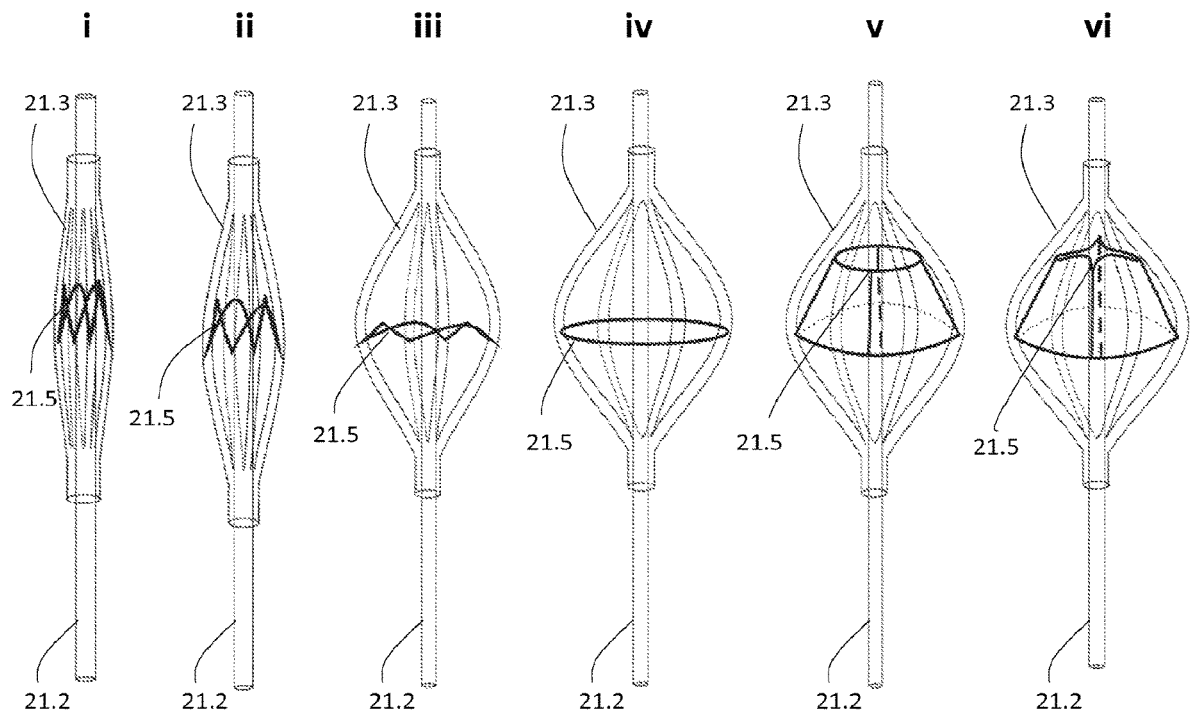
Fig. 21
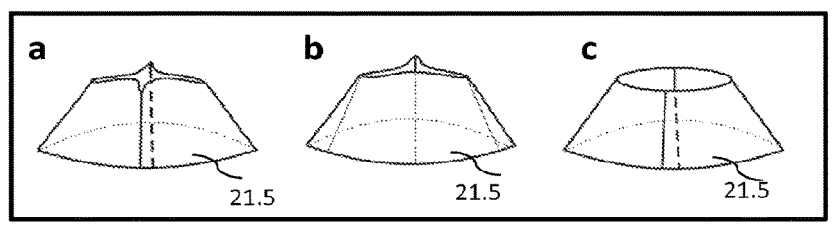
Fig. 21 sub

INTRA-AORTIC BALLOON APPARATUS, ASSIST DEVICES AND METHODS FOR IMPROVING FLOW, COUNTERPULSATION AND HAEMODYNAMICS

This application is a continuation of U.S. patent application Ser. No. 14/899,804, filed Dec. 18, 2015, which is a National Stage filing of International Application No. PCT/IB2014/001672, filed Jun. 20, 2014, which claims priority from U.S. Provisional Patent Application No. 61/837,173, filed Jun. 20, 2013, the entireties of which are hereby incorporated by reference, where permitted.

BACKGROUND AND RELATED ART

1) Basic IAB Counterpulsation Principles and Limitations

Intra-Aortic balloon (IAB) assist devices are devices used to assist the pumping function of a failing heart. In their simpler application they are comprised of a pneumatic pump system inflating and deflating a balloon periodically. The balloon is positioned in the aorta and gated with the failing heart in counterpulsation mode. Gating is such that balloon deflates when the heart is in systole, and inflates when the heart is in diastole. The principle behind counterpulsation relies on the following facts:
1. During systole, deflation of the balloon creates an empty space within the aorta which 'vacuums' blood out of the Left Ventricle (LV). Drawing blood from the LV assists the effort of the failing heart to pump out blood ("after-load decrease").
2. During diastole, whilst the aortic valve is closed and the LV is receiving blood for the next cardiac cycle, the balloon inflates within the aorta. The previously blood-filled aortic space is abruptly occupied by the inflated balloon, which raises the pressure in the aorta and ejects blood towards all directions, apart from into the heart, thus augmenting circulatory blood flow.

In order for an IAB to be clinically effective, meaning to accomplish a reasonable cardiac after-load decrease and at least a 30% aortic pressure augmentation in a 1.80 m patient, a balloon volume of at least 34 mLs displacement volume is usually used. Given the fact that the LV pumps out an average of 70 mLs in every heartbeat, this displacement volume of 34 mLs represents about half of that volume (~34/70=49% ejection fraction). It is easily understood that if the current IAB was a perfect "LV suction pump" system, it would be expected to draw all its 34 mLs displacement volume from the LV and thus achieve easily a ~50% ejection fraction during deflation Equally it would be expected to achieve a similar 50% pressure assist effect on the beating heart. Instead, existing devices typically achieve only about a 10-20% pressure assist effect. This is disproportionate.

The disparity between balloon volume and pressure assist effect is largely due to four specific facts, each one of which contributes independently to the IAB's pressure wave loss:
1. The initially transverse direction of the inflated balloon's expansion pulse wave, which creates energy loss through a shock wave exerted on the aorta, prior to generating an effective axial pulse wave.
2. The elastic properties of the aorta, which absorbs a substantial portion of the pulse wave energy generated by the balloon.
3. The distance of the IAB from the heart, which in combination with the facts (1) and (2) result in "waste" of a large proportion of the balloon's pressure wave through absorption of the pulse waves within the aorta. It is important to stress that current IAB designs prohibit placement within the Aortic arch, as it would cause severe "whipping" trauma upon inflation of the balloon.
4. Most importantly, undesired retrograde flow during the balloon's deflation, from the lower abdominal and iliac circulation, which absorbs almost half of the IAB's desired vacuum effect on the heart.

Although a large balloon counterpulsation volume could be used in an effort to provide a desired level of pressure augmentation, other important factors co-exist, posing additional burdens.

It is well known, to those familiar with the art, that the IAB is percutaneously inserted as a folded structure through an incision in a major peripheral artery, such as the femoral artery, measuring 4-7 mm. The IAB is connected to a helium pump through a balloon catheter which cyclically supplies helium into and vacuums helium from the IAB during inflation and deflation. The diameter of the catheter doesn't usually exceed the 2.5-3 mm due to the associated arterial trauma and the compromise of femoral circulation from the space occupied by the balloon catheter. It is therefore obvious that although large balloon volumes could be accomplished with a bigger balloon catheter size, this is limited by the arterial diameter at the insertion site.

2) Limitations in the Use of IAB in Non-Cardiac Pathologies

Despite the IAB's burdens described above, IAB is yet able to assist cardiac pumping function, improve cardiac output, and increase coronary blood supply to the heart. There are also a number of non-cardiac clinical conditions in which pressure or flow augmentation in the circulation would be desirable. Some of the most common are: ischemic stroke, renal failure, and ischemic bowel. Many of these conditions are typically encountered in certain clinical context of low perfusion pressures, such as that of the post-operative cardiac surgery patient, due to the perioperative low blood flow during Cardiopulmonary By Pass (CPB). The more compromised the blood flow is in a particular body organ pre-operatively (due to diabetes, atherosclerosis, etc.), the more vulnerable it is to develop ischemia post-operatively due to the low pressure blood flows during the operation. As a result stroke, renal failure, and bowel necrosis may occur post-operatively, in a percentage as high as 30%, depending on the actual age range and the underlying susceptibility to ischemia of the population group under study. Although IAB pressure augmentation would be a reasonable approach to treat all the clinical groups mentioned above, in clinical reality this doesn't occur. This is attributed to some particularities related to the IAB insertion and operation: In order to have a 20% increase in aortic pressure augmentation—e.g., for sufficient bowel and brain perfusion, a 'big'>34 mLs balloon is usually used. Unfortunately this also translates to a 2-3 mm diameter balloon catheter and an increased clinical risk of amputation due to femoral blood flow compromise. There is also a risk of aortic trauma and ischemic renal failure due to the whipping effect of the IAB upon the wall of the descending aorta, which has also been shown to induce intermittent flow blockage of the renal arteries. Those drawbacks have limited expansion of the clinical applicability of IAB and as a consequence, by weighing risks and benefits, IABs have been reserved mainly for ischemic heart disease patients.

3) Prior Art

Several attempts have been made, for instance in U.S. Pat. Nos. 4,522,195 and 4,785,795, to combine a pumping balloon with a valve system, most frequently a second balloon, as in U.S. Pat. No. 6,210,318, that acts like a valve operatively coupled to the main balloon. This second balloon achieves to some extent compartmentalization of the pressure augmentation effect of the main balloon, as it keeps the pressure effect on 'one desired side' of where the IAB resides. This approach 'halves' the demand for balloon volume (by achieving a better vacuum effect), augments the balloon pressure effect, decreases the demand for a big catheter tube that would be needed for a bigger balloon, and limits many of the drawbacks above. However additional problems with this approach do occur. For instance the second 'valve' balloon has to be very 'close' to the aorta in order to achieve flow occlusion, and has to be fluidically connected to the main balloon. This proximity along with the repetition of the second balloon's inflation/deflation occlusion cycles presumably results in significant wall trauma and thus it is not surprising that those approaches have not been successful yet in any clinical setting.

SUMMARY

The present invention relates to a system that achieves complete circulatory compartmentalization, and better circulatory assist, with smaller balloon volumes and smaller catheter size overcoming the drawbacks of the prior art mentioned above. When a pumping balloon deflates, this creates 'empty space' and generates flow towards the balloon. This 'vacuum effect' is particularly useful in the case where a congested and failing heart is unable to pump blood towards the aorta, thereby providing less blood to the brain and other vital organs. However, such in the case of the aorta and IAB, a large portion (>50%) of this vacuum effect may be lost due to the fact that the pumping balloon 'vacuums' flow not only from the upstream circulation, in the direction of expected circulation, but also from the downstream circulation, back towards the pumping balloon. Advantageously the system eliminates retrograde flow towards the balloon. This is mainly accomplished by combining the expandable frame portion with a unidirectional flow control or check valve which prevents flow from the downstream circulation towards the balloon, but allows downstream flow generation from the balloon.

The system is a transcutaneous flow assist system that is easily inserted and may be used to selectively augment, induce, or create flow in any branch of the circulation. Low flow conditions may occur in any part of the circulation, e.g., the arterial, venous, lymphatic, cerebrospinal, urinary, and biliary circulation. By way of example, low arterial flow is encountered in the clinical states of coronary artery disease and ischemic bowel. Low venous flow is encountered in varicose veins and lymphedema. Low urinary flow is seen in ureter obstruction. The system can be applied to all low flow conditions. However in the interest of simplicity, it will be described with reference to the arterial circulation and in particular the aorta, which is the most demanding system in terms of flows and pressure differentials that need to be met.

It is a particular aim to provide a pumping balloon which has no whipping effect on the aorta or any circulatory lumen wherein it resides. This is mainly accomplished by using expandable frame portions which position the pumping balloon in the center of the aorta. It thereby defines a certain distance between the balloon and the wall of said body channel, preventing trauma. This is particularly useful in the case where an IAB is to be placed in the Aortic Arch.

Another aim is to provide a simple circulatory assist system suitable for cases where there is a very specific demand for higher flows and pressures in a certain part of the circulation compared to others, such as in the renal arteries versus the femoral arteries. This is mainly accomplished by using an expandable valve system which operates in association with the pumping balloon and compartmentalizes the pressure and flow effect on demand.

BRIEF DESCRIPTION OF THE DRAWINGS

FIGS. 1a and 1b are schematic representations of a first embodiment of the system, before and after deployment of an expandable centering frame.

FIGS. 1c and 1d are schematic representations of a second embodiment of the system, before and after deployment of both a pumping balloon and an expandable centering frame. It will be understood that for sake of clarity FIG. 1a and other before-deployment illustrations do not attempt to show before-deployment balloon configuration, but will have a before-deployment balloon configuration similar to that shown in FIG. 1c.

FIGS. 1e and 1f, 1g and 1h, and 1i and 1j are schematic representations of other embodiments of the system, before and after deployment of expandable centering frames.

FIGS. 1n and 1o are schematic representations of manipulations used to sequentially expand a pair of distally-disposed expandable centering frames, and a proximally-disposed expandable centering frame, arranged to bracket a pumping balloon.

FIGS. 1 sub i through 1 sub ix are partial, detailed views of structures in the immediate vicinity of the expandable centering frames.

FIGS. 2a through 2c are side views of various expandable frame structures. FIG. 2a items ii, iii, iv and FIG. 2b item ii include corresponding end views of the illustrated structure.

FIGS. 4a and 4b, 5a through 5d, 6a and 6b, 7a and 7b, 8a and 8b, 9a and 9b, 10a and 10b, 11a and 11b, 12a through 12c, and 13a and 13b are schematic representations of exemplary and/or preferred embodiments and methods of using the system in exemplary intra-aortic assist applications.

FIG. 21 is a time sequence of expansion of an expandable frame including a preferred check valve construction.

FIG. 21 sub is a collection of perspective views of the preferred check valve construction in closed (a and b) and open (c) configurations.

DETAILED DESCRIPTION

Figure 1K:
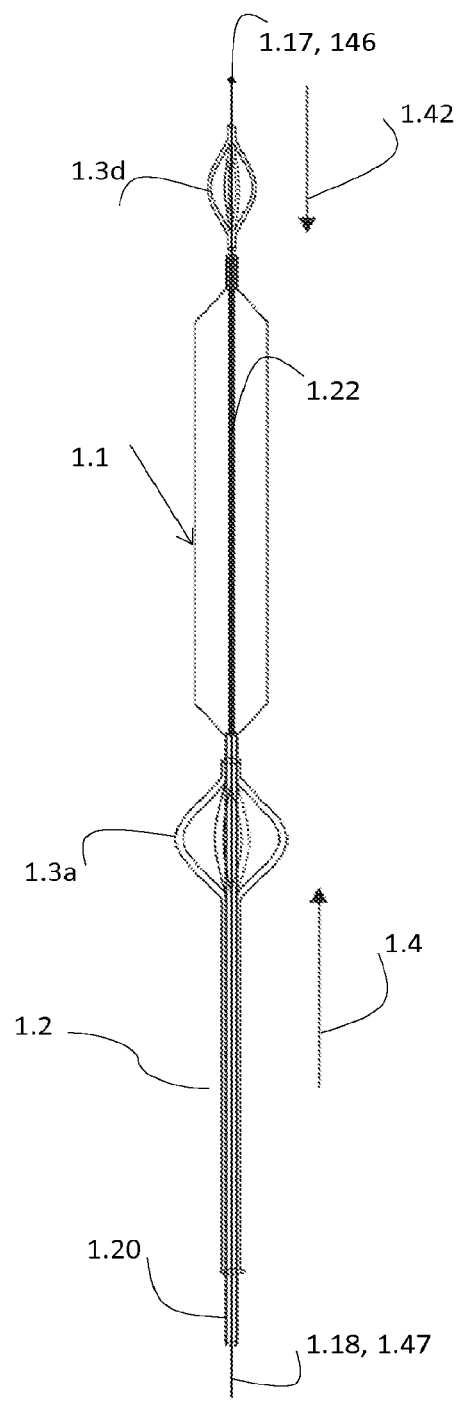
FIG. 1k is a schematic representation of manipulations used to independently expand a distally-disposed expandable centering frame and a proximally-disposed expandable centering frame bracketing a pumping balloon.

The present disclosure describes an advanced balloon pumping system that is able to provide one-way axial flow as well as circulatory compartmentalization and pressure differential in any circulatory lumen. It relies on the deployment of expandable centering frame (also referred to also as a stent) with valve members mounted thereupon. The term circulatory lumen refers mainly to the arterial system, the aorta and any peripheral vessel (such as the carotids) where flow augmentation may be demanded. However it is easily understood that the system can be used (without a demand for a gated counterpulsation function) in any other part of bodily fluid circulation, where either a one-way pumping system or a one-way 'draining system' is necessary (any arterial, any venous, biliary, urinary, lymphatic, or cerebrospinal circulatory lumen). For reasons of simplicity the balloon pumping system is specifically described with reference to the aorta.

The implanted portion is introduced percutaneously in the desired circulatory lumen using the Seldinger technique. The desired vessel or cavity is punctured with a sharp hollow needle, with ultrasound guidance if necessary. A round-tipped guidewire is then advanced through the lumen of the needle and directed actinoscopically to the desired site within the vessel or cavity. A balloon hollow catheter continuously accessible from its proximal end, incorporating one or more wrapped around balloons positioned proximate the expandable centering frame and/or valve members fitting the diameter and length of the target circulatory lumen, is passed over the guidewire and advanced into the cavity or vessel until its desired position is confirmed via fluoroscopy. Sleeve tubes and other operating means described herein may be used to deploy, collapse, manoeuvre and allocate the device to the desired position. Injection of radiocontrast may be used to visualize organs and the device's relative placement. The guidewire is withdrawn and the balloon catheter is connected to an external balloon pump operating in phased relationship to the body channel's flow stream.

The balloon system provides efficient flow to a desired distal site or to a specific compartment of the vasculature due to its capacity upon deployment to separate completely one vascular chamber from the next. It integrates radially expandable frame or stent members having valve members mounted thereon, and is able to create alternating input and output flow by respectively alternating pressure differentials induced by the balloon's inflation and deflation. The radially expandable members are constructed in such way so as to achieve accurate, generally central balloon spacing to prevent balloon/vessel wall contact, eliminating whipping effects (during inflation) and passive movement of the vessel wall towards the collapsing balloon (during deflation). This allows placement into small vessels as well as longer balloon structures. As a result, the balloon's diameter and displacement volume can be larger compared to previous balloon pumping systems, and thereby capable of creating respectively higher pressure gradients during its operation.

To achieve aims of the invention a non-flow occlusive, and preferably reversibly collapsible, expandable frame is integrated on the balloon catheter. One or more expandable frames may be used simultaneously. In order to eliminate undue overexpansion, the frame may be constructed so as to provide either certain expansion to a predetermined final diameter, or a progressive, controlled radial expansion, dependent on the elastic resistance of the surrounding circulatory lumen. In the latter the dilatation may be interrupted and resumed to reach a variety of diameters. It is desirable for the expanding system to maintain efficient valvular function in any intermediate diameter. An impedance measuring mechanism may also be provided that may be connected to an electronic interface for continuous display. In certain embodiments the dilating element of the balloon system may additionally act as a prosthesis or stent to maintain the diameter of the circulatory lumen above a desired size.

The pumping balloon includes a catheter-mounted balloon, made of non-stretchable plastic material, having a distal tip and a proximal end. The balloon may be made of the same plastic material angioplasty balloons and/or intra-aortic balloons are manufactured, i.e., PVC, nylon, polyurethane, polyethylene, polyethylene terephthalate (PET), cross linked polyethylene, or the like. The selection of the material depends upon the size of the balloon. Bigger balloons demand higher pressures of operation and accordingly a more resistant material. The diameter range is typically from 6 mm up to 30 mm and may reach 100% of the circulation lumen's rest diameter if frame-restrained (contained within a frame or stent structure). If not restrained, the diameter shouldn't exceed 90% of the vessel's diameter in order to avoid wall trauma during the balloon's inflation.

The catheter tube has a distal end joined via a traditional technique (e.g. welded, molded or adhered with adhesive, or any other method suitable for joining the edges of two plastic portions) to the balloon's proximal end, and a proximal end extending freely outside of the body, connected to an external balloon pump and receiving positive and negative pressure pulses for the balloon's inflation and deflation. The catheter tube is preferably made of polyethylene, although any other biocompatible material used for medical tubes, i.e., PVC, urethanes, polypropylene, polycarbonate, silicone, ABS, Pebax™, Hytrel™, C-Flex™, Texin™, Tecoflex™ can be used. Alternatively a superelastic metal alloy, such as nitinol, may be used. The catheter tube may have a single lumen (operating one balloon), or multiple lumens (based upon the number of balloons and pressure sensors used).

The expandable centering frame described above comprises at least one, and preferably a plurality of, malecot-type frame or stent members. Each such member may comprise a collapsible, radially expandable member, having a proximal and a distal portion connected to a slidable tubular shaft as well as a middle portion which distorts outward upon selective movement of the slidable shaft (either proximal movement of a distal shaft portion connected to the distal member portion, or distal movement of a proximal shaft portion connected to the proximal shaft portion). The distal portion, proximal portion, and middle portion comprise a series of living hinges causing the member to expand outwardly in a predetermined manner. The member is at least partially pretreated to obtain such a configuration upon expansion, adapted to fit, and at least partially conforming to the generally cylindrical shape of said circulatory lumen and its asymmetric portions or path, if any.

Figure 2A:
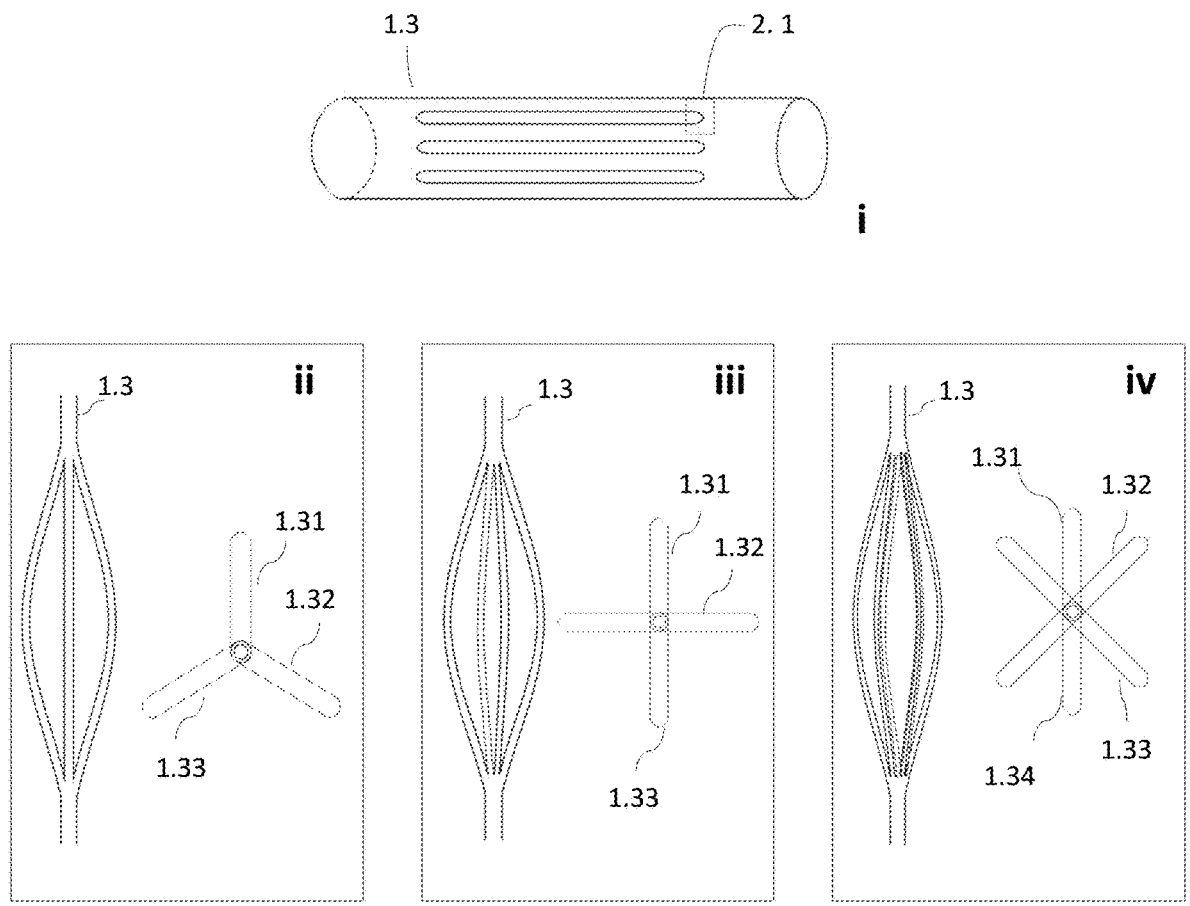
Figure 2C:
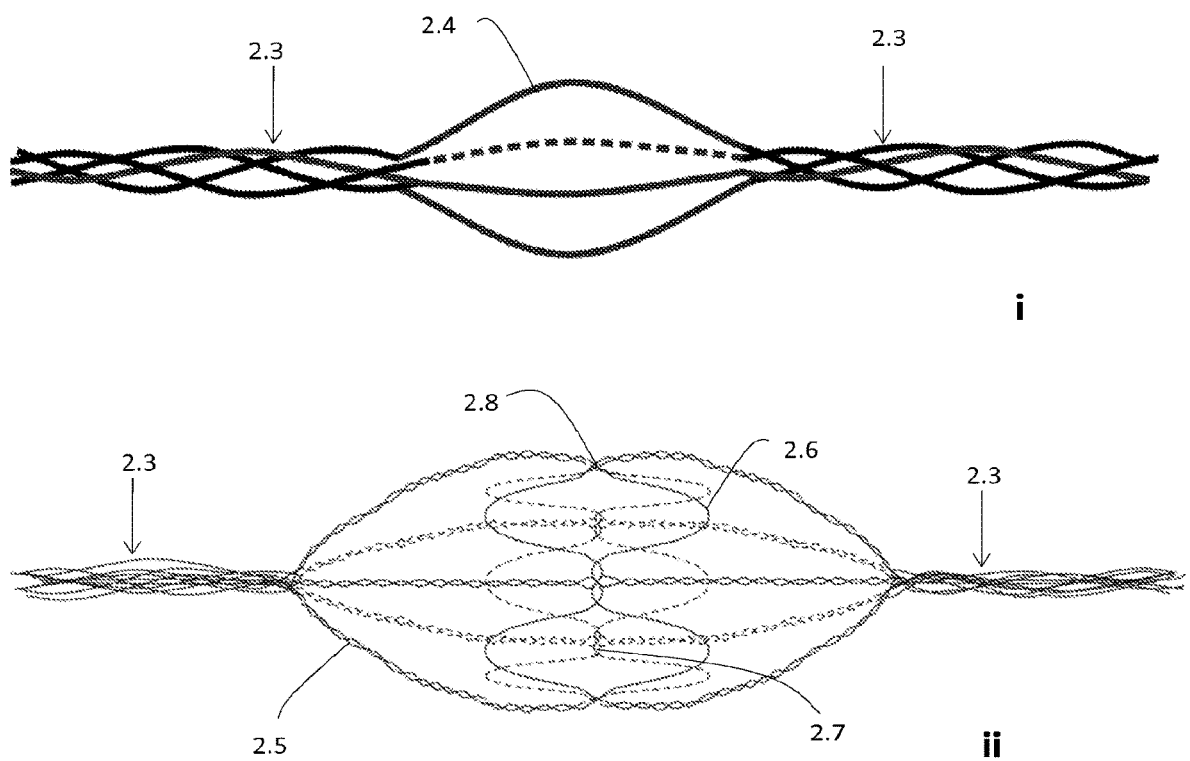
Figure 3:
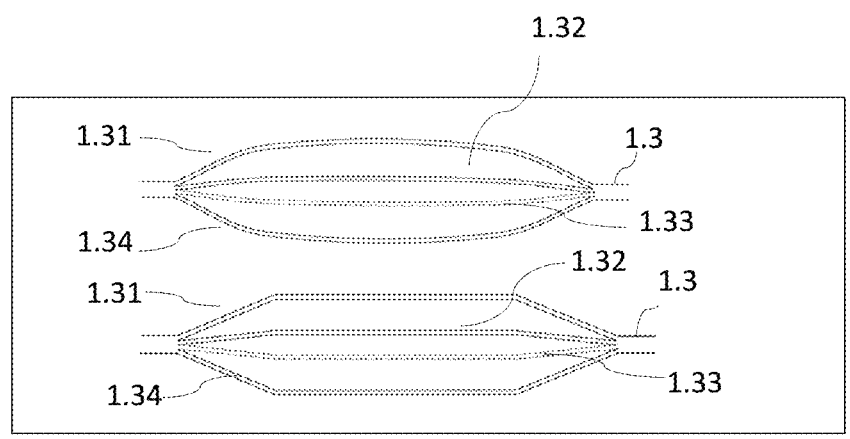
FIG. 3 is a schematic representation of a pair of expandable frames formed or pretreated to have an elongated, cage-like shape upon expansion/deployment.

The expandable frame may alternately comprise a slit tube, a tubular braid, a mesh or a twist of superelastic filaments (wires or tubes) or any combinations thereof. Typically the engineering principle is that a proximal, non-expandable tubular shaft portion supplies at least one radially expandable member, such as a frame arm, strut, stent arm, etc. which diverges at its origin in the proximal shaft portion and converges again at its end in a distal shaft portion to reform a distally-extending, non-expandable tubular shaft portion. FIG. 2a depicts exemplary lateral and superior views of slit tubes having 3 (ii), 4 (iii) and 6 (iv) radially expandable members 1.31, 1.32, 1.33, 1.34, etc. Different heat-set tooling can produce any kind of three dimensional structure (e.g., FIG. 3), ellipsoidal, ellipsoid hyperboloid, ovoid, trapezoid, spherical, disciform or any combination thereof, depending on the interior of the surface that needs to be conformed with. For example ellipsoid paraboloidal is particularly useful in cases where a stent member needs to conform to a central smaller diameter. If certain areas of the members need to be more compliant this can be achieved by a number of methods: smaller member thickness in certain areas (FIG. 2a, 2.1), smaller slits or larger member widths in certain areas (FIG. 2b, 2.2), localized electropolishing, localized etching or by using more elastic filaments in some areas compared to others. The longitudinal member sizes, strengths and lengths are selected so as to able to sustain and if necessary oppose the elastic recoil applied on the frame or stent from the surrounding tissue. They may have the same length in order to be able to collapse completely and expand symmetrically. They may be either the strips of a slit tube, or single tubes, wires, or narrow meshes, or twists or braids of superelastic monofilaments attached to tubular portions. The members of multi-part frames or stents may be attached by adhesive, solder, spot welding, brazing, crimping, welding or any other joining method suitable for joining the edges of an intravascular stent. Wire twists, braids and mesh combinations need not to have a low flow profile upon expansion in order to allow the bodily fluid to flow through. But as a general rule the members (strips, wires or tubes) have a low flow profile between the points of the minimum and maximum diameter of the device, i.e., between the diameters of collapsed and fully deployed stage. FIG. 2c shows two exemplary stent members (i) and (ii) comprising wire twists in deployment status. The monofilaments comprising the struts remain perplexed as they diverge from their proximal tubular portion 2.3, split into single filaments 2.4 or smaller filament groups 2.5 to form the middle (or expandable) portion, and converge again to reform or connect to the distal tubular portions 2.3. FIG. 2c (i) and (ii) show exemplary wire twist stent members.

FIGS. 1a through 1o show embodiments in which frames 1.3 are expanded in conjunction with deployment of a pumping balloon 1.1 carried by the balloon catheter 1.20. The frames will be described in relation to the balloon 1.1 as proximal if they are positioned more toward the catheter end extending freely outside of the body, and distal if they are positioned more toward the catheter end positioned within the circulation limen. They are further divided to upper (more distal) and lower (more proximal), when more than one proximal or distal stent members are described.

Proximal Frame or Stent Member

In FIGS. 1a and 1b, a proximal expandable frame 1.3 is delivered in a collapsed state, mounted on an elongated shaft 1.2. The expandable frame 1.3 comprises the distal portion of the shaft, which is advanced through the balloon's insertion site and operated from out of the body, surrounding the balloon catheter 1.20. The shaft is inserted separately to the balloon and pushed against a stopping element 1.86 that surrounds the balloon catheter 1.20; the expandable frame 1.3 is pretreated, heat set, and biased to obtain an ellipsoid configuration upon expansion, and thus longitudinal sliding 1.4 is transformed to radial expansion (FIG. 1b). The stopping element 1.86 may be as simple as a widened balloon catheter portion with a diameter slightly larger to the outer surface of the shaft 1.2 or a small caliber, hollow tube fixed onto the desired position of the balloon catheter 1.20. The shaft may comprise a hollow tube made from a reasonably flexible biocompatible plastic material or a metal superelastic material such as Nitinol alloy S. Examples of such plastic materials are biocompatible polypropylene, polyethylene, PVC, silicone, polyurethane, polystyrene and combinations thereof. A sleeve tube (FIG. 1 sub i, 1.87) having an inner diameter larger than the outer diameter of the expandable frame 1.3, may be used to reduce the flow profile of the shaft and stent member during insertion.

The applied force/longitudinal shortening (F/dL) relationship curve may be continuously monitored using an electronic interface connected to an external control handle and a potentiometer applying the force to the proximal portion for the sliding of the shaft 1.2. The interface may display continuously in a graphical or numerical manner the applied force for a given longitudinal motion, and the zero point may be the moment the shaft 1.2 reaches the stopping element 1.86. The inventors have determined that there is a curve point where more force is needed to achieve more expansion and this is may be different for each stent member size and circulation lumen. An electronic automatic system may be used to apply longitudinal force and detect substantial deviation from the relationship curve indicating contact between the expandable frame and the walls of the vessel or cavity, allowing expansion up to contact or a maximum desired diameter. Alternately gradation markers and indices reflecting the actual diameter of the stent member may be printed upon the balloon catheter portion 1.20, where the proximal portion of the shaft is rested outside of the body, so as the operator to be aware of the expanded diameter. Given the fact that the rough target diameter is known, manual opening up to a predetermined diameter may be used in cases where the circulation lumen wall is able to sustain small expansion force without significant risk for perforation.

The balloon tip 1.23 is here shown to include a lumen 1.22 that runs through the balloon's entire length. This lumen, which is often described a pressure sensor tube, is known to those familiar with the art. The standard design of an IAB incorporates a balloon catheter 1.20 that carries gas in and out of a balloon 1.1 attached to it at a proximal junction point 1.21. Within the balloon catheter 1.20 there is usually a second lumen (shown as 1.22) that originates at the proximal end of the balloon catheter, courses the entire length of the balloon catheter and actual balloon up to the balloon tip 1.23. At the balloon tip 1.23 this second lumen 1.22 gains access to the circulation. The operator of the balloon can connect the proximal end of this second lumen 1.22 to a pressure sensor and measure the pressure at the tip 1.23. For this reason this second lumen is commonly referred to as "pressure line" or "pressure sensor line" or "pressure tube". During the percutaneous insertion of an IAB this second lumen, or any other lumen of a multi lumen balloon catheter 1.20, is also routinely used to thread a guiding wire. In devices which do not require a pressure sensor, a lumen like a pressure-sensor lumen is still provided to support the balloon 1.1 along its length and prevent longitudinal folding of the balloon during inflation/deflation, as well as to provide a path for a guiding wire. For simplicity we will refer to both lumens as intra-balloon lumens 1.22, where pressure sensing may or may not be provided in some implementations of the apparatus.

FIGS. 1c and d show a variation of the system shown in FIGS. 1a and 1b. The expandable frame 1.3 has its distal shaft portion 1.77 joined to the exterior of the balloon catheter 1.20 at a desired position. Preferred joining methods are welding, molding, adherence with glue, or any other method suitable for joining the edges of two plastic portions or plastic/metal portions, or metal portions. The expandable frame 1.3 is pretreated, heat set, biased to obtain an ellipsoid configuration upon expansion, conforming the interior of the body channel. The final diameter may be either achieved passively, automatically upon release of the shaft 1.2, being the natural heat set position upon release of the shaft, or be subsequent to active longitudinal sliding of the shaft.

FIG. 1 sub ii corresponds to the addition of a sleeve tube 1.87 that may be used to keep the expandable frame restrained to reduce the device's profile and facilitate insertion. In FIG. 1 sub iii the balloon catheter 1.20 incorporates a stopping element 1.79 positioned within the expandable frame 1.3 so that it becomes abutted against the proximal shaft portion of the expandable frame 1.3 to prevent excessive travel thereof and limit expansion to a predetermined diameter.

FIGS. 1e and f show another variation of the system. The expandable frame 1.3 has its distal shaft portion 1.77 joined to the balloon catheter 1.20 and is heat set to deploy spontaneously to a predetermined diameter, with deployment controlled via operating wire(s) 1.18 attached or joined to the proximal portion thereof. An intermediate diameter can be achieved by pulling or releasing the wire. As shown in FIG. 1 sub iv, the operating wire is ideally run through a lumen of a multi-lumen balloon catheter 1.20, or external hollow tubes attached upon a single lumen balloon catheter, having its proximal end outside the body operated by the user and its distal end attached to the proximal shaft portion of the expandable frame 1.3. A variety of intermediate diameters can be produced by pulling or releasing the operating wire(s) 1.18. The expandable frame 1.3 is completely expanded when the operating wire 1.18 is inserted (if manually expanded) or released (if self-expanding) and completely collapsed when the operating wire is pulled. A sleeve tube 1.87 or a similar sleeve tube not extending over the expandable frame 1.3 may extend outside the body, preferably proximate the proximal end, to create the multi-lumen structure. FIG. 1 sub iv and FIG. 1 sub v show the sleeve tube 1.87 and stopping element 1.79 variations mentioned before.

Distal Frame or Stent Member; Balloon Tip

FIGS. 1g and 1h represent another preferred embodiment. An expandable frame 1.3 is mounted on a segment 1.24 extending distally from the pumping balloon, e.g. a balloon tip portion 1.23 connected to an intra-balloon lumen 1.22, or an inter-balloon catheter portion (described further below and shown in FIGS. 13a, 13b, and 20. Both comprise hollow tube portions (one lumen or multi-lumen), positioned distally in relation to at least one inflatable balloon 1.1, and are structurally similar to the lumen of the balloon catheter 1.20. The segment 1.24 has defined proximal and distal end portions, in terms of proximity to the balloon or insertion site, and may accommodate at least one expandable frame 1.3. It has an outer diameter smaller than the inner diameter of the expandable frame 1.3 and a length sufficient to accommodate the expandable frame 1.3 in the collapsed state. Here the different modes of expansion will be described with reference to a terminal balloon tip portion, however the same ones apply also to the inter-balloon catheter portions.

The expandable frame 1.3 has its proximal shaft portion 1.80 joined to the balloon tip 1.23 and/or segment 1.24, with its distal shaft portion 1.77 free to move about and to reversibly slide along the axis of the segment, between a collapsed (FIG. 1g) and deployed (FIG. 1h) configuration. The intra-balloon lumen 1.22 is shown to accommodate a linearly movable operating member 1.18, with an outer diameter smaller than the inner diameter of the intra-balloon lumen. The operating member 1.18 may comprise a linearly movable operating wire or tube (FIG. 1l, 1m) which may have a widened end forming, or otherwise be joined to, an end-cap 1.17. The end cap 1.17 is operatively coupled to the distal end of the expandable frame 1.3 for deployment. The operating member 1.18 may be made from a reasonably flexible biocompatible plastic material or a metal elastic material, preferably superelastic such as Nitinol alloy S. Examples of such plastic materials are biocompatible polypropylene, polyethylene, PVC, silicone, polyurethane, polystyrene and combinations thereof. The end cap 1.17 is shown to have a diameter larger than the inner diameter of the expandable frame's distal shaft portion 1.77 in order to engage with it and induce expansion upon pulling. Alternatively the operating wire 1.18 may be fixed to the distal shaft portion of the expandable frame. Preferred joining methods are welding, molding, adherence with glue, or any other method suitable for joining the edges of two plastic portions or plastic/metal portions or metal portions.

The incorporation of an expandable frame 1.3 at the distal end of the apparatus poses a challenge to bending during percutaneous insertion. To address this, a sleeve tube 1.87 (FIG. 1 sub vi) having an inner diameter larger than the outer diameter of the expandable frame 1.3 and collapsed pumping balloon 1.1 may be used to reduce the flow profile of the expandable frame and pumping balloon during insertion. FIG. 1 sub vi and FIG. 1 sub vii show the sleeve tube 1.87 and stopping element 1.79 variations mentioned before, however in this and similar embodiments the stopping element is positioned within the expandable frame 1.3 so that it becomes abutted against the distal shaft portion of the expandable frame 1.3 to prevent excessive travel thereof and limit expansion to a predetermined diameter.

Figure 1L:
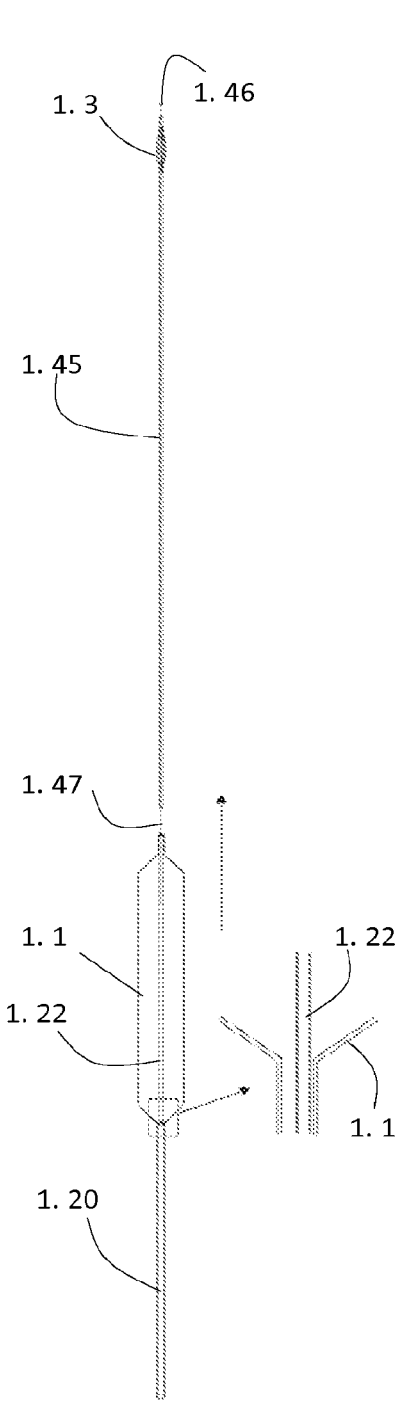
FIGS. 1l and 1m are schematic representations of a sequence in which a distal expandable frame, mounted upon a flexible and hollow elongated shaft 1.45, is threaded onto an emplaced guidewire, and IAB-like apparatus is advanced along the shaft 1.45 to assemble the implanted portion of the apparatus in situ.
Figure 1M:
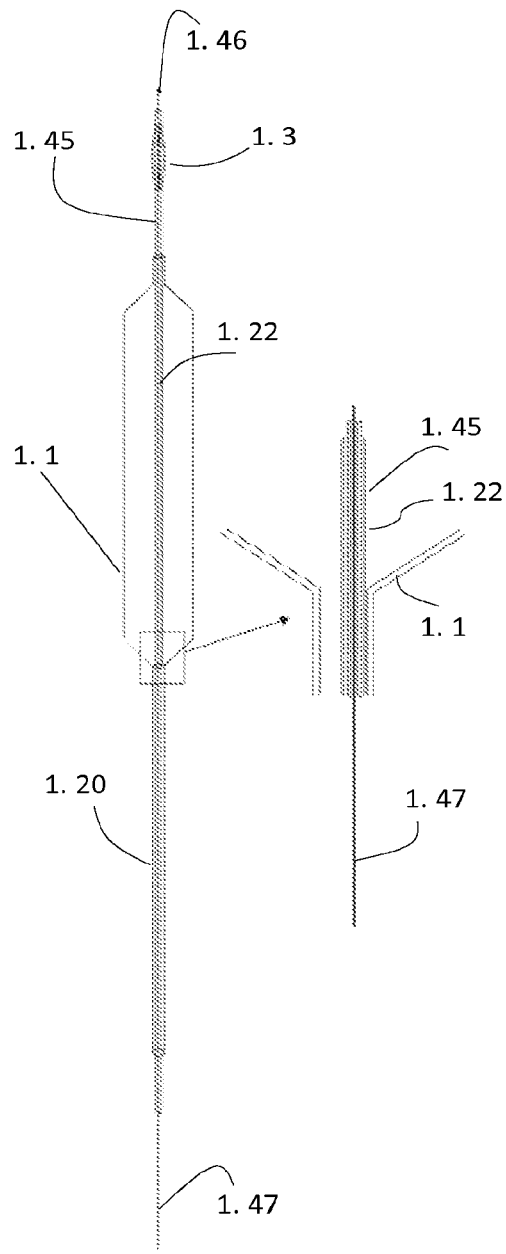

In a preferred subembodiment and method, shown in FIGS. 1l and 1m, the balloon apparatus is shown being assembled in a step wise manner at the operation site, having its distally positioned, expandable frame 1.3 separate from the balloon 1.1 and balloon catheter 1.20. Initially, according to the Seldinger technique, a transcutaneous hollow needle provides access to the circulation lumen, or a channel communicating to it; a guiding wire 1.47 is fed through the needle and advanced to the operation site. The needle is removed whilst the guiding wire remains in situ. Subsequently a hollow elongated shaft 1.45, integrating the expandable frame 1.3 at its distal end, is inserted through the puncture site, advances and slides over the guiding wire until it is delivered to the operation site. Finally the pumping balloon 1.1 is positioned by sliding it down the elongated shaft 1.45 after threading the elongated shaft through the intra-balloon lumen 1.22 (and, if the intra-balloon lumen is not contiguous to the outside of the body, with a non-gas-pumping lumen of a multi-lumen balloon catheter 1.20). Both the shaft 1.45 integrating the expandable frame 1.3 and the balloon 1.1/balloon catheter 1.20 combination have sufficient lengths so as to be accessible from outside the body. One the balloon 1.1 is at the operation site the expandable frame 1.3 is expanded. This assembly method provides a great advantage: if the expandable frame 1.3 includes a check valve, occlusion device, or other function-enhancing structure, that may increase the diameter of the expandable frame to such an extent that it cannot be threaded through an intra-balloon lumen 1.22. In these cases this method of insertion and assembly is preferable.

Two expansion methods of the expandable frame 1.3, an induced-one and a self-expanding one, will be described. In one preferred method, shown FIG. 1*l*, the elongate hollow shaft 1.45, integrating the expandable frame 1.3, is slid over guiding wire 1.47 and pushed against a stopping element 1.46, and thus forced to expand. By stopping element in this case is meant a widened end of the guiding wire 1.47 or an end cap joined to the end of the guiding wire. The expandable frame 1.3 is pretreated and heat set, to obtain a biased ellipsoid configuration upon expansion. The inner diameter of the expandable frame 1.3 is less than the outer diameter of the stopping element 1.46. The shaft 1.45 is advanced through the balloon's insertion site, surrounding the guiding wire 1.47, and operated from outside of the body. A sleeve tube may be used to facilitate insertion of the shaft 1.45 and to restrain the integrated expandable frame 1.3 from deploying. Upon reaching the stopping element 1.46, further longitudinal sliding toward the stopping element is transformed to radial expansion of the expandable frame 1.3.

Alternatively the widened end of the guiding wire 1.47 and the elongate hollow shaft 1.45 may be fixed together at their distal ends and advanced to the operation site as a unit. Preferred joint methods are welding, molding, crimping, adherence with glue, or any other method suitable for joining the edges of two plastic portions or plastic/metal portions, or metal portions. The hollow shaft 1.45, operated from outside the body, slides freely over the guiding wire 1.47 and the expandable frame 1.3 expands when pushed against the fixed-together ends.

In another preferred method, the expandable frame 1.3 on the elongated hollow shaft is pretreated to deploy to a predetermined desired diameter. As with the first preferred method, the distal ends of the hollow shaft 1.45 and guiding wire 1.47 may slide freely to be fixed together. An outer sleeve tube 1.87, like that shown in FIG. 1 sub ii, may be manipulated for delivery and deployment control. The outer sleeve tube 1.87 has an inner diameter larger than the outer diameter of the expandable frame 1.3 and elongate shaft 1.45 (substituting for the balloon catheter 1.20 of the cited figure). The elongate shaft and sleeve tube are hollow structures comprising of a reasonably flexible biocompatible plastic material or a metal material, preferably superelastic Nitinol, such as Nitinol alloy S. Examples of plastic materials are biocompatible polypropylene, polyethylene, PVC, silicone, polyurethane, polystyrene and combinations thereof. Additionally, if the intra-balloon lumen 1.22 has an inner diameter larger than the outer diameter of the expandable frame 1.3 and elongate shaft 1.45, during removal of the balloon apparatus the intra-balloon lumen may be used as a sleeve tube. Relative manipulation of the elongate shaft 1.45 and balloon 1.1/balloon catheter 1.20 combination can cause the intra-balloon lumen 1.22 to slide over the expandable frame 1.3 and collapse it to facilitate removal of the system. The stopping element 1.46 may again be a widened end of the guiding wire 1.47 or an end cap joined to the end of the guiding wire. In either case, for either of the above methods, the stopping element 1.46 needs to have a sufficiently small diameter to threat through a needle or obturator during percutaneous insertion.

FIGS. 1*i* and 1*j* show to an exemplary embodiment with two distal expandable frames, 1.3*a* and 1.3*b*, fixed on the balloon tip portion 1.24 of a pumping balloon 1.1, following induced expansion. The expandable frames are initially in the collapsed state, but pretreated to acquire a biased shape upon expansion. Pulling of the guiding wire 1.47, abuts a stopping element 1.46 against the upper or distal-most expandable frame 1.3*a*, which is induced both to expand and slide towards the balloon tip 1.23. The latter longitudinal motion abuts the upper expandable frame 1.3*a* against the lower expandable frame 1.3*b*, which is eventually also forced to expand. The final diameter of each stent member can be predetermined by incorporating stopping elements 1.79 like those described earlier on the balloon tip portion 1.24.

FIG. 1*k* depicts an exemplary combination of distal and proximal expandable frames 1.3. Each one can be separately controllable as described above, being self-expandable or induced-expandable. In this illustrated embodiment the proximal expandable frame 1.3*c* is integrated in a hollow shaft 1.2 and forced to expand due to the longitudinal sliding 1.4 of the shaft with respect to the balloon catheter 1.20. The distal expandable frame 1.3*d* is in an initial collapsed state and forced to expand due to longitudinal pulling 1.42 of the operating member 1.18 or guiding wire 1.47, in accordance with the alternatives described above. The distant expandable frame 1.3*d* is fixed on the balloon's tip 1.23 and traction of the member or wire engages the respective stopping element 1.17 or 1.46 with the distal shaft portion of the expandable frame, forcing it to expand.

FIGS. 1*n* and 10 show a preferred controlled expansion combination of two distal expandable frames 1.3*a* and 1.3*b* and a proximal expandable frame 1.3*c* mounted upon a balloon apparatus on either side of a pumping balloon 1.1. All stent members 1.3*a*, 1.3*b* and 1.3*c* comprise self-expanding frames predetermined to expand up to a desired diameter. They are delivered in a collapsed state, FIG. 1*n*, and they are restrained by a sleeve tube 1.51. The expandable frames have their proximal portions 1.81 joined to a balloon tip portion 1.24, whereas their distal ends are free to slide along the balloon tip portion 1.24. Controlled and reversible expansion is achieved by withdrawal 1.57 of the surrounding sleeve tube 1.51. Stopping elements 1.79, shown in FIG. 1 sub viii and FIG. 1 sub ix and described above, may be included to limit expansion to desired predetermined diameter.

FIGS. 4-20 illustrate various general apparatus configurations and applications. It will be understood that the devices discussed below may include some or all of the features and details discussed above, in any appropriate combination, but are being discussed at a high level of generality for the convenience of the now-informed reader. In general, the expandable frames discussed may lack any check valve or occlusion device feature, serving only to center adjoining portions of the apparatus, or may include a check valve feature providing unidirectional flow for the purposes described herein, or may include a occlusion device feature serving at least in part to compartmentalize or partition flow and pressure assist as described herein. Thus it will be understood that embodiments like those shown in FIGS. 1*a* through 1*o* may be used in applications like those shown, e.g., in FIGS. 4*a* and 4*b* and 5*a* and 5*b*, with expandable frames providing only catering/anti-whipping features if retrograde flow prevention, compartmentalization, etc. are either unnecessary or undesired. In the subsequent discussion and referenced figures, similar "point numbers," e.g., 1.1, 2.1, 3.1 . . . X.1, refer to similar anatomical or apparatus structures, and different "major numbers," e.g., 4.X, 5.X, 6.X, etc., indicate different exemplary embodiments or applications.

Exemplary Embodiments and Applications

FIGS. 4a and 4b show views of an exemplary IAB embodiment, combining an IAB including a pumping balloon 4.1 carried by a balloon catheter 4.9 with a proximal expandable frame 4.2 including a distally-opening check valve 4.5. It is inserted through the aortic cannulation site 4.3, into the aorta 4.8, during Cardiopulmonary By-Pass (CPB). The IAB may operate either in counterpulsation mode, gated with a pulsatile CPB pump, or non-gated in internal pacing mode, combined with a continuous flow CPB pump, to provide pressure assist to the lower aorta 4.10, the renal arteries 4.6, and other peripheral arterial flows. The proximal end of the balloon catheter 4.9 remains outside the body.

An important advantage of the system is that can be used to increase the blood pressure and flow in any part of the circulation during CPB (celiac arteries, carotids, renal arteries, etc.). In this case it is used to augment pressure and flow in the renal arteries 4.6 through operation of a proximal, passive, and distally-opening unidirectional valve, preventing upstream flow (opposite to CPB flow) as shown.

The valve 4.5 opens and closes periodically in conjunction with the balloon pumping. The valve opens (FIG. 4b) when downstream flow originating from the CPB forces the leaflets 4.5a, 4.5b, etc. to open, and vice versa closes (FIG. 4a) when pressure and upstream flow originating from the balloon's pumping exceeds the blood pressure 4.7 on the proximal side of the valve.

The exact positioning of the expandable frame 4.2 in relation with the renal arteries 4.6 remains to be ascertained. However it is anticipated that: the best position of the expandable frame 4.5 will be 4-5 cm upstream from the renal arteries, and the best position for the distal end of the balloon is likely 1-2 cm below the renal arteries. These help both to minimize retrograde flow from the renal arteries during the balloon's deflation, and to optimize blood pooling and flow towards the renal arteries without balloon itself impeding the flow.

Advantageously this application is expected to reduce dramatically the size of the balloon 4.1 and subsequently the size of the balloon catheter 4.9 needed to achieve the same pressure effect in the renal arteries in comparison with the current conventional IAB.

Figure 5A:
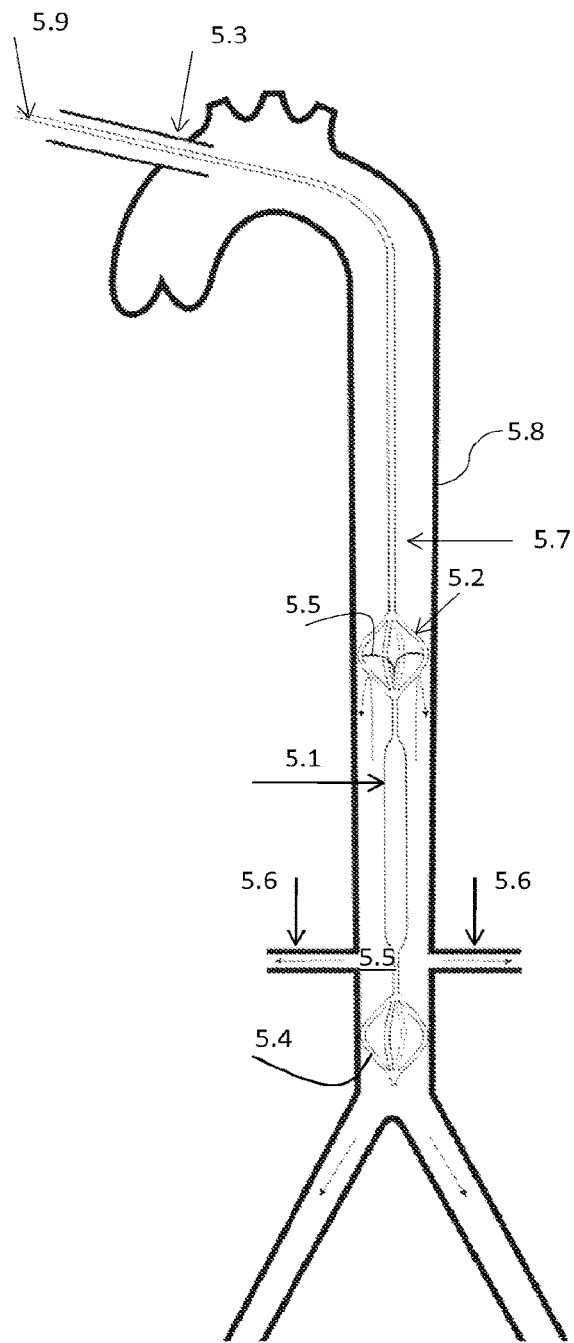
Figure 5B:
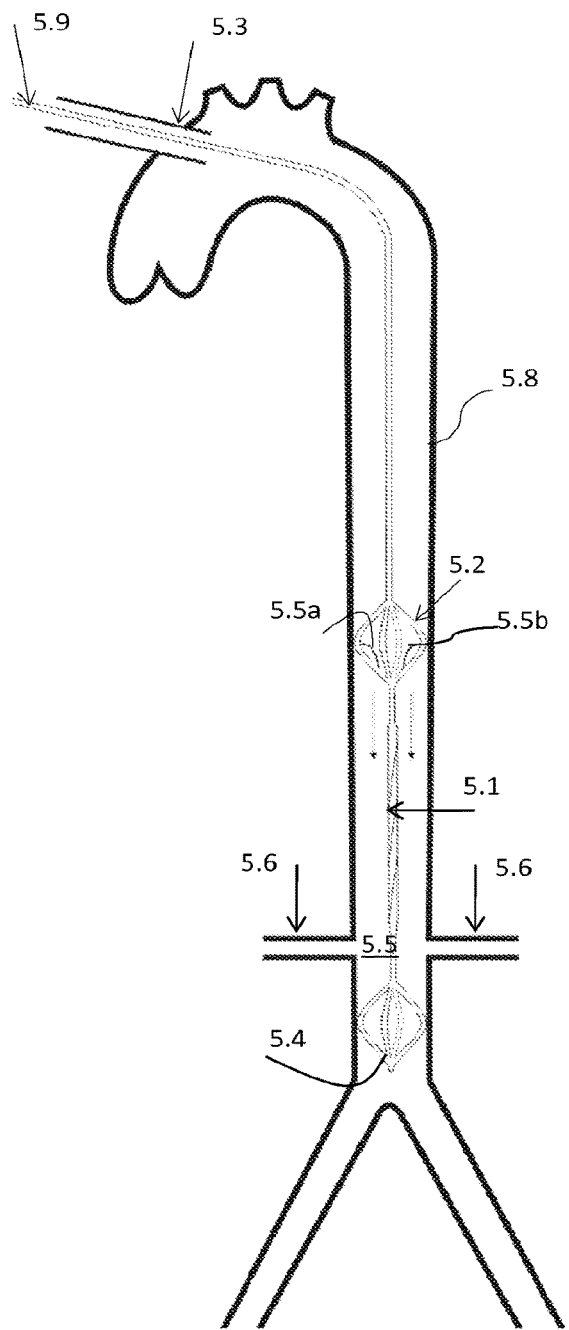
Figures 5C, 5D:
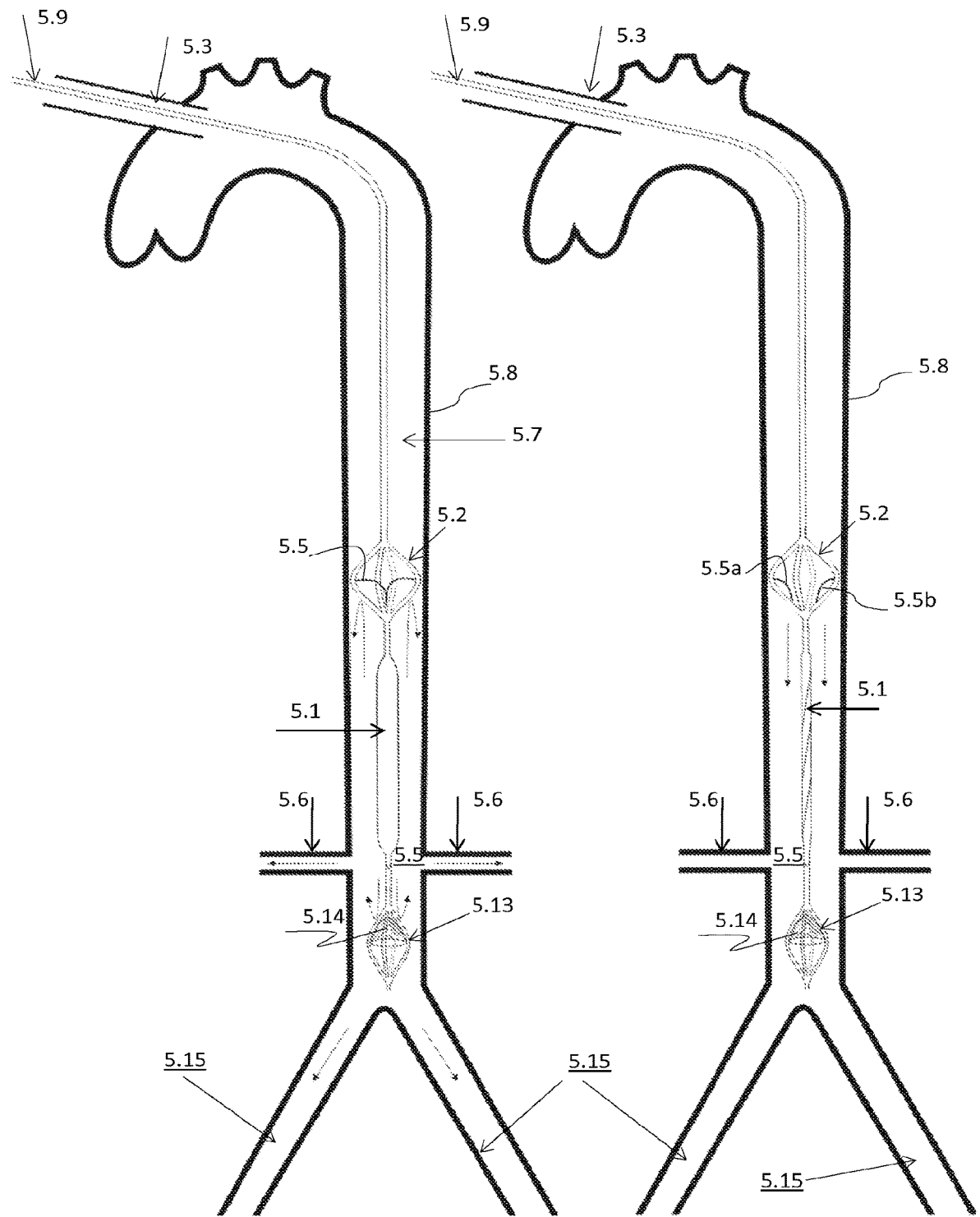

FIGS. 5a and 5b depict another exemplary or preferred embodiment. It integrates an additional, distal expandable frame 5.4 for better centering and fixing of a 'renal' IAB. The distal expandable frame 5.4, when fully expanded, can be used solely to space the balloon 5.1 in the center of the abdominal aorta 5.8, thereby avoiding balloon-to-wall contact. In FIGS. 5c and 5d variant-embodiments the expandable frame 5.3 is shown to integrate occlusion device 5.14, such as a membrane attached to the inner surface 5.13, or any portion thereof, of the frame members. This membrane 5.14 is made of a biocompatible material (such us TEFLON, DACRON, polyethylene, polyamide, nylon, polyurethane, natural rubber, synthetic rubber, thermoplastic elastomer or thermoset polymer and the like) with anti-thrombotic properties. Expansion of the distal expandable frame 5.4 induces a twofold advantage: 1. a partial downstream flow obstruction which augments retrograde flow to the renal arteries 5.6 and 2. a prevention of retrograde flow from more peripheral sites 5.15 which reduces 'steal phenomenon' from the periphery thereby increasing blood flow in the lower aorta 5.10 between the respective expandable frames 5.2 and 5.4. The latter contribution maximizes the induced pressure and flow effect of the balloon 5.1 in the aortic portion where the renal arteries 5.6 originate.

It is important to mention that instead of a membrane the distal expandable frame 5.4 could combine with any other occlusion device. An inflatable occlusion balloon, of a diameter between 0.5-2.5 cm, residing within, below, or above the distal expandable frame 5.4, would occlude partially the downstream flow and serve equally the same purposes of an occlusion device, thereby localizing and maximizing the pressure and flow effect between this valve/balloon and the proximal expandable frame 5.2.

Figure 5E:
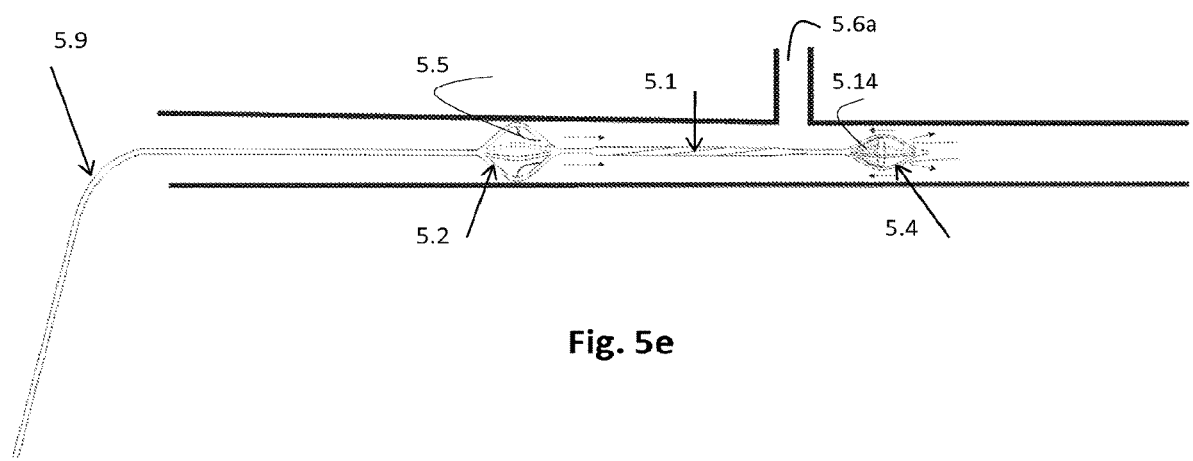
FIGS. 5e and 5f, 14a and 14b, and 15a and 15b are schematic representations of exemplary and/or preferred embodiments and methods of using the system in branch or peripheral arteries.
Figure 5F:
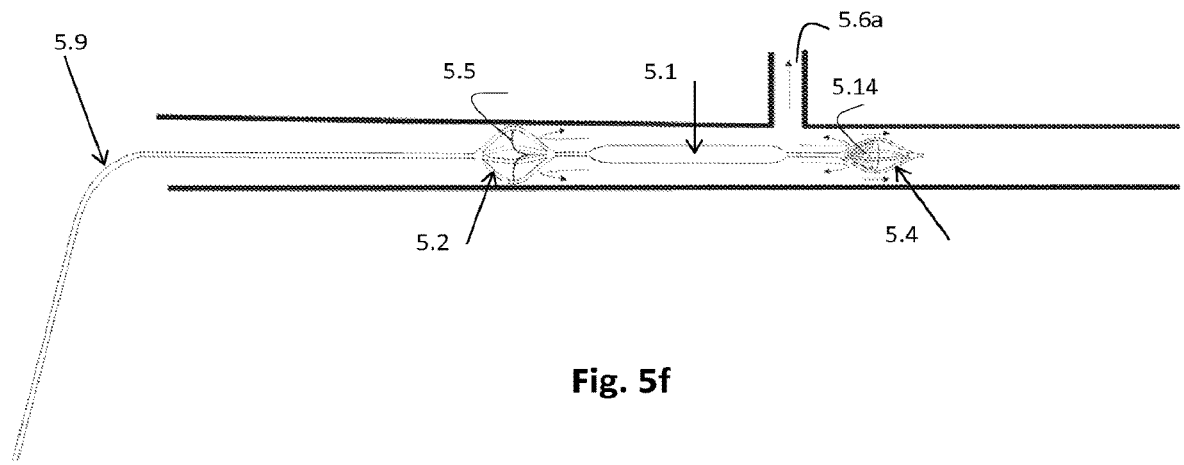

This same apparatus, in a smaller version, is particularly useful in the cases where a cerebral artery is ruptured in the course of a bleeding stroke. In those cases selective lateral branch augmentation perfusion, analogous to selective perfusion of the renal arteries 5.6, is likely warranted to compensate the lack of perfusion via collateral vascular routes. As shown in FIGS. 5e and 5f, the device is fed collapsed and percutaneously inserted to a position upstream of the bleeding area and the occlusion device 5.14 is deployed. After the bleeding is stopped the pumping balloon 5.1 starts to operate in non-gating mode. During deflation of the pumping balloon 5.1 the upstream (as shown, distal) check valve 5.5 opens and vacuums blood into the lumen surrounding the pumping balloon. During inflation of the pumping balloon 5.1, the upstream check valve 5.5 closes and the blood is ejected towards the lateral branch 5.6a. The rate and volume of the balloon inflation cycles determine the desired output.

Figure 6A:
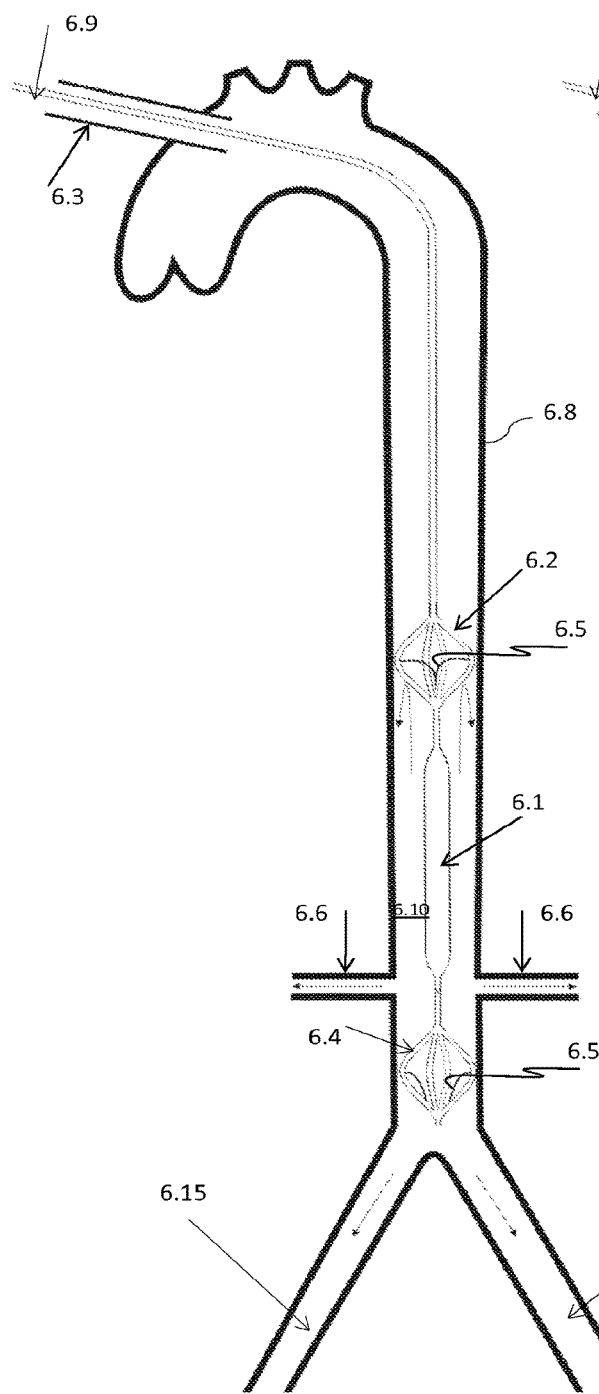
Figure 6B:
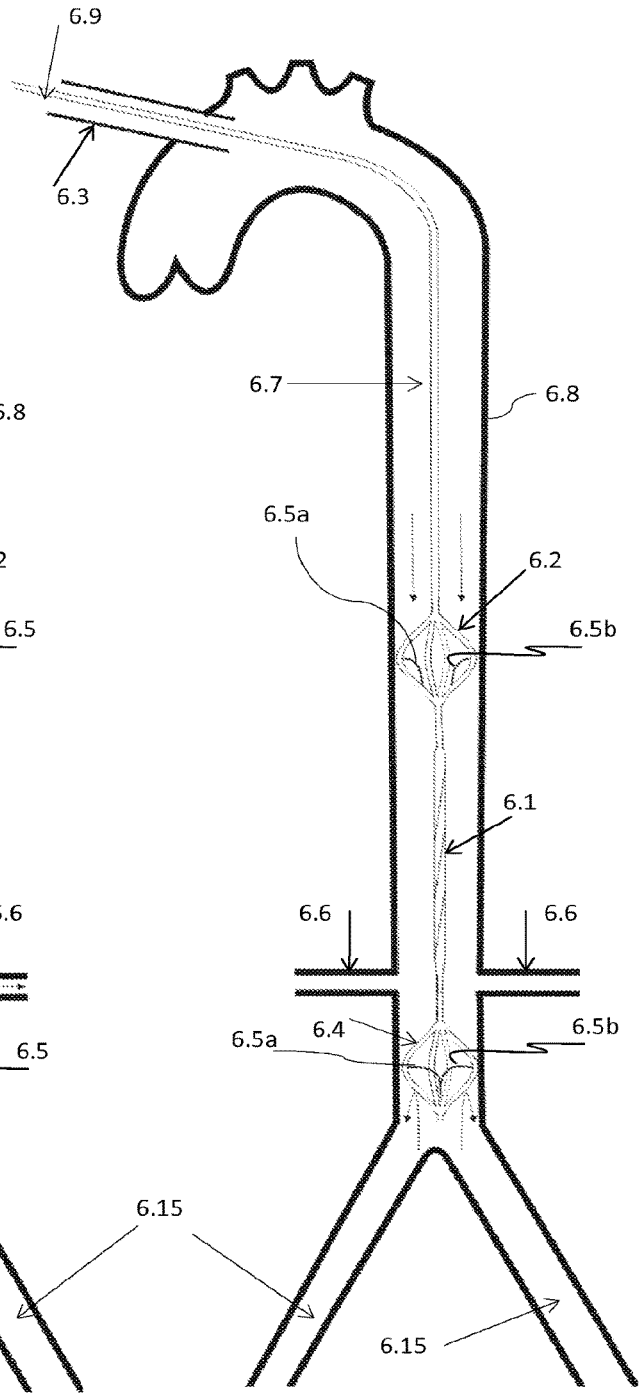

In FIGS. 6a and 6b, a 'renal' IAB is combined with a proximal expandable frame 6.2 including a distally-opening check valve 6.5 and a distal expandable frame 6.2 including a distally-opening check valve 6.5. As in the prior exemplary embodiments, it is inserted through the aortic cannulation site 6.3, during Cardiopulmonary By-Pass (CPB). In FIG. 6b, the pumping balloon 6.1 is in deflation, the proximal check valve 6.5 on expandable frame 6.2 is open and allows downstream flow from the LV and upper aorta 6.7, and the distal check valve 6.5 on expandable frame 6.4 is closed to prevent upstream retrograde flow from more peripheral sites 6.15, which again reduces 'steal phenomenon' from the periphery. In FIG. 6a, the pumping balloon 6.1 is inflated, the proximal check valve 6.5 on expandable frame 6.2 is closed to prevent upstream retrograde flow from the lower aorta 6.10, and the induced flow is isolated within the lower aorta 6.10 and that way directed towards the renal arteries 6.6. Distal check valve 6.5 on expandable frame 5.4 is open and allows downstream flow.

It is important to mention that as in the embodiments shown in FIGS. 5c and 5d the distal expandable frame 5.4 could also include a occlusion device such as the membrane 5.15. The occlusion device would occlude partially the downstream flow and thereby produce greater pressure assist in the renal arteries 6.6 (while reducing pressure assist to more peripheral sites 5.15). Alternately, a second distal expandable frame, upper or lower with respect to the distal expandable frame 6.4, may provide this feature while simplifying manufacturing of the respective expandable frames.

FIGS. 7a and 7b, 8a and 8b, and 9a and 9b depict other exemplary or preferred embodiments where the entry site of the IAB is the traditional femoral access 7.11, 8.11, and 9.11, respectively, and the IAB is gated with the aortic valve 7.12, 8.12, and 9.12 respectively, in counterpulsation mode. Although the current invention can be used to augment pressure and blood flow in any branches of the lower (abdominal) and upper (thoracic) aorta, an exemplary emphasis will continue to be given to the renal arteries and lower aorta where they originate.

Figures 7A, 7B:
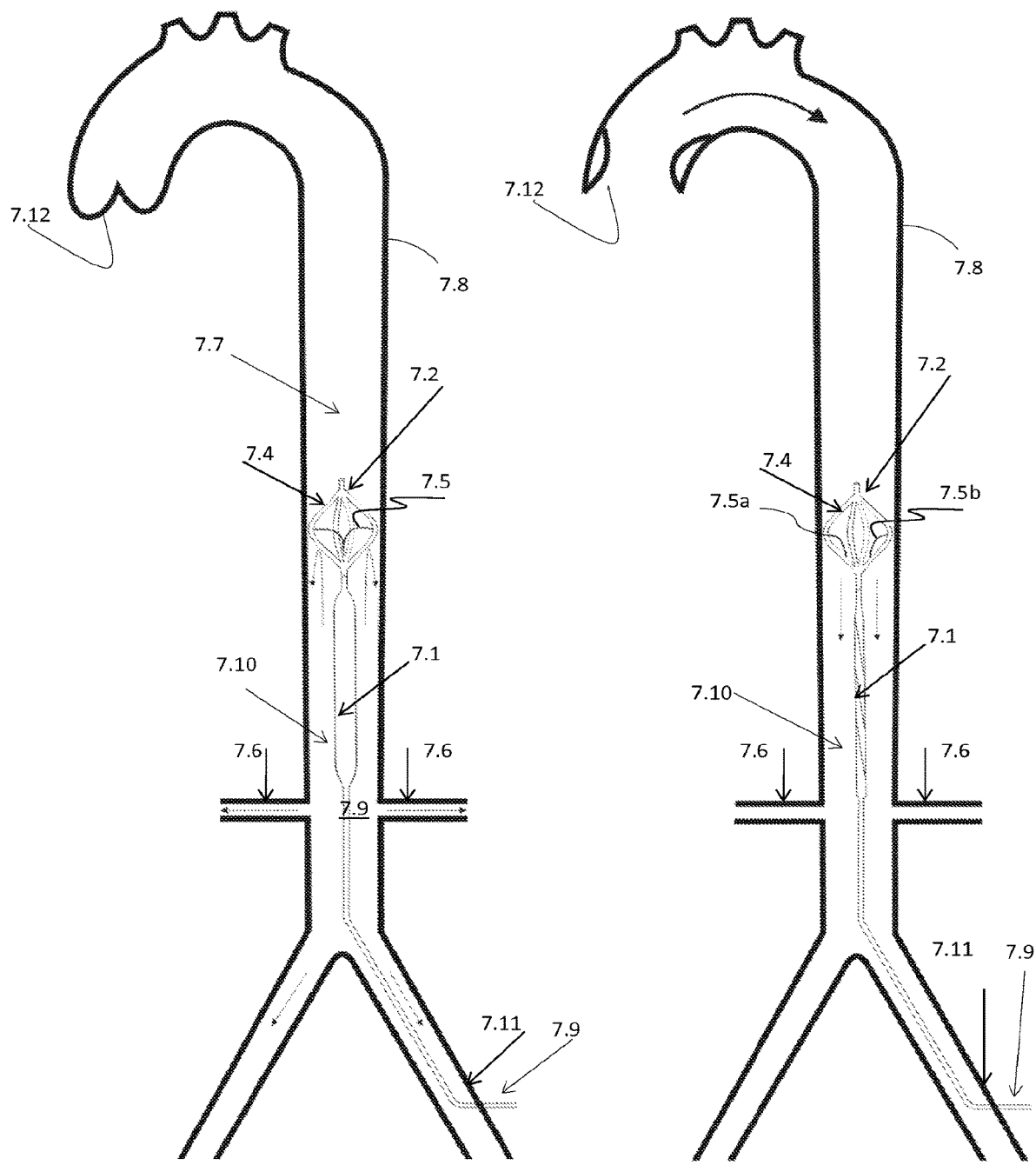

FIGS. 7a and 7b show to views of an IAB, inserted through the femoral artery 7.11, aiming to increase the renal flow in a patient e.g. with pre-renal failure secondary to low cardiac output. The pumping balloon 7.1 is combined with a distal expandable frame 7.4 having a proximally-opening unidirectional valve, check valve 7.5, allowing downstream flow only. The reader will appreciate that due to the reversed orientation of the implanted system, the orientation of frame features such as the check valve 7.5 and any occlusion device will be reversed with respect to the system. In FIG. 7b the aortic valve 7.12 is open, the pumping balloon 7.1 is in deflation, and check valve 7.5 is open and allows downstream flow. In FIG. 7a the aortic valve 7.12 is closed, the pumping balloon 7.1 is inflated, and check valve 7.5 is closed, thereby 'isolating' the pressure augmentation effect in the lower aorta 7.10 below the valve, where the renal arteries 7.6 originate.

Figures 8A, 8B:
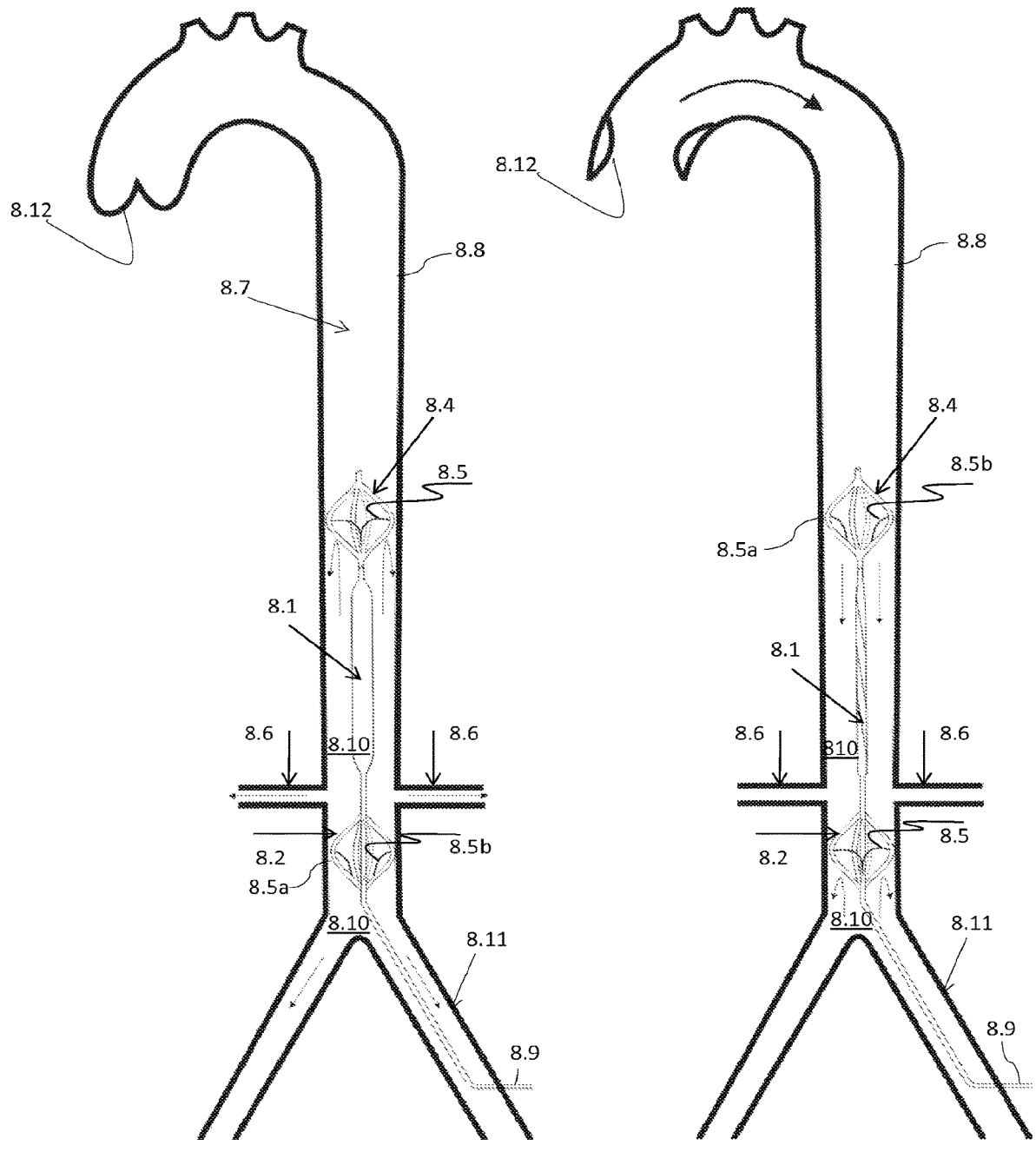

In FIGS. 8a and 8b, the IAB is combined with a proximal expandable frame 8.2 including a proximally-opening check valve 8.5 and a distal expandable frame 8.4 including a distally-opening check valve 8.5. In FIG. 8b, the aortic valve 8.12 is open, the pumping balloon 8.1 is in deflation, the distal check valve 8.5 on expandable frame 8.4 is open and allows downstream flow; and the proximal check valve 8.5 on expandable frame 8.2 is closed, preventing upstream retrograde flow and thereby increasing the 'vacuum effect' and pooling of blood in the lower aorta 8.10 where the renal arteries 8.6 originate. In FIG. 8a, the aortic valve 8.12 is closed, the balloon pump 8.1 is inflated, the distal check valve 8.5 on the expandable frame 8.2 is closed and prevents upstream flow to any other arteries apart from the ones below that expandable frame, and the proximal check valve 8.5 on the expandable frame 8.4 is open thereby allowing increased pressure and flow towards the lower limbs.

In FIGS. 9a and 9b, the IAB is combined with a proximal expandable frame 9.2 including a occlusion device 9.14 and a distal expandable frame 9.4 including a distally-opening check valve 9.5. The occlusion device may comprise a membrane 9.14 attached to the inner surface 9.13 of the expandable frame 9.2. As mentioned before, a similar occlusion device could be an inflated occlusion balloon, positioned at the same level. Again, the occlusion device 9.14 provides a twofold advantage: 1. a partial downstream flow obstruction which augments retrograde flow to the renal arteries 9.6 and 2. a prevention of retrograde flow from more peripheral sites 9.15 which reduces 'steal phenomenon' from the periphery thereby increasing blood flow in the lower aorta 9.10 between the respective expandable frames 9.2 and 9.4.

Figures 10A, 10B:
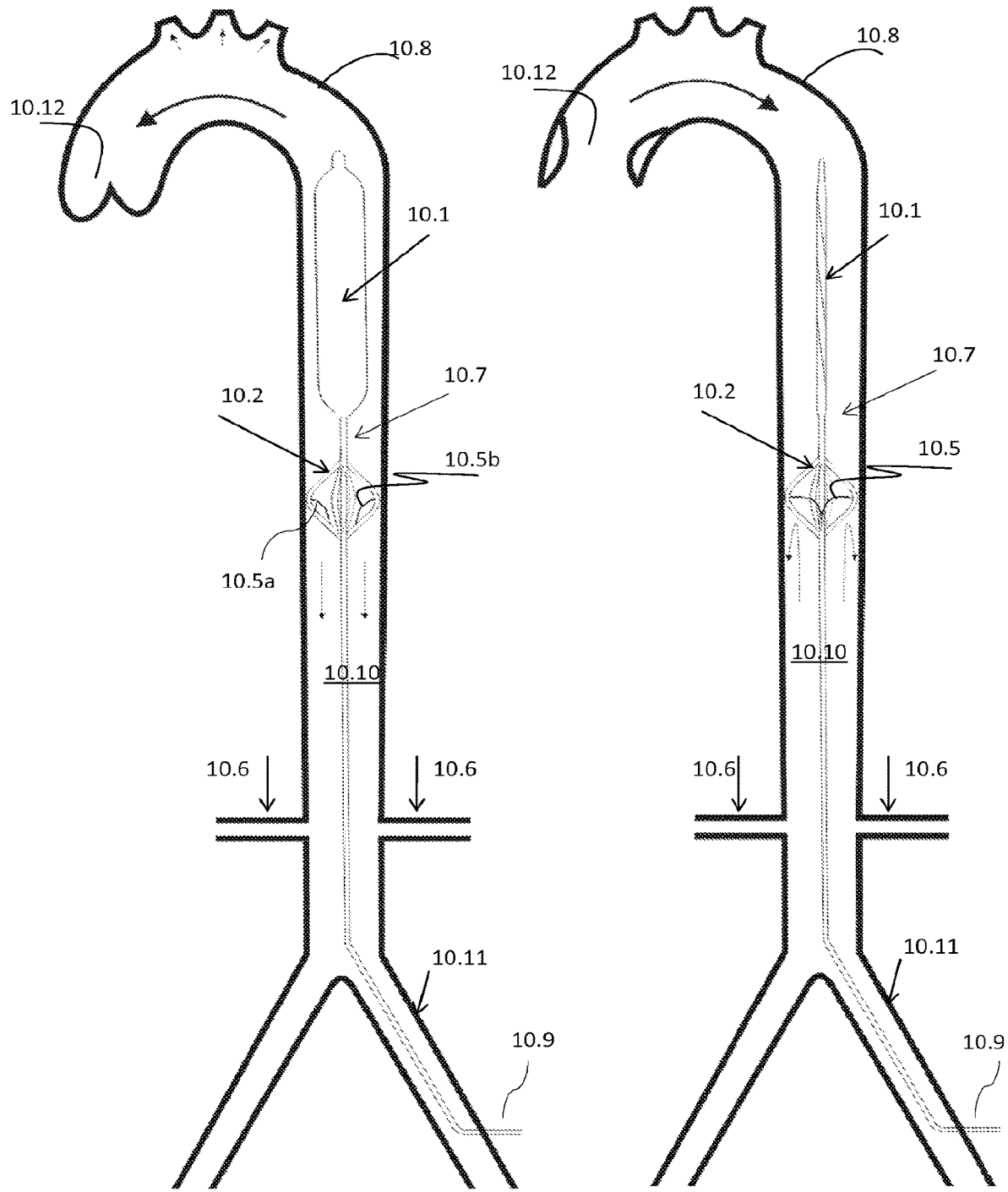
Figures 11A, 11B:
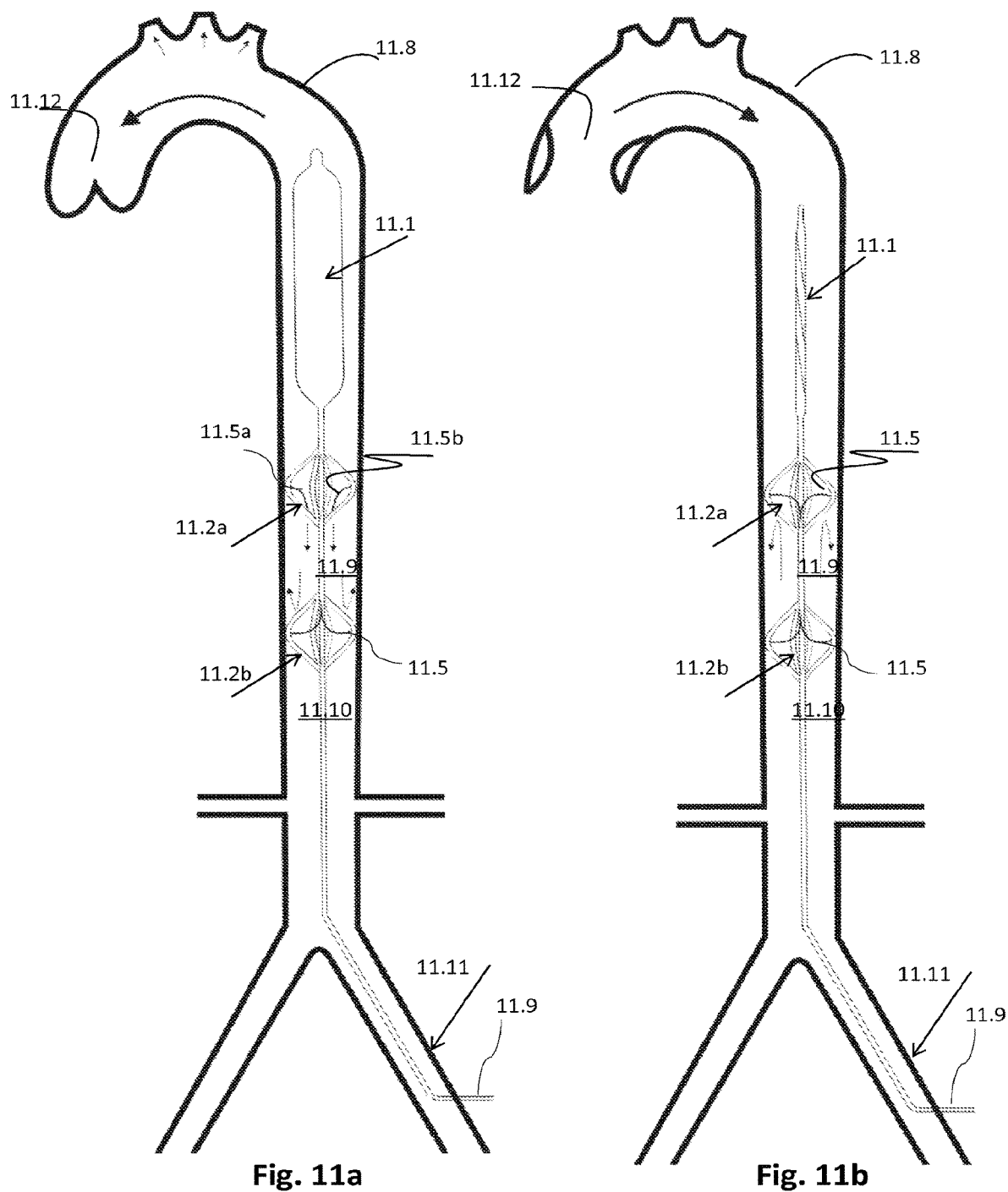

FIGS. 10a and 10b illustrate an exemplary IAB including a pumping balloon 10.1 combined with a single expandable frame 10.2 placed at its proximal end. This proximal expandable frame 10.2, shown in an expanded state, is carrying a proximally-opening unidirectional check valve 10.5. Here again semi-lunar leaflets 10.5a and 10.5b originating from an annular portion of the expandable frame 10.2 are depicted. The leaflets of the check valve are thin, supple and move easily from the completely open position (when the pumping balloon 10.1 inflates) to the closed position (when the pumping balloon 10.1 deflates). In FIG. 10b the check valve 10.5 closes when the pumping balloon 10.1 starts to deflate, prior to the closure of the aortic valve 10.12, whereas in FIG. 10a the check valve 10.5 opens as downstream flow originating from the heart forces the leaflets to open.

In this view the aorta 10.8, the aortic valve 10.12, and renal 10.6 and common iliac/femoral arteries 10.11 are shown. The exact positioning of the expandable frame 10.2 in relation with the renal arteries 10.6 remains to be ascertained. However it is anticipated that the best position of the expandable frame 10.2 will be 4-5 cm just above the renal arteries. This helps to prevent retrograde flow from the renal arteries during the balloon's deflation, and yet allow downstream flow towards the renal arteries 10.6 without impeding the flow. At the time of implantation or after the implantation, the doctor may evaluate the exact positioning by looking at an image produced by an angiogram with contrast injection performed after the insertion of the system. Ideally, contrast agent injected below the check valve 10.5 of the expandable frame 10.2, shouldn't reach the upper aorta 10.7 above the check valve 10.5.

FIGS. 11a and 11b and 12a to 12c illustrate two other exemplary or preferred embodiments related to the apparatus shown in FIGS. 10a and 10b, incorporating a femorally inserted 11.11, 12.11 apparatus, upper proximal expandable frames 11.2a and 12.2a, respectively, having proximally-opening check valves 11.5 and 12.5, respectively, and pumping balloons 11.1 and 12.1, respectively, operating in counterpulsation mode, but additionally lower proximal expandable frames 11.2b and 12.2b, respectively, which function as selectively deployable blocking elements.

Figures 12A, 12B, 12C:
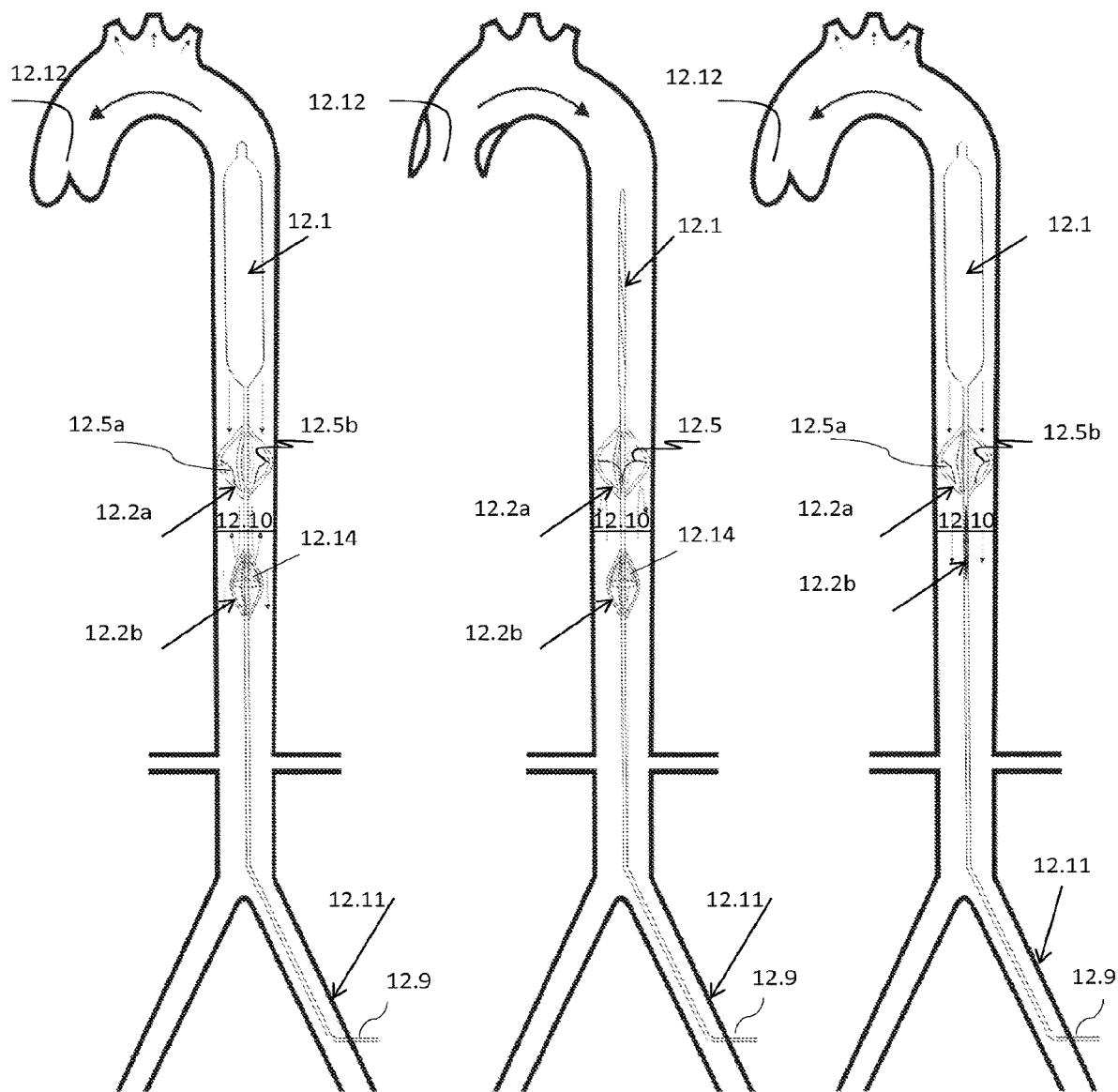

In both embodiments the lower proximal expandable frames 11.2b, 12.2b remain collapsed but at the disposal of the operator—for sake of clarity, FIGS. 11a, 11b, 12a, and 12b show the deployed configurations, and FIG. 12c shows the collapsed, 'normal state' configuration. The former embodiment, 11.2b, integrates a 'complete' blocking element, i.e. a distally-opening unidirectional check valve 11.5, while the letter integrates a occlusion device 12.14 providing partial blocking, such as a continuous membrane mounted thereupon or an inflatable occlusive balloon. If a Low Cardiac Output state occurs (ejection fraction <15%) the lower proximal expandable frame 11.2b, 12.2b is deployed to at least partially block the downstream flow (at 11.9, 12.10). That way the limited cardiac output and the pressure generated from the heart is used momentarily to perfuse the upper part of the body, the brain and the heart, until cardiac output is restored.

Figure 13A:
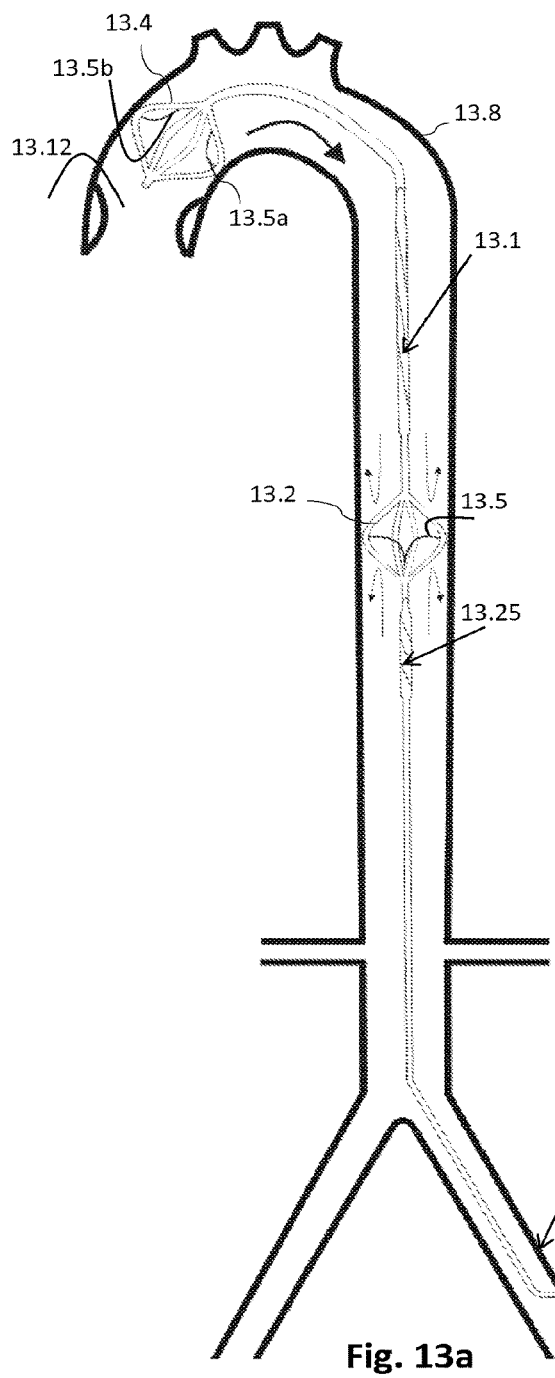
Figure 13B:
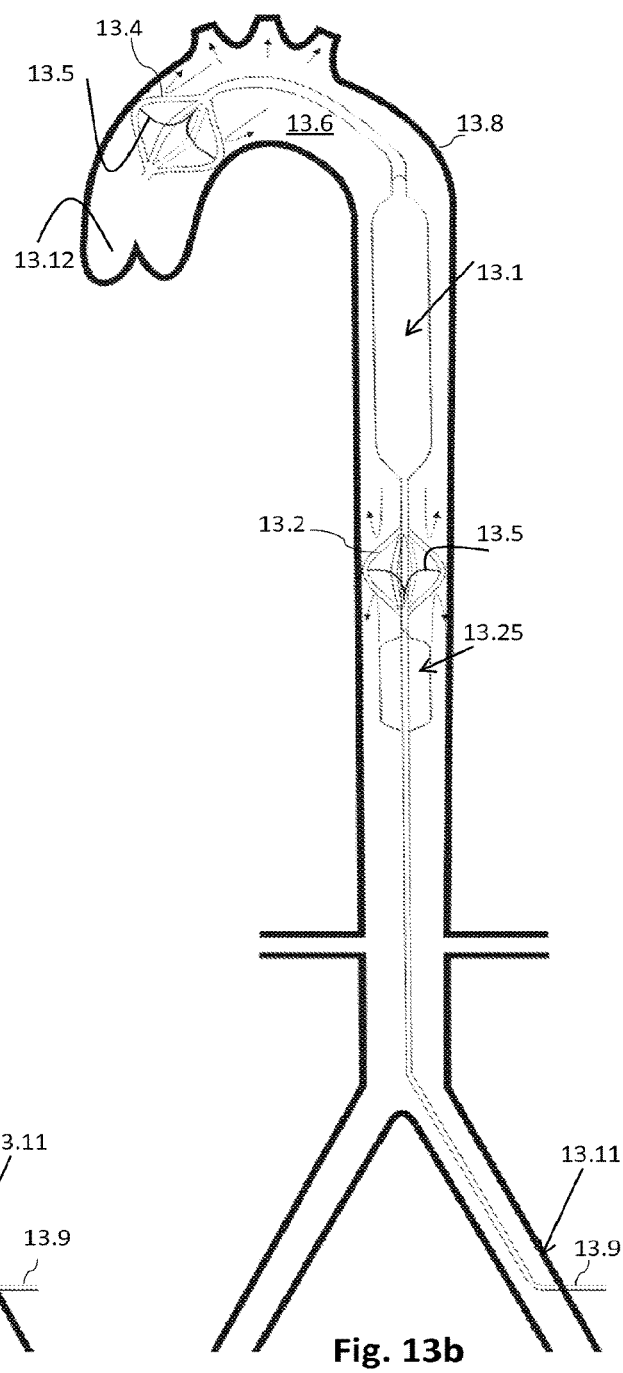

FIGS. 13a and 13b depict a preferred embodiment for increasing aortic pressure in a specific compartment of the aorta 13.8, with the embodiment incorporating a pumping balloon 13.1 fluidically connected to more proximal bi-directional valve 13.25, such as an occlusive balloon.

Fluidically connected bi-directional valves, specifically assist balloons to IAB, have been described before in the literature. There are commercially available downstream balloons with a particular aim to retain the pressure wave augmentation above the pumping balloon of an IAB. However this pressure split relies on the proximity of the assisted balloon to the vessel wall. It is easily understood by those familiar with the art that close proximity predisposes to aortic wall trauma. Subsequently there is a fine balance between pressure effect compartmentalization and aortic wall trauma, making it apparently impossible to achieve both. The embodiment shown in FIGS. 13a and 13b circumvents the aforementioned limitations by integrating a proximal expandable frame 13.2, including a distally-opening, unidirectional check valve, proximate the bi-directional valve 13.25 interposed between the bi-directional valve 13.25 and the pumping balloon 13.1. This proximal expandable frame 13.2 conforms precisely the interior of the Aorta and centralizes the bi-directional valve balloon 13.25 within the aorta 13.8.

As shown in FIG. 13a, during deflation of the pumping balloon 13.1 the check valve 13.5 on the interposed expandable frame 13.2 closes and prevents retrograde flow. As shown in FIG. 13b, during inflation of the pumping balloon 13.1 the check valve 13.5 on the interposed expandable frame 13.2 would normally open. However the close proximity of the bi-directional valve balloon 13.25 to the proximal side of the check valve 13.5, compared to the pumping balloon 13.1, creates locally higher pressure which either prevents or delays opening of the interposed check valve. A variety of bi-directional valve balloon volumes and distance relationships can be used in order to predetermine the interposed check valve's opening delay. Both the distance and balloon volume determine local pressure augmentation and check valve closure delay/opening timing. It is important to understand that the proximal bi-directional valve 13.25 is an alternative to the lower proximal expandable frame 12.2b shown in FIGS. 12a and 12b.

FIGS. 14a and 14b, 15a and 15b, and 16a and 16b show exemplary embodiments particularly useful in enforcing pressure and flow in peripheral parts of the circulation. The apparatuses will be described in conjunction with methods of venous flow and carotid flow augmentation. Despite that, it must be understood that usage is not restricted to these cases, as the apparatuses and methods have a wider range of clinical applicability in circulatory lumens generally. There are several clinical entities, such as venous insufficiency and intracranial oedema, where augmentation of venous return towards the heart is essential in order to alleviate peripheral venous congestion.

Figure 14A:
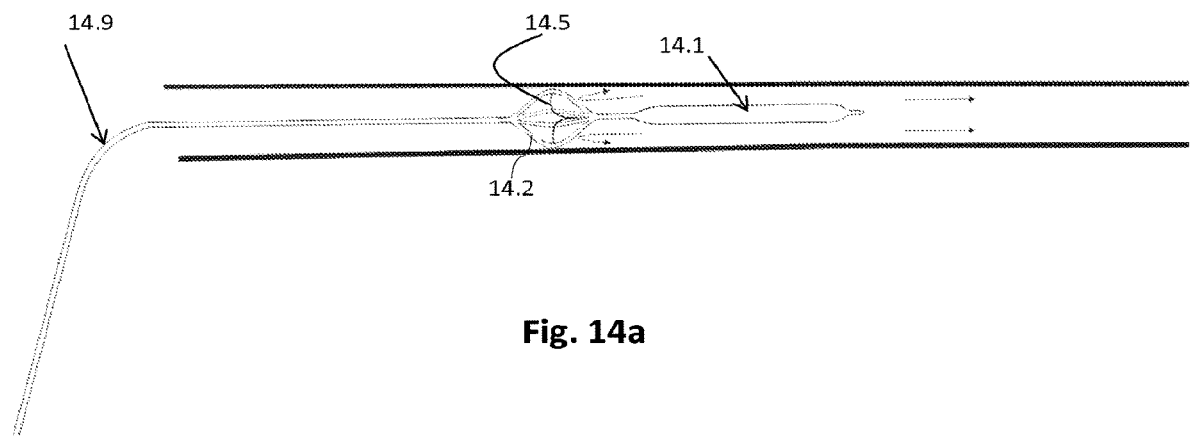
Figure 14B:
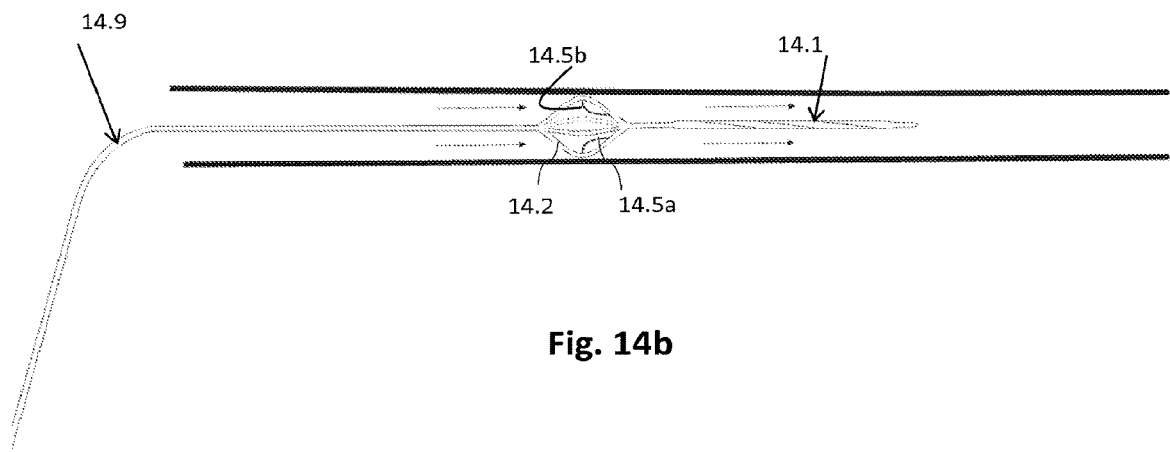

FIGS. 14a and 14b show a circulatory assist apparatus including a pumping balloon 14.1 and one proximal expandable frame 14.2 including a distally-opening, unidirectional check valve 14.5. This system may be used when pressure increase in a body cavity or vessel is more important compared to axial flow such as the in the cases where stenoses exist in several arterial branches originating from a main artery. The flow increase in the main artery doesn't necessarily generate flow increases in all arterial branches given the fact that higher flow will occur mainly in the non-stenotic branches. In those cases pressure increase is more appropriate means of increased perfusion. When the pumping balloon 14.1 deflates the pressure drop causes the proximal check valve 14.5 to open and allow flow into the arterial space surrounding the balloon. Subsequently when the pumping balloon 14.1 inflates the proximal check valve 14.5 closes and the pressure and flow increase on the distal side of the check valve 13.5. The pressure increase is proportional to the balloon displacement volume.

Figure 15A:
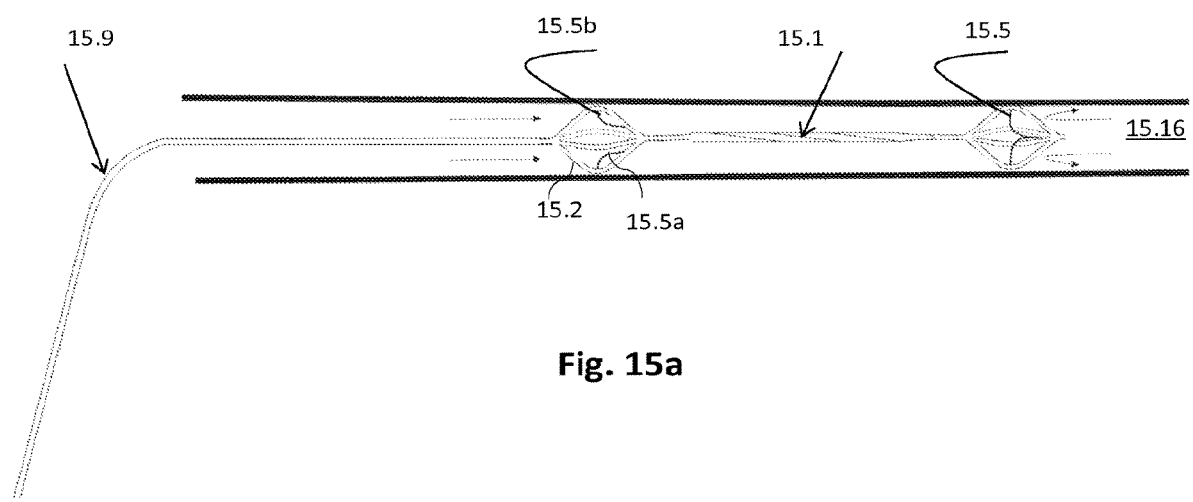
Figure 15B:
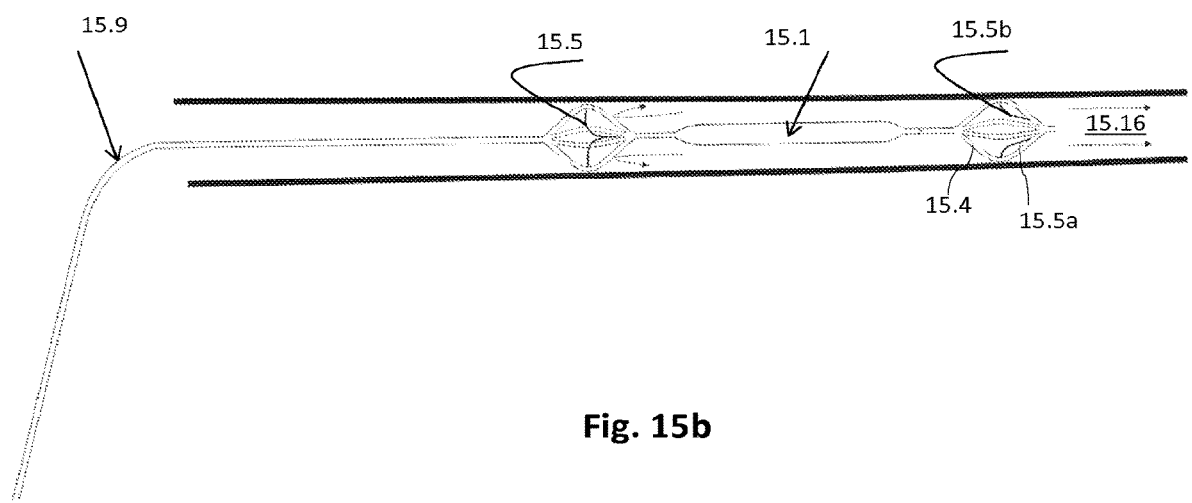

FIGS. 15a and 15b illustrate a preferred circulatory assist apparatus, inserted through a peripheral artery, incorporating two expandable frames, a proximal expandable frame 15.2 and a distal expandable frame 15.4, each including a distally-opening, unidirectional check valve 15.5, and a pumping balloon 15.1 therebetween. The apparatus enhances blood flow towards its distal end, opposite to the insertion site. The apparatus could be for instance inserted in the upper portion of the jugular vein and advanced towards the heart. During deflation of the pumping balloon 15.1, the proximal check valve 15.5 on expandable frame 15.2 is open, and the distal check valve 15.5 on expandable frame 15.4 is closed, vacuuming, in the described instance, venous blood from the brain. During inflation of the pumping balloon 15.1 the pressure increases, the proximal check valve 15.5 on expandable frame 15.2 closes, the distal check valve 15.5 on expandable frame 15.4 opens, and the blood is ejected, in the described instance, towards the right atrium. It is important to note that in the cases where the apparatus is used to enhance venous flow, gating in counterpulsation is not needed. Thus small or big balloon volumes and fast or slow inflation rates can be used. However small balloons in high pumping frequencies may be advantageous in order to prevent stasis and thrombogenesis. It is preferable that the balloon volume is sufficient to achieve a pressure increase adjacent the pumping balloon 15.1 above the pressure of the distal site 15.16, in every inflation cycle, in order for blood to be ejected.

Figure 16A:
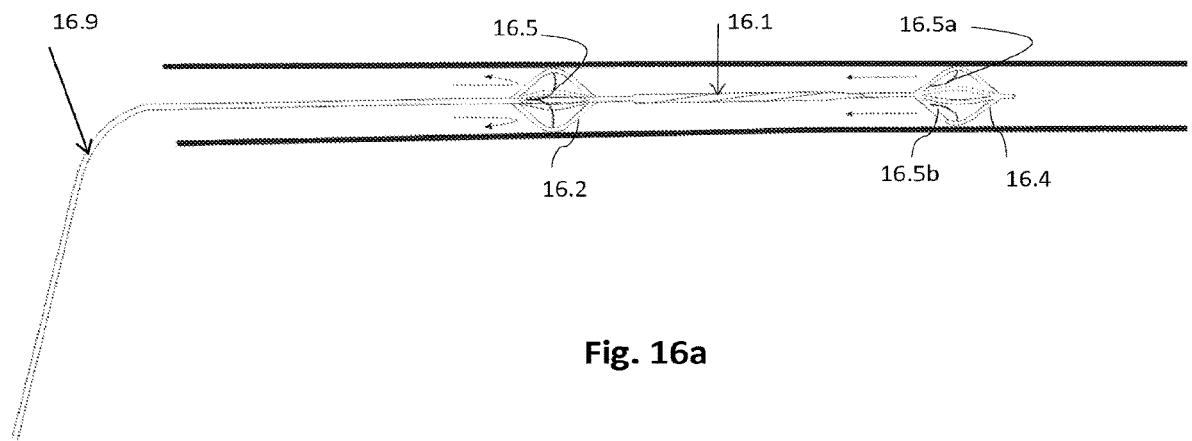
FIGS. 16a and 16b are schematic representations of exemplary and/or preferred embodiments and methods of using the system in a vein.
Figure 16B:
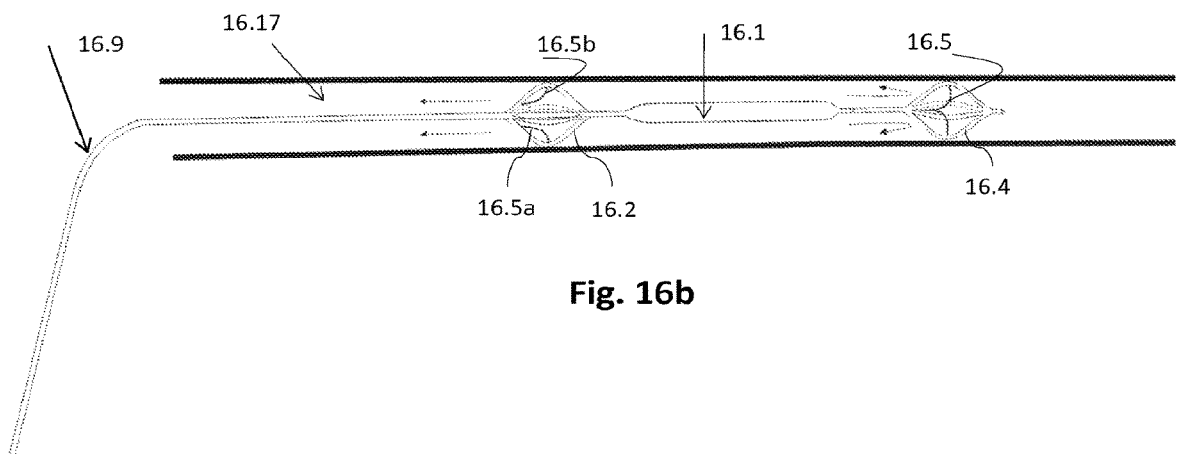

FIGS. 16a and 16b depicts a variant embodiment where the orientation of the unidirectional check valves 16.5 with respect to the apparatus and insertion site are reversed. It is apparent that reverse flow assist apparatuses can be used to achieve fluid vacuum from a body vessel or body cavity, and can be inserted via a distal site and advanced towards the area of deployment. This system can be inserted percutaneously, for example via the femoral vein and advanced upwards into the jugular vein for deployment. In such instances the blood is ejected towards the balloon catheter 16.9 and insertion site, on the proximal sides of the check valves 16.5. When the pumping balloon 16.1 deflates, the distal check valve 16.5 on the expandable frame 16.4 opens and blood is vacuumed into the space between the expandable frames 16.2, 16.4 adjacent the pumping balloon. Subsequently when the pumping balloon 16.1 inflates the proximal check valve 16.5 on the expandable frame 16.2 opens and the pressure and flow increase on the proximal side of that check valve 16.5.

Figure 17A:
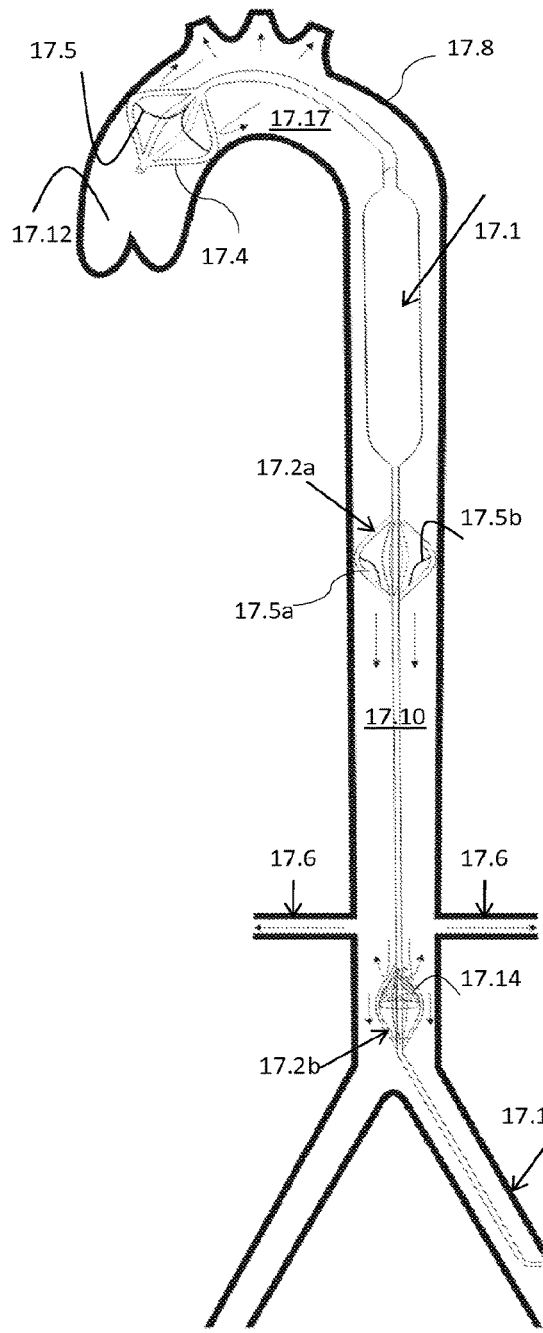
FIGS. 17a and 17b, 18a and 18b, 19a through 19f, and 20a and 20b are schematic representations of exemplary and/or preferred embodiments and methods of using the system to provide compartmentalized assist within an aorta.
Figure 17B:
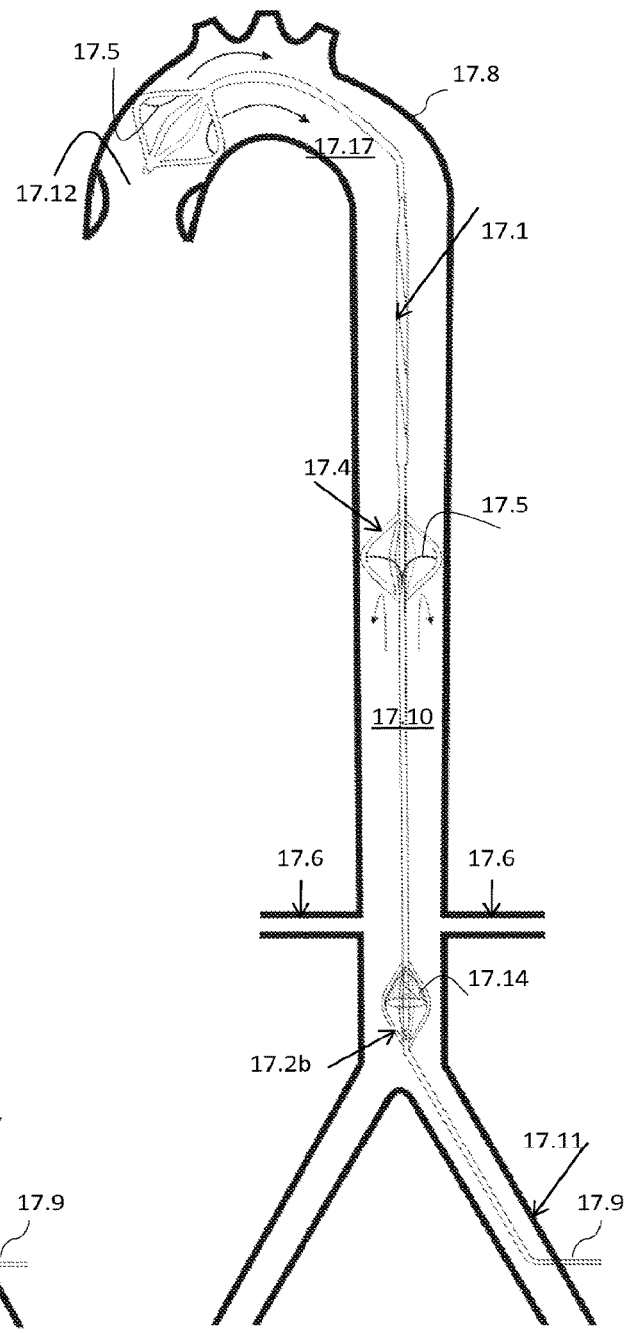

FIGS. 17a and 17b depict another exemplary or preferred embodiment as well as a method of using with a system including expandable-frame-mounted check valve and blocking elements for selectively increasing the blood flow and pressure in a specific compartment of the arterial circulation. The apparatus may be inserted through an incision made upstream or downstream from a selected position, with the relative position of the expandable frames (proximal and distal), relative orientation of the check valves (distally-opening and proximally-opening), and relative placement of the blocking element (within the distal or proximal expandable frame) varying appropriately as described earlier above.

In the case of downstream insertion, the apparatus may sequentially integrate a distal expandable frame 17.4 including a proximally-opening check valve 17.5, a pumping balloon 17.1 balloon, preferably operated in counterpulsation mode, a proximal expandable frame 17.2a including a proximally-opening check valve 17.5, and a more proximal expandable frame 17.2b including a occlusion device 17.14 or other blocking element. It is important to note that the apparatus is similar to that shown in FIGS. 12a through 12c, but the more proximal expandable frame 17.2b is ordinarily deployed, not remaining collapsed. The distal check valve 17.5 on the expandable frame 17.4 is a unidirectional 'downstream' valve that defines the most upstream point where pressure augmentation occurs. This may have clinical significance if, for example, one wants to augment flow in the left common carotid artery but not the right subclavian artery. This may be needed in a case where the left common carotid artery is stenotic producing an evolving stroke. The proximal check valve 17.5 on the expandable frame 17.2a is also a unidirectional 'downstream' valve that closes with balloon deflation, prevents retrograde flow from below the balloon 17.1, and increases blood flow from above, such as from the LV. Although the proximal check valve 17.5 is sufficient to prevent retrograde flow, it is not sufficient to compartmentalize the aorta 17.8 and prioritize for pressure augmentation compartmentalization, e.g., above the lower extremities. To serve this purpose a second expandable frame 17.2b including a blocking element is used. The level of the blocking element defines the lower limit where pressure increase mainly occurs. The degree of expansion of the blocking element defines the pressure ratio between the compartmentalized space above and uncompartmentalized space below the blocking element.

FIGS. 17a and 17b illustrate an exemplary implementation where the apparatus is used to increase the blood pressure in an aortic compartment extending from the Aortic Arch 17.17 to the lower aorta 17.10, aiming to prioritize a flow increase towards the brain and renal arteries 17.6, thus the more proximal expandable frame 17.2b is placed under the renal arteries. It has a particular use in ischemic stroke and renal failure patient. The pumping balloon 17.1 deflates just prior to the aortic valve 17.12 opening to assist the LV to eject blood out. The proximal check valve 17.5 on the expandable frame 17.2a closes because of the pressure fall and the distal check valve 17.5 on the expandable frame 17.4 opens allowing the balloon to vacuum blood out of the heart. During inflation of the balloon 17.1 the pressure increases in the Aorta (17.8), the upper valve closes (17.2), the lower valve (17.4) opens (17.9) and the blocking element (17.3) directs the flow towards the renal arteries (17.11).

Figure 18A:
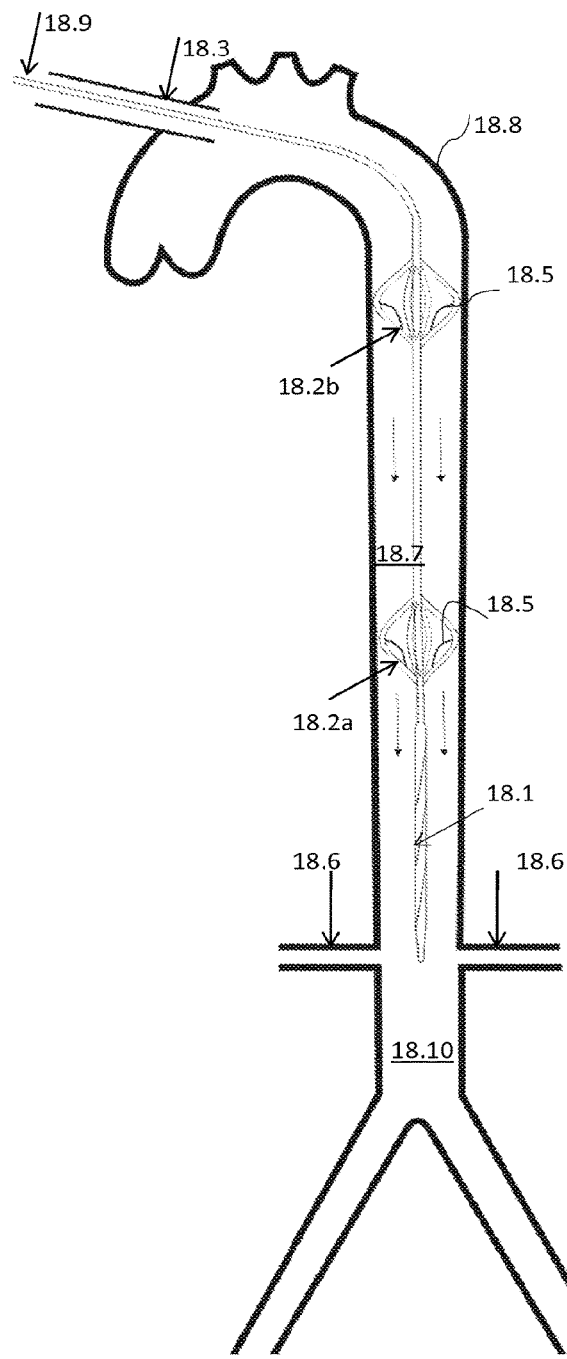
Figure 18B:
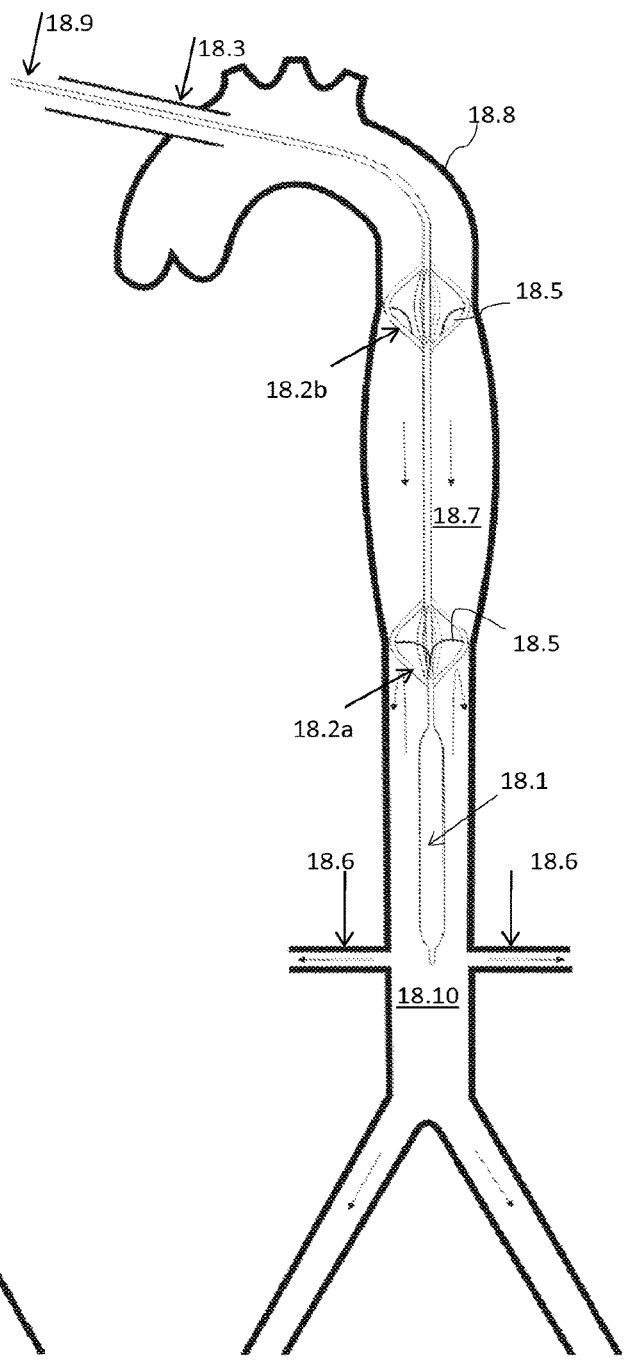

FIG. 18 depicts a variation of the apparatus shown in FIG. 4. integrating an additional, lower proximal expandable frame 18.4 with a distally-opening check valve 18.5. This more proximal check valve 18.5 prevents direct pressure transfer to the cannulation site when the pumping balloon 18.1 inflates. As described earlier (in the context of the apparatus of FIGS. 4a and 4b) the apparatus of this embodiment can be used to increase the blood pressure and flow in any part of the circulation during CPB. Both the lower proximal check valve and upper proximal check valve 18.5 in the respective expandable frames 18.2a and 18.2b are unidirectional 'downstream' valves. Deflation of the pumping balloon 18.1 draws blood into the aorta 18.8 which forces the respective valves to an open configuration. When the pumping balloon 18.1 inflates, expansion of the balloon pushes blood downstream, e.g., into the renal arteries 18.6, but also upstream which temporarily closes the upper proximal valve 18.5 on expandable frame 18.2a and therefore impedes retrograde flow. This temporarily increases the pressure in the upper aorta 18.7 and causes it to dilate. The inventor has observed that this pressure effect may be transmitted as a rebound wave to the aortic insertion site 18.3 and damage the cannulation point, i.e., rupture of the tissue around the cannulation point. The more proximal check valve 18.5 on the lower proximal expandable frame 18.2b prevents the direct pressure transmission to the insertion site 18.3 and causes part of the upper aorta 18.7 between the proximal expandable frames 18.2a, 18.2b to dilate, behaving as a buffer chamber, which prevents acute pressure changes.

FIGS. 19a and 19b, and 19c and 19d illustrate additional exemplary or preferred embodiments and the basic advantage of the disclosed system. It is generally desirable to position the pumping balloon 19.1 as close as possible to the left ventricle (LV) so as to more efficiently induce a 'vacuum effect.' However under 'normal circumstances' a straight pumping balloon cannot be placed in the aortic arch 19.17 or any other curved vessel. The pumping balloon would traumatize the aortic wall during inflation, because of a 'whipping' phenomenon, attributed mainly to continuous balloon movement during inflation/deflation, the fact that the straight pumping balloon cannot fit in the aortic arch's curvature after inflation, and secondary turbulent flow. All of these would induce a continuous trauma causing the aortic arch 19.17 to eventually rupture. Such approaches have not been successful yet in any clinical setting. Along the same lines, a second assistant balloon that has to match the Aorta's diameter is necessary to be larger to the main pumping balloon. Wrapping of such a large balloon, around a balloon catheter, would increase substantially the diameter of the balloon catheter and make percutaneous insertion of the intra-aortic balloon very difficult.

Figure 19A:
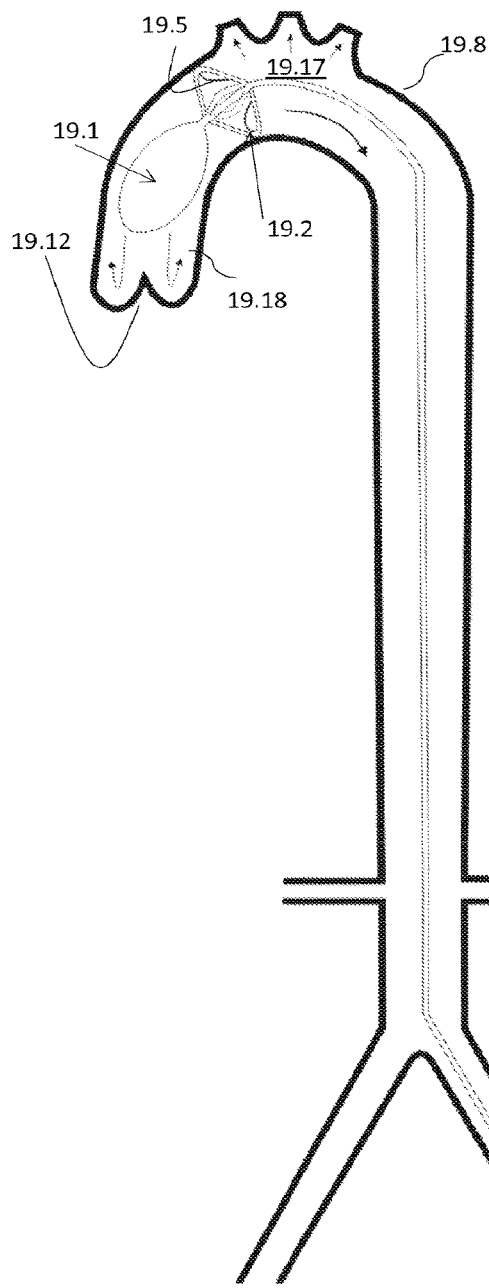
Figure 19B:
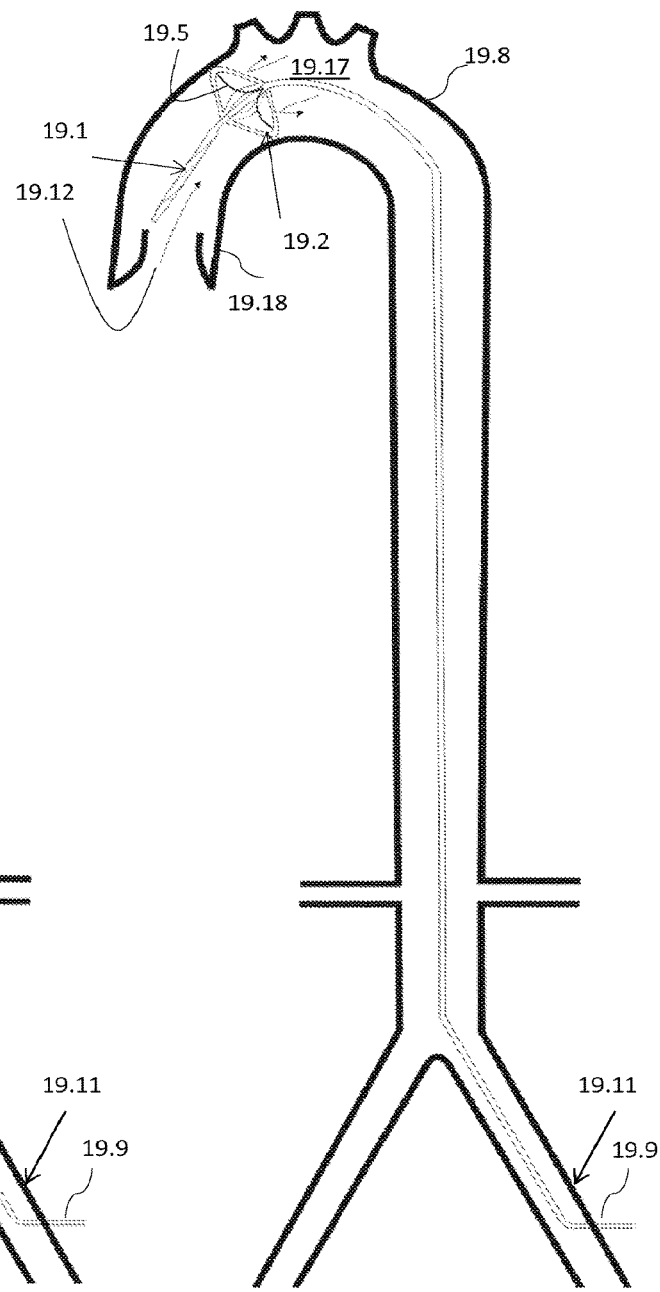

FIGS. 19a and 19b show an apparatus having smaller size and diameter pumping balloon 19.1 that has been advanced in the ascending aorta through a peripheral artery, such as a femoral artery site 19.11. The pumping balloon may have an inflated diameter of 12-30 mm and a length of 35-90 mm depending upon patient's size (1.5-1.90 m). The pumping balloon shape may be spheroid, oval, cylindrical or any combination thereof. A typical pumping balloon of this size wouldn't be able to produce any significant vacuum effect, as blood would be vacuumed also from the brain vessels and other arterial branches from the aortic arch 19.17 (a phenomenon that can be described as 'steal flow') towards the ascending aorta 19.18. The combination of this smaller pumping balloon 19.1 with a proximal expandable frame 19.2 incorporating a proximally-opening check valve 19.5, proximate/immediately adjacent to the pumping balloon 19.1, allows the vacuum effect to be contained within the ascending aorta 19.18 and left ventricle.

The balloon preferably operates in a gated, counterpulsation mode, but it can equally effectively operate in a non-gated mode if the cardiac output drops to zero, as it occurs in the context of a cardiac arrest. In FIG. 19b, when the pumping balloon 19.1 deflates, the pressure in the ascending aorta 19.18 drops. As a consequence check valve 19.5 on the proximal expandable frame 19.2 closes, and blood is vacuumed into the ascending aorta from the LV through the open aortic valve 19.12. Subsequently, in FIG. 19a, the pumping balloon 19.1 inflates and its total displacement volume is pushed away at high pressure. The aortic valve 19.12 has closed, and therefore a substantial fraction of the generated blood flow is compressed between the expanding balloon and against the aortic valve, where the coronary ostiae reside. That increases dramatically the coronary flow compared to any other current device.

Figure 19C:
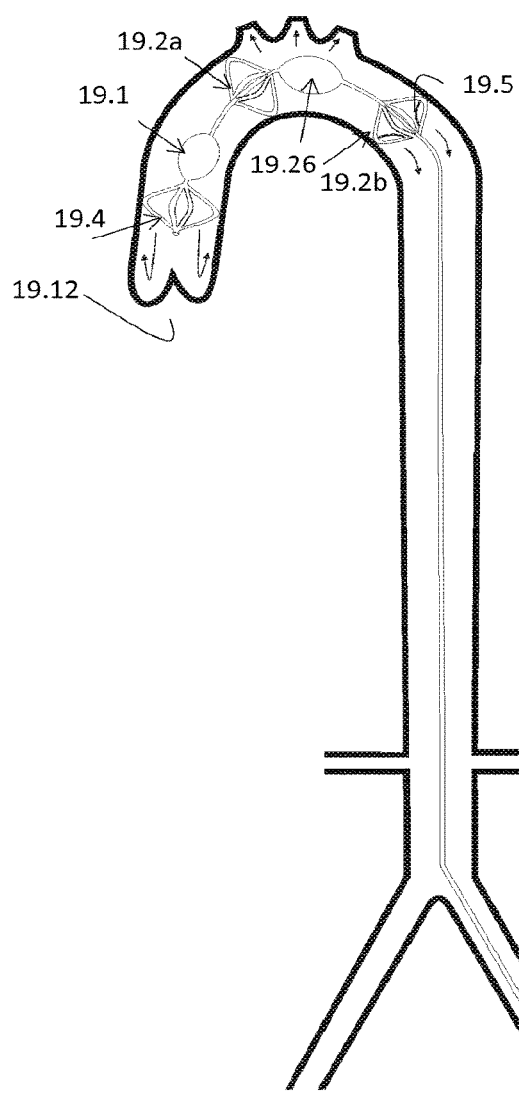
Figure 19D:
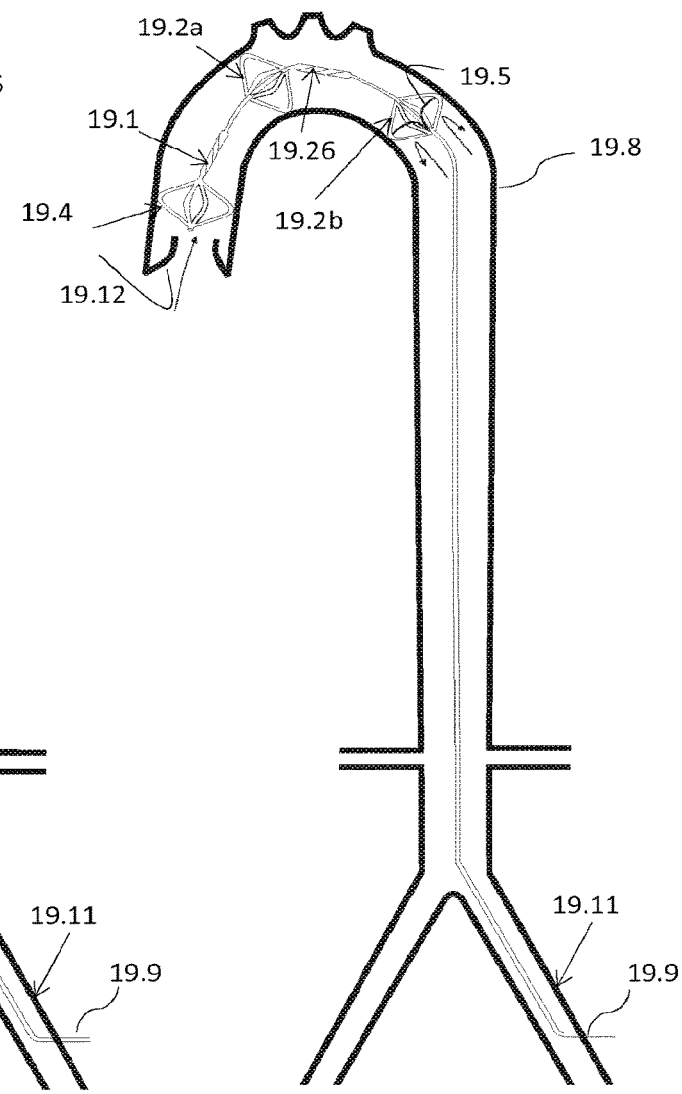

At the same time an large fraction of the vacuumed blood is pushed towards the aortic arch 19.17 and opens the proximal check valve 19.5, gaining access to the rest of the aorta 19.8. Thus this embodiment creates flow even in zero cardiac output conditions, and may serve as a Left Ventricular Assist device. The fact that an IAB-like pumping balloon is isolated within a smaller compartmentalized space makes pressure gradients and flows much higher compared to conventional IABs. This enables miniaturization of the pumping balloon 19.1 and also the balloon catheter 19.9. As shown in FIGS. 19c and 19d, an additional, distal expandable frame 19.4 may be attached at the distal end of the pumping balloon to centralize the balloon tip portion, further reducing potential for a whipping effect. Other structures such as fluidically connected, more proximal balloon 19.26, e.g., an occlusive balloon (as discussed and shown in the context of FIGS. 13a and 13b) or fluidly connected, additional pumping balloon, and/or a lower proximal expandable frame 19.2b including a check valve 19.5 may be added for the purposes described above. As illustrated, the additional balloon 19.26 is an additional pumping balloon fluidly connected to the pumping balloon 19.1. Some attempts have been made in the prior art (U.S. Pat. No. 7,374,531 B1) to split an IAB in smaller IABs in order to make possible more effective assist effect. However in this particular case the pumping balloon is split into smaller balloons 19.1, 19.26, having an expandable frame in between the balloons. This may aid placement of an IAB in the ascending aorta and secondarily in any other part of the aorta 19.8. The interposed proximal expandable frame 19.2a centralizes and stabilizes the balloons to prevent balloon-to-wall contact, thereby preventing the aforementioned whipping effect.

Figure 19E:
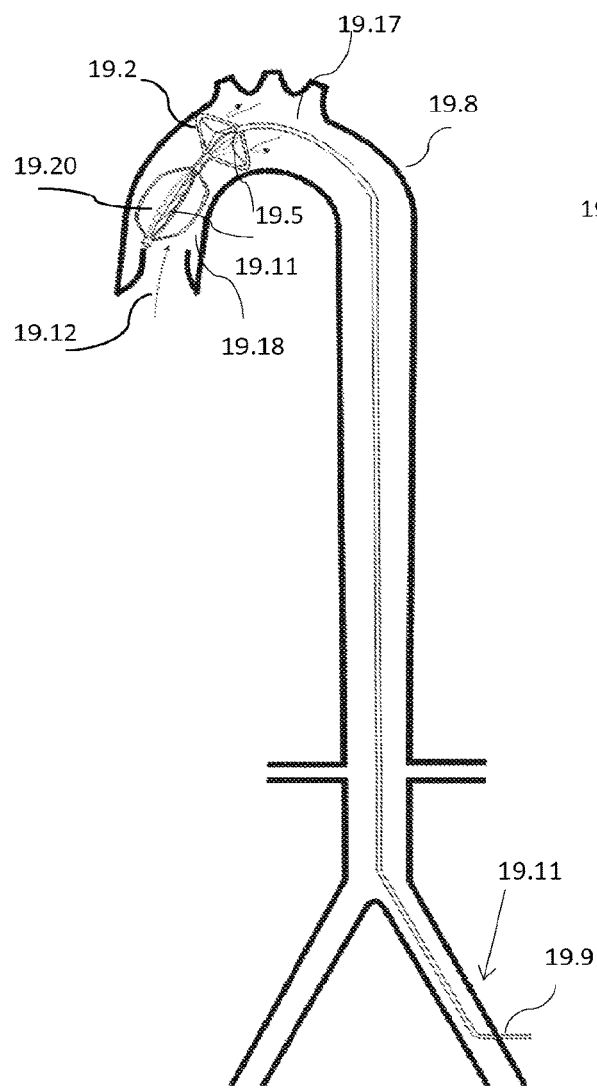
Figure 19F:
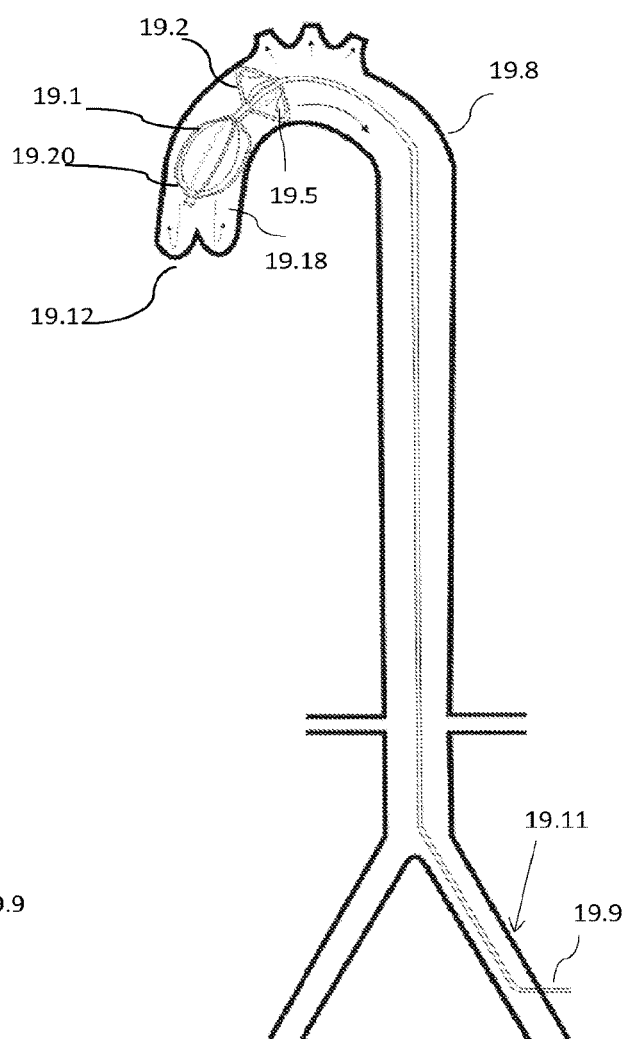

In FIGS. 19e and 19f, a modification of this embodiment is presented where the pumping balloon 19.1 is contained within a surrounding expandable frame 19.20 to avoid aortic wall trauma. The surrounding expandable frame 19.20 and the proximal expandable frame 19.2 share the same general design features as they have been described above (particularly with reference to FIGS. 2a through 2c). The dimensions of the expandable frame 19.20 match the dimensions of the inflated pumping balloon 19.1 in diameter, length and volume to avoid mechanical disruption of the frame. The expandable frame 19.20 is preferably pretreated to self-expand to a predetermined diameter, having its proximal end joined to the balloon catheter 19.9 or to catheter portions interconnecting the balloon with the proximal expandable frame 19.2, and its distal end sliding freely along a distally-projecting segment from the balloon (as discussed in the context of FIGS. 1g through 1j).

If there are multiple pumping balloons, with a frame surrounding each pumping balloon, the length of the interconnecting catheter portion(s) must be sufficient to accommodate the collapsed expandable frame. The interconnecting catheter portion(s) are preferably made of a hollow tube resistant to kinking, having an elongate shape conforming to the generally curved shape of the aortic arch. The distance of each pumping balloon from the previous or next such balloon is such that each pumping balloon has the 'smallest degree of freedom' to move about, preventing balloon to wall contact. A length equal to the collapsed length of the interposed expandable frame is desirable.

Although different deployment methods have already been mentioned, the centering means described in this particular embodiment are ideally deployed and collapsed, by operating an outer sleeve tube as described previously above.

Figure 20A:
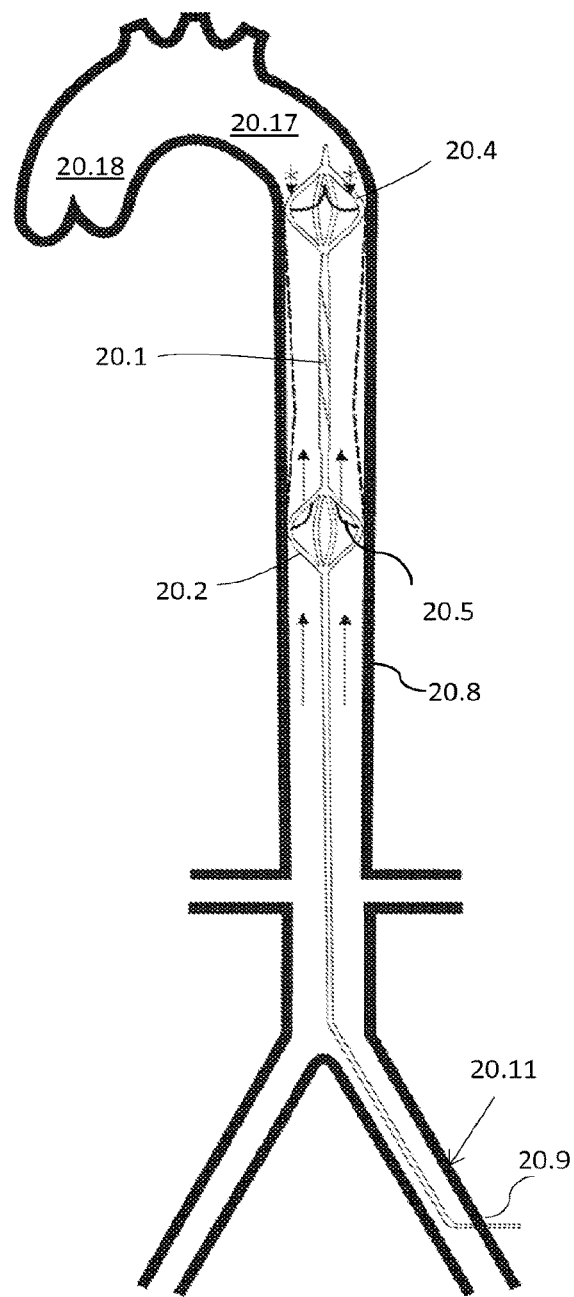
Figure 20B:
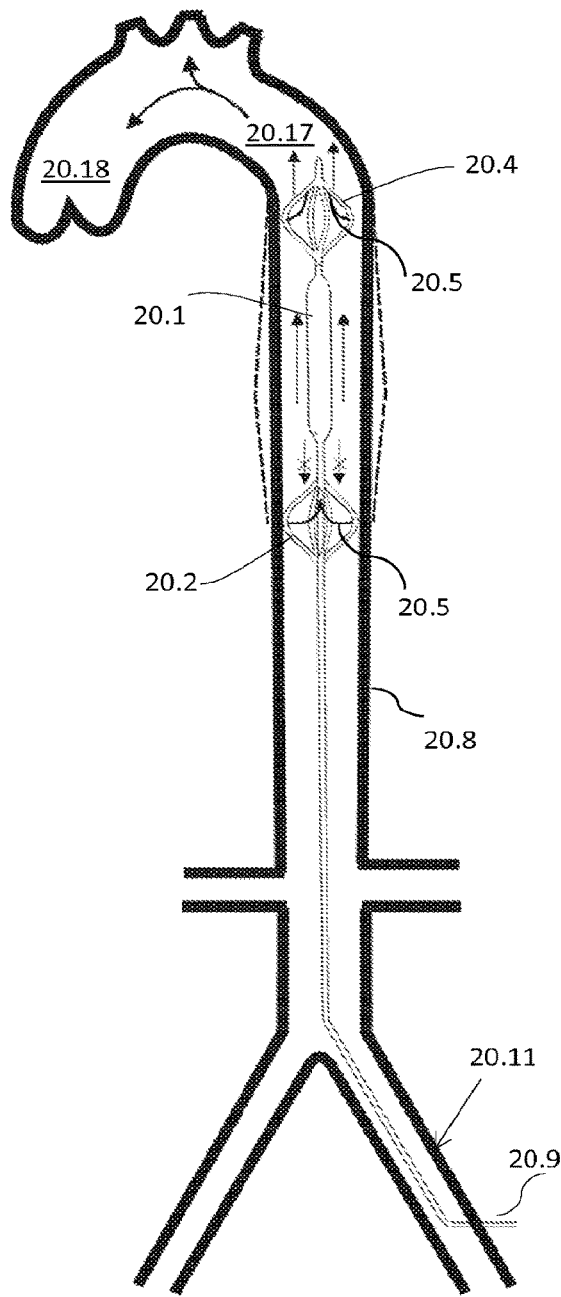

FIGS. 20a and 20b depict an embodiment and method for augmenting the pressure within the ascending aorta 20.18 and aortic arch 20.17, when a patient is in a state of cardiac arrest, by advancing blood towards the heart from the periphery. If cardiac function ceases completely, the only pool of blood that can be mobilized and sent to the brain and heart is the one that resides within the aorta 20.8. The inventor has observed in a series of experiments that if the aortic pressure is increased substantially, to 180 mm Hg or more temporarily (for 10-30 sec), this increases substantially the coronary perfusion to the extent that even a >1 min completely arrested heart may be restarted. In a similar clinical scenario, if detrimental massive bleeding occurs peripherally (e.g., traumatic abdominal aorta rupture) and the heart has arrested, the apparatus of FIG. 20 can be inserted to mobilize all residual arterial aortic blood towards the heart and the brain.

The apparatus in this embodiment is essentially the same as the apparatus shown in FIGS. 6a and 6b, but is inserted through a peripheral artery 20.11 (here the left femoral) at a state of cardiac arrest. Distally-opening check valves 20.5 thus enable forced, intentional upstream flow to the ascending aorta 20.18 and aortic arch 20.17, supplying arterial blood to the coronary ostiae. As shown in FIG. 20a, when the pumping balloon 20.1 is deflated, the pressure drops in the thoracic aorta 20.7, the distal check valve 20.5 of the expandable frame 20.4 closes, and the proximal check valve 20.5 of the proximal expandable frame 20.2 opens as blood is vacuumed within the area of low pressure. As shown in FIG. 20b, when the pumping balloon 20.1 inflates, the pressure in the thoracic aorta 20.7 increases, the proximal check valve 20.5 of the expandable frame 20.2 closes, and the distal check valve 20.5 of the expandable frame 20.4 opens to send blood in the aortic arch 20.17.

FIG. 21 shows an exemplary, pre-sized expandable frame or stent structure including a check valve, from fully collapsed (i) to partially (iii-v) and fully deployed (vi). The expandable frame can be either self-expanding or inducibly-expanding, and biases the frame into either a loose or tight engagement with the surrounding lumen. The mode of engagement (tight or loose) will depends upon the lumen tissue's elasticity, fragility, and pathology. The deployed check valve (vi) 21.5 creates an essentially unidirectional fluid passageway.

If self-expanding, the frame has a predetermined size and exhibits a predetermined expansion force. If inducibly-expanding, its size can be assessed either as mentioned earlier or radiographically with suitable radiopaque markers on its surface via fluoroscopy or ultrasound techniques. Generally, whether self-expanding or inducibly-expanding, the expandable frame is pre-sized to open 1-5 mm beyond the width of the lumen and in sufficiently conformity with it to prevent damaging it. A thin synthetic coating may cover the frame member surfaces that engage the surrounding tissue, thereby preventing direct contact between the members and the tissue.

The check valve 21.5 is composed of a thin synthetic material, forming a membrane and is anchored on the frame, preferably on the inner surface 21.13 of the frame members. This membrane is made of a biocompatible material (such us TEFLON, DACRON, polyethylene, polyamide, nylon, polyurethane, natural rubber, synthetic rubber, thermoplastic elastomer or thermoset polymer and the like), and may be treated to have anti-thrombotic properties. It preferably takes the form of a truncated cone. The diameter and perimeter of the neck of the cone 21.21 is larger than the corresponding diameter and perimeter of the expanded frame 21.2 at the same axial location so as to be able to bulge towards the center of the frame. The diameter of the base of the cone 21.22 matches the diameter of the expanded frame 21.2 at the same axial location, and the perimeter is the same as an imaginary continuous perimeter of the frame at the same axial location. Ideally the number frame members corresponds to the number of leaflets 21.5a, 21.5b, etc. The frame members support the check valve structure in the same way that stent arms support a tissue bioprosthesis, like those used for tissue valve replacement in humans. The check valve structure is generally attached to the inner surfaces and/or sides of the individual frame members, such that when the frame 21.2 is expanded the check valve 21.5 almost simulates a truncated cone, as it is shown in FIG. 24 sub c, with its neck end portions bulging towards the lumen walls. When the check valve 21.5 closes the collapsing neck structure 21.21 forms a bileaflet shape (not shown), a trileaflet shape (FIG. 21 sub b, a quadrileaflet shape, (FIG. 21 sub a), etc. depending upon whether the neck 21.21 is attached to each frame member, each other frame member, etc. and the number of frame members. The thicker the check valve material, the more difficult it is for the check valve at the same axial location 21.5 to collapse at a small size, but the more supple and resistant it becomes. However the inventor has observed that multi-leaflet valves (2-8 leaflets) made of thin material collapse well to produce a thin structure whilst maintaining their resistance and ability to follow a patterned movement even with repetitive opening and closure.

DESCRIPTION OF APPLICABILITY AND ADVANTAGES (1) Enhancement of Vacuum Effect Through the Use of Unidirectional 'Downstream' Check Valves Illustrated and suggested embodiments may be particularly useful in the common case where a femorally inserted IAB is more or less used to draw ('vacuum') blood from a failing heart. An expandable frame, mounted upon the balloon catheter tube and combined with check valve placed just below the IAB allows blood to flow downstream—with relation to normal blood flow—but not upstream. Subsequently during the pumping balloon's inflation there is no 'retrograde' flow towards the balloon, e.g., from the lower aorta. This augments the off-loading effect of the apparatus' counterpulsation on a failing or compromised heart compared with conventional IABs.

(2) Ascending Aorta IAB Placement and Downstream Valve for Enhancement of Vacuum Effect Illustrated and suggested embodiments may act like an LVAD. More specifically a small pumping balloon (5-12 cm in length, 1-3.5 cm in diameter) may be mounted on a balloon catheter and placed in the ascending aorta. It may be further combined with an expandable frame, integrating a check valve, on its proximal balloon portion thus allowing downstream flow but preventing upstream flow. The system may be fed through the femoral artery and positioned such that the check valve resides at the level of the right subclavian artery. During deflation of the pumping balloon the check valve prevents 'retrograde flow' originating from the aortic arch, thereby drawing a volume of blood that equals its volume directly from the Left Ventricle (LV), effectuating the use of the apparatus as an LV assist device. The pumping balloon may be surrounded by an expandable frame thereby preventing elastic recoil during the balloon's deflation and trauma to the ascending aorta during the balloon's inflation. The expandable frame may be funnel-shaped or malecot-type.

(3) Descending Aorta IAB Placement for Enhancement of Body Organs Flow, Other from the Heart When a pumping balloon inflates, this creates 'surplus' volume in the space surrounding the balloon and generates pressure wave, originating from the balloon towards all directions. This creates a 'flow effect' which is particularly useful in the case of stenotic coronary arteries, brain arteries or renal arteries or any portion of the circulation. However a large portion of this 'flow effect' is lost towards the lower limbs or upper limbs or any part of the circulation—essentially non vital organs—that may not be 'particularly on demand' for flow. This may be called 'flow waste' in the sense that the flow cannot be directed to the organ that is in need of high flow perfusion, versus the organ that can survive with low perfusion. For example it becomes easily understood by those familiar with the art that in the case of acute pre-renal failure during Cardiopulmonary By-Pass, renal failure may occur due to a transient decrease of renal flow, although the heart and the brain may not be particularly on demand. Likewise brain ischemia may occur although the kidneys may not be particularly on demand.

Illustrated and suggested embodiments eliminate this 'flow waste' by including a check valve placed just downstream form the arteries supplying the organ that is not on demand, thereby preventing 'flow waste' upon said level and giving priority to an organ below this level. This downstream-opening check valve is combined with a more downstream pumping balloon so that the check valve is positioned above it. This combination will allow downstream flow (in relation to the normal blood flow from the heart) during the balloon's deflation, but prevent upstream flow during the balloon's inflation. An additional downstream-opening check valve placed downstream from the balloon—as described before—will increase 'vacuuming' from the heart.

(4) Use of IAB Through the Cannulation Site to Increase Renal Perfusion

Illustrated and suggested embodiments may be particularly useful in the case of a heart on CPB, and may supply counterpulsation through an aortic cannulation site. More specifically an pumping balloon, mounted on a balloon catheter, having expandable frames on either side of pumping balloon, each including a check valve, may be fed through the aortic cannulation site. Both check valves allow downstream flow, but prevent upstream flow. the pumping balloon is placed at the level of the renal arteries and appropriately centered—thereby avoiding transient renal artery flow blockade during counterpulsation. The expandable frames deploy outwardly and position the check valves above and below the renal arteries, defining a 'renal arteries compartment'. The proximal or upstream check valve will allow blood to enter the 'renal arteries compartment' upon the pumping balloon's deflation, but it will prevent blood 'flow waste' above said proximal check valve during the pumping balloon's inflation, thereby increasing the flow to the renal arteries. The distal or downstream check valve will prevent retrograde flow from the lower limbs during the pumping balloon's inflation, thereby increasing downstream flow, 'vacuum' effect, and blood pooling in the 'renal arteries compartment'.

(5) Use of IAB Through the Femoral Site to Increase Renal Perfusion

Illustrated and suggested embodiments may be particularly useful in the case of pre-renal failure where an increase of renal blood flow is desired. More specifically an pumping balloon mounted on a balloon catheter as described above may be inserted through the femoral artery and used to specifically increase renal blood flow.

(6) Use of IAB Through the Femoral Site to Increase Brain Perfusion

Illustrated and suggested embodiments may be particularly useful in the case of the brain ischemia where an increase of brain blood flow is desired. An pumping balloon mounted on a balloon catheter, having expandable frames on either side of pumping balloon, each including a check valve, is fed through the femoral artery. Both check valves allow downstream flow, but prevent upstream flow. The pumping balloon is placed at the level of the thoracic aorta and appropriately centered—thereby avoiding balloon-to-aortic-wall contact during counterpulsation. The expandable frames deploy outwardly and position the check valves above and below the level of the innominate and right subclavian arteries, defining a 'brain arteries compartment'. The pumping balloon operates in counterpulsation mode, and the distal or upstream check valve will allow blood to enter upon the pumping balloon's deflation, but it will prevent blood 'flow waste' towards the heart during the pumping balloon's inflation, thereby increasing the flow to the encephalic arteries. The proximal or downstream check valve will prevent retrograde flow from the lower limbs during the balloon's deflation, thereby increasing downstream flow, 'vacuum' effect and, blood pooling in the 'brain arteries compartment'. The system may further comprise a lower proximal or downstream valve, which functions as a blocking element during the pumping balloon's inflation. During heart's systole downstream flow is allowed creating pooling of blood in the 'brain arteries compartment.' During heart's diastole and gated IAB's inflation both valves—distal and lower proximal—valves may close and thus pressure and flow effect is localized only in the 'brain arteries space area'.

(7) Flow Augmentation in the Periphery

It is an aim to provide a pumping balloon system for augmenting axial directional flow and increasing downstream axial flow to any part of the circulation, such as in small peripheral arterial branches or big branches of the venous circulation.

Illustrated and suggested embodiments for such applications typically include a pumping balloon, mounted on a balloon catheter, with expandable frames (proximal and distal) disposed on either side, which are fed through a peripheral vessel. Either expandable frame may include a passive unidirectional check valve mounted thereupon. The pumping balloon is placed within the peripheral vessel and appropriately centered—thereby avoiding transient flow blockade during counterpulsation, if used. The expandable frames are deployed outwardly, and thus said unidirectional check valves are also deployed, above and below the peripheral arteries defining an 'underperfused area'. Proximal expandable frame's check valve allows downstream flow towards the pumping balloon, but prevents upstream flow, allowing blood to enter the underperfused area upon the pumping balloon's deflation, but preventing blood 'flow waste' above said proximal check valve during the pumping balloon's inflation, thereby increasing the flow into the specific underperfused area. Distal expandable frame's check valve will prevent retrograde flow from the lower limbs during pumping balloon's inflation, thereby increasing downstream flow, 'vacuum' effect, and blood pooling in the 'underperfused area'.

(8) Descending Aorta IAB Placement Integrating Blocking Element Above and Unidirectional Valve Below It is an aim to provide an expandable member in combination with an IAB-like pumping balloon, creating upstream flow to the brain or any part of the arterial circulation. This comprise a pumping balloon, placed downstream in relation with an expandable 'blocking element' and the normal blood flow, which counterbalances the decrease of the downstream flow secondary to the obstruction. This is particularly useful in the case of a Brain Transient Ischemic Attack or an ischemic stroke. A small pumping balloon, combined with a proximal expandable frame having a 'blocking element,' is inserted through a peripheral vessel (such as the femoral artery) and placed below the aortic arch. Upon expansion said expandable frame and blocking element occludes partially the aortic flow, thereby creating retrograde flow to the brain or any portion of the arterial circulation.

Hypothetical Claims

1. A circulatory assist apparatus for use to improve pressure and augment directional flow in the aorta, or any part of the circulation comprising:

An inflatable balloon means positioned within the aorta, or any vessel of the patient, formed of a non-stretchable plastic material, having a distal tip and a proximal ends;

A catheter tube having a distal end joined to the inflatable balloon means and a proximal end, out of the body, receiving positive and negative pressure pulses for the balloon's inflation and deflation;

A centering means, mounted on at least at one portion of said catheter tube or balloon means tip, for positioning the balloon means in the center space of the aorta or a body vessel, thereby preventing balloon/vessel wall contact, reducing whipping effect during inflation and passive follow movement of the vessel wall during deflation; said centering means having a first diameter at a closed configuration for intraluminal delivery, and a second diameter at a deployed configuration for operation.

Operating means connected to said centering means,

Valve means, collapsible and extendable, mounted on said centering means capable of regulating flow in the body vessel by blocking flow in one or more directions upon said centering means expansion.

2. The apparatus of claim 1 wherein said body vessel refers primarily to the aorta and main arterial branches, and secondarily to any body channel of the arterial, venous, urinary, biliary, lymphatic and cerebrospinal circulation.

3. The apparatus of claim 1 wherein said catheter tube is being sized and dimensioned to permit placement through a peripheral vessel.

4. The apparatus of claim 1 wherein said inflatable balloon means comprising of one inflatable balloon.

5. The apparatus of claim 1 wherein said inflatable balloon means comprising of more than one inflatable balloon means, longitudinally aligned, placed in close proximity one another and interconnected with intra-balloon catheter portions, forming a single series of inflatable balloons.

6. The apparatus of claim 5 wherein intra-balloon catheter portions resemble catheter tube portions and may accommodate said centering means.

7. The apparatus of claim 6 wherein said interconnecting catheter portions having a length bigger compared to the length of said centering means when collapsed and thus sufficient to enable said resilient means to slide and collapse, or deploy.

8. The apparatus of claim 1 wherein said operating means extends beyond and is accessible from the proximal end of said catheter tube, being out of the body.

9. The apparatus of claim 1 wherein said operating means constitute linearly movable means, being movable in a first direction for effective deployment of said centering means and in a second opposite direction for effective collapse.

10. The apparatus of claim 1, wherein said centering means comprises a collapsible radially expandable member, having a proximal and a distal portions that are connected with a middle portion; said middle portion comprising a plurality of stent arms pretreated to expand outwardly in a predetermined manner.

11. The apparatus of claim 1 wherein said centering means are constructed of an elastic material, preferably a shape memory alloy like superelastic Nitinol.

12. The apparatus of claim 1, wherein said centering means is pretreated to obtain such a stereo-configuration upon expansion, adapted to fit, and at least partially conforming to the generally cylindrical shape of said body channel or asymmetric portions thereof.

13. The apparatus of claim 12 wherein said centering resilient means is pretreated to self-expand to a predetermined diameter, which at the expanded state is smaller to the inner diameter of said body channel.

14. The apparatus of claim 12 wherein centering means is pretreated to obtain a generally collapsed state, and deploy outwardly to expand through axial movement of said operating means.

15. The apparatus of claim 14 wherein axial movement of said operating means in one direction causes the distal portion and proximal portion of said centering means to approach one another, and the middle portion to deploy outwardly, into dynamic engagement with the interior surface of said body vessel, whereas axial movement in the opposite direction causes said centering means to collapse.

16. The apparatus of claim 1 wherein said centering means comprising a tube slit; having a proximal tube portion, a middle portion, comprising a plurality of elongated strips, and a distal tube portion.

17. The apparatus of claim 16 wherein said centering means further comprising a plurality if substantially U or V-shaped, or zigzag resilient members positioned between said strips middle portion for forming an annular portion, for mounting of said valve means.

18. The apparatus of claim 1 wherein said centering means comprising a tubular braid, a tubular mesh or a twist of superelastic filaments (wires or tubes), or any combination thereof (i.e. wire struts welded or crimped on tube portions, wire struts originating from larger wire twists, braids or meshes) forming a middle portion of generally longitudinal struts; having a proximal tubular portion, a middle portion, comprising a plurality of elongated struts of single filaments or wire twists, and a distal tubular portion.

19. The apparatus of claim 18 wherein said centering means having a middle portion wherein one or more of the plurality of elongated wire twists struts supply and interconnect their wires, at desired bending point, to form an annular portion, for mounting of said valve means.

20. The apparatus of claim 19 wherein said annular portion is a wire braid, wire twist, or wire mesh, or any combination thereof, heat set and pretreated to obtain, upon expansion, a stereo-configuration, adapted to fit within the body channel, and at least partially conforming to the generally cylindrical shape of said body channel or asymmetric portions thereof.

21. The apparatus of claim 1 wherein said centering means, is mounted on the catheter tube portion adjacent to the balloon or any portion thereof.

22. The apparatus of claim 21 wherein the inner diameter of said centering means is greater than the outer diameter of said catheter tube.

23. The apparatus of claim 22 wherein said centering means being removably slidable along the catheter tube axis.

24. The apparatus of claim 23 wherein said centering means is having a distal portion adjacent or joined to the distal end of said catheter tube, and a proximal end coupled to operating means.

25. The apparatus of claim 23 further comprising a stop element placed between the catheter tube distal end and centering means distal end portions, being capable of blocking advancement of said centering means beyond the catheter tube distal end.

26. The apparatus of claim 24 wherein said operating means is comprising an elongate tube, having a distal end coupled to the proximal portion of said centering resilient means, and a proximal end accessible from the proximal end of said catheter tube.

27. The apparatus of claim 26 wherein said operating means having an inner diameter respectively equal to the inner diameter of said centering resilient means, larger to the outer diameter or said catheter tube.

28. The apparatus of claim 24 wherein said operating means comprising elongate a single or a plurality of wire members, having a distal end coupled to the proximal portion of said centering resilient means, and a proximal end accessible from the proximal end of said catheter tube.

29. The apparatus of claim 28 wherein said centering means is radially expanded to a deployed configuration when said operating means is movable in a first direction, towards the balloon means, and being contracted and collapsed when pulled in the opposite direction.

30. The apparatus of claim 22 wherein said centering means is having their proximal portion, joined to a catheter tube portion, adjacent to the balloon means proximal end, and their distal portion, free to move about, thereby said centering means being removably slidable, along the axis of said catheter tube, between a closed and deployed configuration.

31. The apparatus of claim 30 wherein said catheter tube, accommodating said centering means, is having a length larger to the length of said centering means, and an outer diameter smaller to the inner diameter of said centering means.

32. The apparatus of claim 31 wherein said centering means is operated coupled for deployment to operating means linearly movable.

33. The apparatus of claim 32 wherein said operating means being a sleeve tube, comprising an elongate hollow portion, slidably and removably disposed, about said centering means, thereby controlling the transformation of said centering means from a closed to a deployed configuration.

34. The apparatus of claim 33 wherein said operating means having a distal end surrounding said centering means, and a proximal end accessible from the proximal end of said tube catheter.

35. The apparatus of claim 34 wherein said operating means having an inner diameter, larger to the outer diameter of said centering means.

36. The apparatus of claim 35 wherein said centering means is pushed and radially expandable when said operating means, is movable in a first direction, towards the balloon means, and being contracted and collapsed when pulled in the opposite direction.

37. The apparatus of claim 32 wherein said operating means comprise elongate resilient members, being linearly movable, having a distal ends joint to said centering resilient means, and a proximal end accessible from the proximal end of said catheter tube, for operating said centering means.

38. The apparatus of claim 37 wherein said centering means is contracted, slided and collapsed when said operating means is pulled in a first direction away from balloon means, and being released and radially expanding when said operating means is released, moving in a direction back to original position.

39. The apparatus of claim 38 wherein said operating means have an outer diameter smaller compared to the outer diameter of catheter tube.

40. The apparatus of claim 39 wherein said catheter tube further comprising a multiple lumen tube, having at least two lumens, longitudinally fixed into or around said catheter tube to accommodate said operating means.

41. The apparatus of claim 1 wherein said centering means, is mounted on a non-catheter tube segment, a balloon means tip portion or an intra-balloon catheter portion.

42. The apparatus of claim 41 wherein said non-catheter tube portion, balloon means tip portion and intra-balloon catheter portion, comprising similar elongated hollow portions, resembling the lumen of catheter tube portion, positioned distally in relation to at least one inflatable balloon means.

43. The apparatus of claim 42 wherein said non-catheter tube segment having proximal and distal end portions, accommodating at least one said centering means.

44. The apparatus of claim 43 wherein said non-catheter tube segment having an outer diameter smaller to the inner diameter of said centering means and a length, larger to the length of said centering means, when said centering means is at said closed configuration.

45. The apparatus of claim 44 wherein said centering means is having a proximal portion, coupled to the proximal end portion of said non-catheter tube segment, free to move about, thereby said centering means being removably slidable along, the axis of said non-catheter tube segment, between a closed and deployed configuration.

46. The apparatus of claim 45 wherein said centering means is operated coupled for deployment to operating means linearly movable.

47. The apparatus of claim 46 wherein said operating means being a sleeve tube, comprising an elongate hollow portion, slidably and removably disposed, about said centering means, thereby controlling the transformation of said centering means from a closed to a deployed configuration.

48. The apparatus of claim 47 wherein said operating means having a distal end surrounding said centering means, and a proximal end accessible from the proximal end of said tube catheter.

49. The apparatus of claim 48 wherein said operating means having an inner diameter, larger to the outer diameter of said centering means.

50. The apparatus of claim 46 wherein said operating means comprise elongate resilient members, being linearly movable, having a distal ends joint to said centering resilient means, and a proximal end accessible from the proximal end of said catheter tube, for operating said centering means.

51. The apparatus of claim 50 wherein said centering means is contracted, slided and collapsed when said operating means is pulled in a first direction away from balloon means, and being released and radially expanding when said operating means is released, moving in a direction back to original position.

52. The apparatus of claim 51 wherein said operating means have an outer diameter smaller compared to the outer diameter of non-catheter tube segment.

53. The apparatus of claim 51 wherein said non-catheter tube segment, further comprising a multiple lumen tube, having at least two lumens, longitudinally fixed into or around said catheter tube to accommodate said operating means.

54. The apparatus of claim 44 wherein said centering means is having a distal portion adjacent or joined to the distal end of said non-catheter tube segment, and a proximal end coupled to operating means.

55. The apparatus of claim 54 wherein said operating means comprising elongate a single or a plurality of wire members, having a distal end coupled to the proximal portion of said centering resilient means, and a proximal end accessible from the proximal end of said catheter tube.

56. The apparatus of claim 55 wherein said centering means is radially expanded to a deployed configuration when said operating means is movable in a first direction, towards the balloon means, and being contracted and collapsed when pulled in the opposite direction.

57. The apparatus of claim 1 comprising any number of said centering means and at least one valve means mounted upon, thereby converting said centering means to a valvular centering means.

58. The apparatus of claim 57 wherein said valve means is operatively coupled to the expansion of said centering means mounted upon, being supple enough to follow said centering means collapse and expansion.

59. The apparatus of claim 57 wherein said valve means comprising of a biocompatible membrane, refractory to the pressures of flows within the body channel.

60. The apparatus of claim 57, wherein said valvular means is constructed and arranged such that, when fully expanded, substantially sealing the desired portion of the body passageway, without impeding the flow.

61. The apparatus of claim 57 wherein said valve means being permanently attached to the external and/or internal surface of said centering means or any portion thereof.

62. The apparatus of claim 57 wherein said valve means being permanently attached to said centering means, directly or indirectly through an annular portion adherent thereto.

63. The apparatus of claim 62 wherein said annular portion comprises a circular stent zigzag superelastic structure, a wire braid, a wire twist, or any combination thereof.

64. The apparatus of claim 57 wherein said valve means being directly fastened to a substantial portion of the external and/or internal surface of said valvular centering means by sewing, molding or gluing to achieve a sealing sufficient to prevent any flow between the centering means and the valvular structure.

65. The apparatus of claim 57 wherein said valvular tissue is made of synthetic biocompatible material such us TEFLON, DACRON, polyethylene, polyamide, nylon, polyurethane, natural rubber, synthetic rubber, thermoplastic elastomer or thermoset polymer and the like.

66. The apparatus of claim 66 wherein said valvular tissue is made of synthetic biocompatible material such us TEFLON, DACRON, polyethylene, polyamide, nylon, polyurethane, natural rubber, synthetic rubber, thermoplastic elastomer or thermoset polymer and the like, supported by a nitinol superelastic mesh, made of wires, arranged in a parallel or intersecting pattern.

67. The apparatus of claim 57 wherein said valve means is capable of regulating passively the flow in said body vessel, thereby comprising one way valve means.

68. The apparatus of claim 67 wherein said valve means comprising a trunco-hyperboloidal valve trealeflet, having a larger base, attached to said annular portion and a narrow neck.

69. The apparatus of claim 67 wherein said valve means comprising an almost hemispherical valve, having its convex surface on the flow side, configured to collapse freely on its concave surface and ensure not to impede downstream flow with respect to the normal blood flow, or any other bodily flow.

70. The apparatus of claim 69 wherein said hemispherical valve having its convex surface or any portion thereof fixed to a substantial portion of the internal surface of said centering means by sewing, molding or gluing, thereby oriented collapsible downstream with respect to normal blood flow, and is supple and resistant enough to ensure not to impede the downstream flow and achieve sufficient sealing during upstream flow.

71. The apparatus of claim 57 wherein said valvular centering means further comprises at least one collateral inflatable balloon means, fluidically connected to said balloon means for use convert said one way valve means to a transient flow occluder, during said balloon means inflation.

72. The apparatus of claim 71 wherein said collateral inflatable balloon means is enclosed into said valvular centering means, and adapted in close proximity with said valve means, upstream in relation to the passive valve means opening, thereby blocking the opening of said valve means upon inflation, and allowing the operation of the valve upon deflation.

73. The apparatus of claim 72 wherein said collateral inflatable balloon means is having a spherical, reverse cone or any 3D shape and a diameter smaller, compared to the annular diameter of said valvular centering means.

74. The apparatus of claim 71 wherein said collateral inflatable balloon means further comprising a disc shaped balloon, having a diameter equal or smaller, compared to the diameter of said valvular centering means, fused into the central portion of said valve means, thereby preventing valvular opening during balloon means inflation.

75. The apparatus of above claim 74 wherein said valve means is supple and resistant enough to maintain a closed configuration, against the body fluid flow, particularly supported by the inflation of said disc shaped balloon, which is integrated in its structure comprising an inflatable pouch.

76. The apparatus of claim 71 wherein said collateral inflatable balloon means is adjacent to said valvular centering means, being in close proximity, downstream, arranged such that it is causing a substantial local pressure augmentation, upstream in relation to said valve means opening, and relatively higher to the pressure on the other side of said valvular means, thereby converting said one way valve means to a transient flow occluder, during said balloon means inflation.

77. The apparatus of claim 76 wherein said collateral inflatable balloon means, adjacent to said valvular centering means, is enclosed into a second said centering means, downstream, thereby preventing body vessel contact and/or pressure trauma on the surrounding body vessel during said collateral inflatable balloon means inflation.

78. The apparatus of claim 71 wherein said collateral inflatable balloon means is enclosed into said centering means thereby preventing body vessel contact and pressure trauma on the surrounding body vessel, during said collateral inflatable balloon means inflation.

79. The apparatus of claim 78 wherein said collateral inflatable balloon means is enclosed into said centering means thereby preventing body vessel contact and pressure trauma on the surrounding body vessel, during said collateral inflatable balloon means inflation.

80. The apparatus of claim 79 wherein an internal biocompatible polymer cover, supple enough to follow said centering means collapse and expansion, and resistant enough to sustain body passage fluid flows and pressures, comprising a ring-like portion, is integrated into the centering means of said collateral balloon means, placed circumferentially between said collateral balloon means and the annular portion of said centering means, thereby preventing passage of body fluid through, during said collateral balloon means inflation.

81. The apparatus of claim 81 wherein the inner diameter of said ring like portion is smaller or approximately equal compared to the outer diameter of said collateral balloon means.

82. The valvular structure of claim 1 wherein the prosthetic valve is treated with a substance having anti-thrombotic properties.

83. The apparatus of claim 6 of wherein said inflatable balloon means, in the case of three inflatable balloon means is comprising of:
   a) A catheter tube having a proximal end out of the body and a distal hollow portion terminating to a first balloon,
   b) A first inflatable balloon having a proximal portion mounted on hollow portion of said catheter and a distal portion terminating to the hollow portion of next second catheter portion
   c) A first intra-balloon catheter portion having a proximal hollow portion and a distal hollow portion terminating to a second balloon,
   d) A second inflatable balloon having a proximal portion mounted on distal hollow portion of said first intra-balloon catheter portion, and a distal portion terminating to the hollow portion of second intra-balloon catheter portion,
   e) A second balloon intra-catheter portion having a proximal hollow portion and a distal hollow portion terminating to third balloon,
   f) A third inflatable balloon having a proximal hollow portion and a distal closed portion, terminating to a balloon means tip portion.

It will be understood that these are hypothetical claims only, not the examined claims of the application.

What is claimed is:

1. A circulatory assist apparatus for use to improve pressure and create and augment flow in an aorta or other circulatory lumen, the apparatus comprising:
   an inflatable pumping balloon having a proximal end joined to an elongated balloon catheter, the balloon catheter having a distal end joined to the pumping balloon and a proximal end, separated from the distal end by a length sufficient to extend from within the circulatory lumen to the outside of a patient's body, for receiving positive and negative pressure pulses from a pump to inflate and deflate the pumping balloon;
   a first radially expandable frame, mounted on a segment extending distally from the pumping balloon, wherein the first expandable frame is manipulable to expand within the circulatory lumen, and functions to space apart the inflatable pumping balloon from the circulatory lumen, said first expandable frame having a first diameter in a collapsed configuration for intraluminal delivery and a second, larger diameter in an expanded configuration achieved by said manipulation;
   a second radially expandable frame, disposed proximally from said pumping balloon and mounted on one of the balloon catheter and a sleeve tube surrounding the balloon catheter, wherein the second expandable frame is manipulable to expand within the circulatory lumen, and functions to space apart the inflatable pumping balloon from the circulatory lumen, said expandable frame having a first diameter in a collapsed configuration for intraluminal delivery and a second, larger diameter in an expanded configuration achieved by said manipulation; and
   an occlusive balloon disposed proximally from said second radially expandable frame and fluidly connected to said inflatable pumping balloon,
   wherein said second expandable frame includes a proximally-opening check valve interposed between the occlusive balloon and the inflatable pumping balloon.

2. The apparatus of claim 1 wherein said pumping balloon and said balloon catheter are sized and dimensioned to permit placement through a peripheral vessel.

3. The apparatus of claim 1, wherein said first expandable frame includes a check valve.

4. The apparatus of claim 3, wherein said check valve of the first expandable frame comprises a trunco-hyperboloidal valve, having a larger base and a narrower neck, with the narrower neck being collapsible into the first expandable frame in response to axial flow originating from the neck-side of the first expandable frame.

5. The apparatus of claim 4, wherein the check valve of the first expandable frame comprises a dome-shaped valve, having its convex surface on the flow side, configured to collapse freely on its concave surface and thus not to impede downstream flow.

6. The apparatus of claim 5, wherein said dome-shaped valve has its convex surface or any portion thereof fixed to a substantial portion of the internal surface of said first expandable frame by sewing, molding, or gluing, and thereby is oriented collapsible downstream with respect to axial flow impinging upon said convex surface.

7. The apparatus of claim 1, wherein said check valve comprises a trunco-hyperboloidal valve, having a larger base and a narrower neck, with the narrower neck being collapsible into the expandable frame in response to axial flow originating from the neck-side of the second expandable frame.

8. The apparatus of claim 7, wherein said check valve comprises a dome-shaped valve, having its convex surface on the flow side, configured to collapse freely on its concave surface and thus not to impede downstream flow.

9. The apparatus of claim 8, wherein said dome-shaped valve has its convex surface or any portion thereof fixed to a substantial portion of the internal surface of said second expandable frame by sewing, molding, or gluing, and thereby is oriented collapsible downstream with respect to axial flow impinging upon said convex surface.

10. The apparatus of claim 1, wherein the first radially expandable frame has an expanded diameter of between 6 mm and 30 mm, and the first radially expandable frame is partially radially expandable to conform to a first predetermined target diameter of a wall of the aorta or other circulatory lumen.

11. The apparatus of claim 10, wherein the second radially expandable frame has an expanded diameter of between 6 mm and 30 mm, and the second radially expandable frame is partially radially expandable to conform to a second predetermined target diameter of the wall of the aorta or other circulatory lumen, wherein the first and second predetermined target diameters may be the same as or different from each other.

12. A circulatory assist apparatus for use to improve pressure and create and augment flow in an aorta or other circulatory lumen, the apparatus comprising:
an inflatable pumping balloon having a proximal end joined to an elongated balloon catheter, the balloon catheter having a distal end joined to the pumping balloon and a proximal end, separated from the distal end by a length sufficient to extend from within the circulatory lumen to the outside of a patient's body, for receiving positive and negative pressure pulses from a pump to inflate and deflate the pumping balloon;
a first radially expandable frame, mounted on a segment extending distally from the pumping balloon, wherein the first expandable frame is manipulable to expand within the circulatory lumen, and functions to space apart the inflatable pumping balloon from the circulatory lumen, said first expandable frame having a first diameter in a collapsed configuration for intraluminal delivery and a second, larger diameter in an expanded configuration achieved by said manipulation;
a second radially expandable frame, disposed proximally from said pumping balloon and mounted on one of the balloon catheter and a sleeve tube surrounding the balloon catheter, wherein the second expandable frame is manipulable to expand within the circulatory lumen, and functions to space apart the inflatable pumping balloon from the circulatory lumen, said expandable frame having a first diameter in a collapsed configuration for intraluminal delivery and a second, larger diameter in an expanded configuration achieved by said manipulation; and
an occlusive balloon disposed proximally from said second radially expandable frame and fluidly connected to said inflatable pumping balloon,
wherein said second expandable frame includes a proximally-opening check valve interposed between the occlusive balloon and the inflatable pumping balloon; and
wherein the volume of the occlusive balloon or the spacing of the occlusive balloon from the second expandable frame are configured to delay the opening of the check valve upon inflation of the inflatable pumping balloon.

13. A circulatory assist apparatus for use to improve pressure and create and augment flow in an aorta or other circulatory lumen, the apparatus comprising:
an inflatable pumping balloon having a proximal end joined to an elongated balloon catheter, the balloon catheter having a distal end joined to the pumping balloon and a proximal end, separated from the distal end by a length sufficient to extend from within the circulatory lumen to the outside of a patient's body, for receiving positive and negative pressure pulses from a pump to inflate and deflate the pumping balloon;
a first radially and reversibly expandable frame, mounted on a segment extending distally from the pumping balloon, wherein the first expandable frame is manipulable to expand and collapse within the circulatory lumen, and functions to space apart the inflatable pumping balloon from the circulatory lumen, said first expandable frame having a first diameter in a collapsed configuration for intraluminal delivery and withdrawal and a second, larger diameter in an expanded configuration achieved by said manipulation;
a second radially and reversibly expandable frame, disposed proximally from said pumping balloon and mounted on one of the balloon catheter and a sleeve tube surrounding the balloon catheter, wherein the second expandable frame is manipulable to expand and collapse within the circulatory lumen, and functions to space apart the inflatable pumping balloon from the circulatory lumen, said second expandable frame having a first diameter in a collapsed configuration for intraluminal delivery and withdrawal and a second, larger diameter in an expanded configuration achieved by said manipulation; and
an occlusive balloon disposed proximally from said second radially and reversibly expandable frame and fluidly connected to said inflatable pumping balloon, wherein said first expandable frame includes a first check valve.

14. The apparatus of claim 13, wherein said second expandable frame includes a second check valve.

15. The apparatus of claim 14, wherein said second check valve comprises a trunco-hyperboloidal valve, having a larger base and a narrower neck, with the narrower neck being collapsible into the expandable frame in response to axial flow originating from the neck-side of the second expandable frame.

16. The apparatus of claim 14, wherein said second check valve comprises a dome-shaped valve, having its convex surface on the flow side, configured to collapse freely on its concave surface and thus not to impede downstream flow.

17. The apparatus of claim 16, wherein said dome-shaped valve has its convex surface or any portion thereof fixed to a substantial portion of the internal surface of said second expandable frame by sewing, molding, or gluing, and thereby is oriented collapsible downstream with respect to axial flow impinging upon said convex surface.

18. The apparatus of claim 13, wherein said first check valve comprises a trunco-hyperboloidal valve, having a larger base and a narrower neck, with the narrower neck being collapsible into the first expandable frame in response to axial flow originating from the neck-side of the first expandable frame.

19. The apparatus of claim 13, wherein said first check valve comprises a dome-shaped valve, having its convex surface on the flow side, configured to collapse freely on its concave surface and thus not to impede downstream flow.

20. The apparatus of claim 19, wherein said dome-shaped valve has its convex surface or any portion thereof fixed to a substantial portion of the internal surface of said first expandable frame by sewing, molding, or gluing, and thereby is oriented collapsible downstream with respect to axial flow impinging upon said convex surface.

\* \* \* \* \*